(12) United States Patent
Stoessel et al.

(10) Patent No.: US 10,407,384 B2
(45) Date of Patent: Sep. 10, 2019

(54) SYNTHETIC BUILDING BLOCKS FOR THE PRODUCTION OF MATERIALS FOR ORGANIC ELECTROLUMINESCENCE DEVICES

(71) Applicant: Merck Patent GmbH, Darmstadt (DE)

(72) Inventors: Philipp Stoessel, Frankfurt am Main (DE); Amir Hossain Parham, Frankfurt am Main (DE); Anja Jatsch, Frankfurt am Main (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 15/634,746

(22) Filed: Jun. 27, 2017

(65) Prior Publication Data

US 2017/0313650 A1 Nov. 2, 2017

Related U.S. Application Data

(62) Division of application No. 14/778,783, filed as application No. PCT/EP2014/000481 on Feb. 24, 2014, now Pat. No. 9,718,764.

(30) Foreign Application Priority Data

Mar. 22, 2013 (EP) ..................................... 13001485

(51) Int. Cl.
| | |
|---|---|
| C07D 403/10 | (2006.01) |
| C07D 333/76 | (2006.01) |
| C07C 253/20 | (2006.01) |
| C07C 255/51 | (2006.01) |
| C07C 51/16 | (2006.01) |
| C07C 51/60 | (2006.01) |
| C07C 231/02 | (2006.01) |
| C07D 209/86 | (2006.01) |
| C07D 235/18 | (2006.01) |
| C07D 239/26 | (2006.01) |
| C07D 251/24 | (2006.01) |
| C07D 307/91 | (2006.01) |
| C07C 253/14 | (2006.01) |
| C07C 253/30 | (2006.01) |
| C07D 209/80 | (2006.01) |
| C07D 209/88 | (2006.01) |
| C07D 487/04 | (2006.01) |

(52) U.S. Cl.
CPC ............ *C07C 253/20* (2013.01); *C07C 51/16* (2013.01); *C07C 51/60* (2013.01); *C07C 231/02* (2013.01); *C07C 253/14* (2013.01); *C07C 253/30* (2013.01); *C07C 255/51* (2013.01); *C07D 209/80* (2013.01); *C07D 209/86* (2013.01); *C07D 209/88* (2013.01); *C07D 235/18* (2013.01); *C07D 239/26* (2013.01); *C07D 251/24* (2013.01); *C07D 307/91* (2013.01); *C07D 333/76* (2013.01); *C07D 403/10* (2013.01); *C07D 487/04* (2013.01); *C07C 2601/16* (2017.05); *C07C 2602/10* (2017.05); *C07C 2603/18* (2017.05); *C07C 2603/24* (2017.05); *C07C 2603/26* (2017.05); *C07C 2603/42* (2017.05); *C07C 2603/97* (2017.05)

(58) Field of Classification Search
CPC .......................... C07D 403/10; C07D 333/76
See application file for complete search history.

(56) References Cited

U.S. PATENT DOCUMENTS

| | | | |
|---|---|---|---|
| 3,331,735 A | 7/1967 | Battershell et al. | |
| 4,556,426 A | 12/1985 | Chesney, Jr. et al. | |
| 7,608,604 B2 | 10/2009 | Comlay et al. | |
| 8,361,638 B2 | 1/2013 | Stoessel et al. | |
| 8,592,452 B2 | 11/2013 | Yamamoto et al. | |
| 8,825,306 B2 | 9/2014 | Dankers | |
| 8,846,978 B2 | 9/2014 | Hotchkiss et al. | |
| 2010/0152236 A1 | 6/2010 | Yamamoto et al. | |
| 2012/0114974 A1 | 5/2012 | Hotchkiss et al. | |

FOREIGN PATENT DOCUMENTS

| | | |
|---|---|---|
| CN | 102459290 A | 5/2012 |
| JP | S51-003974 A | 1/1976 |
| JP | S62240655 A | 10/1987 |
| JP | S62-294648 A | 12/1987 |
| JP | 2003137855 A | 5/2003 |
| JP | 2010518067 A | 5/2010 |
| JP | 2011521894 A | 7/2011 |
| JP | 2012522824 A | 9/2012 |
| JP | 201379937 A | 5/2013 |
| WO | WO-2003051119 A1 | 6/2003 |
| WO | WO-2007015567 A1 | 2/2007 |

OTHER PUBLICATIONS

Huang, C., et al., "Synthesis and antimicrobial activity of polyhalo isophthalonitrile", Bioorganic & Medicinal Chemistry Letters vol. 23, No. 8, (2013), pp. 2399-2403.
International Search Report for PCT/EP2014/000481 dated Jul. 7 2014.
Nandurdikar, R., et al., "Structural modifications modulate stability of glutathione-activated arylated diazeniumdiolate prodrugs", Biorrganic & Medicinal Chemistry, vol. 20, No. 9, (2012), pp. 3094-3099.
Patch, R., et al., "Identification of Diaryl Ether-Based Ligands for Estrogen-Related Receptor α as Potential Antidiabetic Agents", Journal of Medicinal Chemistry, vol. 54, No. 3, (2011), pp. 788-808.
Wallenfels, K., et al., "2,4-Dicyan- und 2,4,6-Tricyan-Fluorbenzol", Tetrahedron, vol. 23, No. 3 (1967), pp. 1353-1358.
Wallenfels, K., et al., "2,4-Dicyan- and 2,4,6-Tricyanofluorobenzene", Tetrahedron, vol. 23, pp. 1353-1358 (1967) (English translation).
English Translation of Chinese Office Action for application No. 201480017494.2, dated Mar. 7, 2017.

(Continued)

*Primary Examiner* — Shawquia Jackson

(74) *Attorney, Agent, or Firm* — Drinker Biddle & Reath LLP

(57) ABSTRACT

The present invention relates to compounds which are suitable as synthesis precursors for the production of electronically active materials for use in organic electroluminescence devices.

11 Claims, No Drawings

(56) References Cited

OTHER PUBLICATIONS

Bouyssou, P., et al., "Synthesis of 7- and 5,7-Substituted-6-fluro-2-methyl-1,2,3,4-tetrahydro-quinolines: Convenient Precursors of Quinolone Antibacterial Agents", Journal of Heterocyclic Chemistry, 1992, vol. 29, No. 4, pp. 895-898.

Heilman, W., et al., "Synthesis and Antiinflammatory Evaluation of Substituted Isophthalonitriles, Trimesonitriles, Benzonitriles, and Terephthalonitriles", Journal of Medicinal Chemistry, 1978, vol. 21, No. 9, pp. 906-913.

Japanese Office Action for Japanese Patent Application No. 2016-504508, dated Jan. 9, 2018.

Kornblum, N., et al., "Electron-Transfer Substitution Reactions: Facilitation by the Cyano Group", Tetrahedron, 1989, vol. 45, No. 5, pp. 1311-1322.

Uoyama, H., et al., "Highly efficient organic light-emitting diodes from delayed fluorescence", Nature, 2012, vol. 492, No. 7428, pp. 234-238.

SYNTHETIC BUILDING BLOCKS FOR THE PRODUCTION OF MATERIALS FOR ORGANIC ELECTROLUMINESCENCE DEVICES

CROSS-REFERENCE TO RELATED APPLICATIONS

This application is a Divisional application of U.S. Ser. No. 14/778,783 filed Sep. 21, 2015 which is incorporated by reference in its entirety. U.S. Ser. No. 14/778,783 is a national stage application (under 35 U.S.C. § 371) of PCT/EP2014/000481, filed Feb. 24, 2014, which claims benefit of European application 13001485.5, filed Mar. 22, 2013 both of which are incorporated herein by reference in their entirety.

The present invention relates to compounds which can be used as synthetic building blocks for the preparation of electronically active materials, in particular for organic electroluminescent devices.

The structure of organic electroluminescent devices (OLEDs) in which organic semiconductors are employed as functional materials is described, for example, in U.S. Pat. Nos. 4,539,507, 5,151,629, EP 0676461 and WO 98/27136. At present, donor-acceptor-substituted benzene derivatives, in particular those in which the acceptor groups are cyano groups which are in the meta-position to one another and the donor groups are carbazole derivatives, are also employed, in particular, for this purpose. Examples of such compounds are described in C. Adachi et al., Nature 2012, 492, 234-238. However, only the synthesis of symmetrically substituted compounds is disclosed here. Furthermore, chromatographic purification of the products was necessary, which makes, in particular, purification on an industrial scale more difficult. It is therefore desirable to have available compounds from which the desired, electronically active compounds can be synthesised in high yield and purity.

The object of the present invention is therefore the provision of compounds which are suitable as synthesis precursors for the production of electronically active components for use in organic electroluminescent devices in order on the one hand to be able to prepare the materials in good yield and purity and on the other hand to enable the person skilled in the art to have a greater possible choice of materials for the production of OLEDs.

Surprisingly, it has been found that certain compounds described in greater detail below achieve this object, are very highly suitable for the preparation of donor-acceptor-substituted materials for use in OLEDs. In these compounds, the fluorine substituent can be replaced selectively and in high yield by nucleophiles under mild reaction conditions in a nucleophilic aromatic substitution. The present invention therefore relates to these compounds.

The present invention relates to a compound of the formula (1), formula (2) or formula (3),

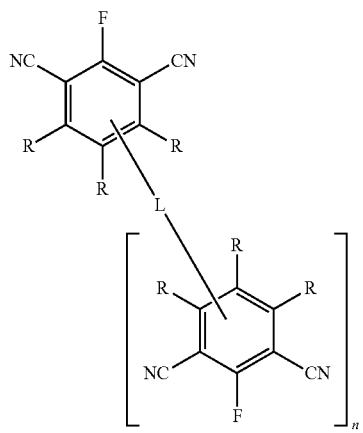

formula (1)

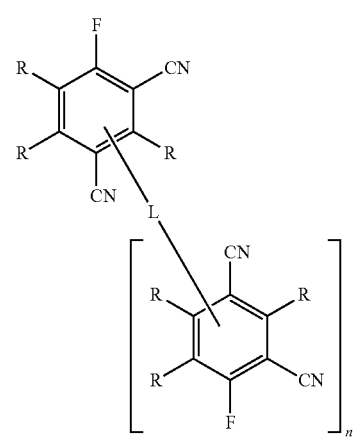

formula (2)

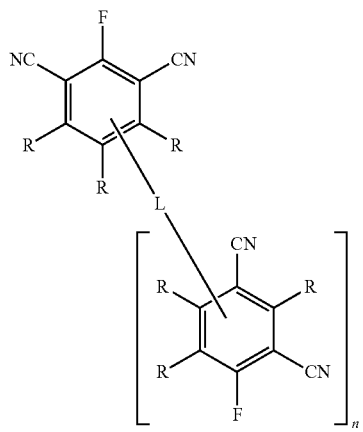

formula (3)

where the following applies to the symbols and indices used:

L is a single bond or a di-, tri-, tetra-, penta- or hexavalent group;

R is selected on each occurrence, identically or differently, from the group consisting of H, D, Cl, Br, I, $NAr_2$, $N(R^1)_2$, where $R^1$ is not equal to H, $C(=O)Ar$, $C(=O)R^1$, $BR^1$, $P(=O)Ar_2$, $PAr_2$, OAr, SAr, $S(=O)Ar$, $S(=O)_2Ar$, $Si(R^1)_3$, a straight-chain alkyl or alkoxy group having 1 to 40 C atoms or a branched or cyclic alkyl or alkoxy group having 3 to 40 C atoms or an alkenyl or alkynyl group having 2 to 40 C atoms, each of which may be substituted by one or more radicals $R^1$, where in each case one or more non-adjacent CH₂ groups may be replaced by R¹C=CR¹, C≡C, Si(R¹)₂, C=NR¹, P(=O)(R¹), NR¹, O, S or CONR¹ and where one or more H atoms may be replaced by D, F, Cl, Br, I or CN, or an aromatic or heteroaromatic ring system having 5 to 60 aromatic ring atoms, which may in each case be substituted by one or more radicals R¹; two or more adjacent substituents R here may optionally form a monocyclic or polycyclic, aliphatic, aromatic or heteroaromatic ring system, which may be substituted by one or more radicals R¹;

Ar is on each occurrence, identically or differently, an aromatic or heteroaromatic ring system having 5-30 aromatic ring atoms, which may be substituted by one or more radicals R¹; two radicals Ar here which are bonded to the same N atom or P atom may also be bridged to one another by a single bond or a bridge selected from N(R¹), C(R¹)₂, O, S or BR¹;

R¹ is selected on each occurrence, identically or differently, from the group consisting of H, D, F, Cl, Br, I, CN, NO₂, N(R²)₂, P(=O)(R²)₂, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals R², where one or more non-adjacent CH₂ groups may be replaced by R²C=CR², C≡C, Si(R²)₂, C=NR², P(=O)(R²), SO, SO₂, NR², O, S or CONR² and where one or more H atoms may be replaced by D, F, Cl, Br, I or CN, an aromatic or heteroaromatic ring system having 5 to 60 aromatic ring atoms, which may in each case be substituted by one or more radicals R²; two or more adjacent substituents R¹ here may optionally form a monocyclic or polycyclic, aliphatic ring system, which may be substituted by one or more radicals R²;

R² is selected on each occurrence, identically or differently, from the group consisting of H, D, F, CN, an aliphatic hydrocarbon radical having 1 to 20 C atoms, an aromatic or heteroaromatic ring system having 5 to 30 aromatic ring atoms, in which one or more H atoms may be replaced by D, F, Cl, Br, I or CN, where two or more adjacent substituents R² may form a mono- or polycyclic, aliphatic ring system with one another;

n is 0, 1, 2, 3, 4 or 5, with the proviso that L is not present if n=0 and furthermore with the proviso that, for n≥1, L is in each case bonded to the benzene skeleton instead of a radical R and the corresponding group R is thus not present;

with the proviso that the following compounds are excluded from the invention:

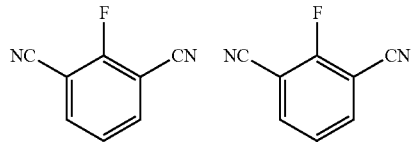

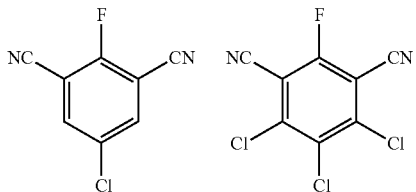

-continued

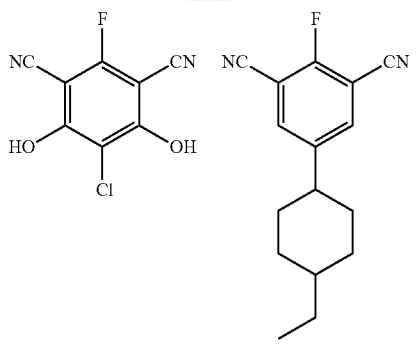

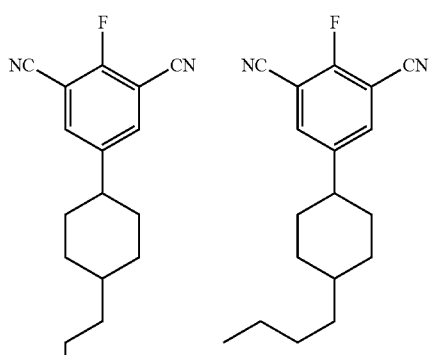

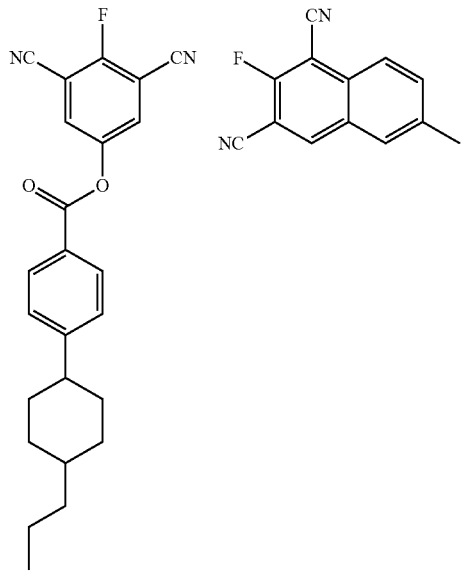

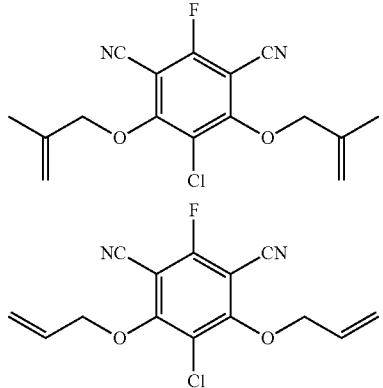

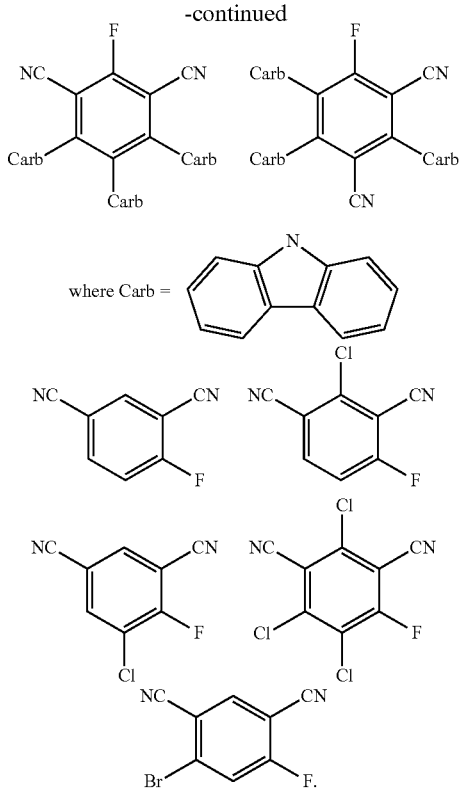

An aryl group in the sense of this invention contains 6 to 60 C atoms; a heteroaryl group in the sense of this invention contains 2 to 60 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed (anellated) aryl or heteroaryl group, for example naphthalene, anthracene, phenanthrene, quinoline, isoquinoline, etc. Aromatic groups which are linked to one another by a single bond, such as, for example, biphenyl, are, by contrast, not referred to as aryl or heteroaryl group, but instead as aromatic ring system.

An aromatic ring system in the sense of this invention contains 6 to 60 C atoms in the ring system. A heteroaromatic ring system in the sense of this invention contains 2 to 60 C atoms and at least one heteroatom in the ring system, with the proviso that the sum of C atoms and heteroatoms is at least 5. The heteroatoms are preferably selected from N, O and/or S. For the purposes of this invention, an aromatic or heteroaromatic ring system is intended to be taken to mean a system which does not necessarily contain only aryl or heteroaryl groups, but instead in which, in addition, a plurality of aryl or heteroaryl groups may be connected by a non-aromatic unit, such as, for example, a C, N or O atom. Thus, for example, systems such as fluorene, 9,9'-spirobifluorene, 9,9-diarylfluorene, triarylamine, diaryl ether, stilbene, etc., are also intended to be taken to be aromatic ring systems for the purposes of this invention, as are systems in which two or more aryl groups are connected, for example, by a short alkyl group.

For the purposes of the present invention, an aliphatic hydrocarbon radical or an alkyl group or an alkenyl or alkynyl group, which may contain ≥1 to 40 C atoms and in which, in addition, individual H atoms or $CH_2$ groups may be substituted by the above-mentioned groups, is preferably taken to mean the radicals methyl, ethyl, n-propyl, i-propyl, n-butyl, i-butyl, s-butyl, t-butyl, 2-methylbutyl, n-pentyl, s-pentyl, neopentyl, cyclopentyl, n-hexyl, neohexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl or octynyl. An alkoxy group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy and 2,2,2-trifluoroethoxy. A thioalkyl group having 1 to 40 C atoms is taken to mean, in particular, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio. In general, alkyl, alkoxy or thioalkyl groups in accordance with the present invention may be straight-chain, branched or cyclic, where one or more non-adjacent $CH_2$ groups may be replaced by the above-mentioned groups; furthermore, one or more H atoms may also be replaced by D, F, Cl, Br, I, CN or $NO_2$, preferably F, Cl or CN, further preferably F or CN, particularly preferably CN.

An aromatic or heteroaromatic ring system having 5-60 aromatic ring atoms, which may also in each case be substituted by the above-mentioned radicals $R^2$ or a hydrocarbon radical and which may be linked via any desired positions on the aromatic or heteroaromatic ring system, is taken to mean, in particular, groups derived from benzene, naphthalene, anthracene, benzanthracene, phenanthrene, pyrene, chrysene, perylene, fluoranthene, naphthacene, pentacene, benzopyrene, biphenyl, biphenylene, terphenyl, triphenylene, fluorene, spirobifluorene, dihydrophenanthrene, dihydropyrene, tetrahydropyrene, cis- or trans-indenofluorene, cis- or trans-indenocarbazole, cis- or trans-indolocarbazole, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, hexaazatriphenylene, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole or groups derived from combination of these systems.

In an embodiment of the invention, compounds of the formula (1), (2) and (3) in which R stands, identically or differently, for carbazole or for a substituted carbazole, each of which is bonded to the skeleton via the nitrogen atom, are excluded from the invention.

In a preferred embodiment of the invention, n=0, 1, 2 or 3, particularly preferably 0, 1 or 2, very particularly preferably 0 or 1, in particular n=0. L is a single bond or a divalent group for n=1, a trivalent group for n=2, etc.

In a further preferred embodiment of the invention, L stands for a single bond, NR, BR, P(=O)R, a straight-chain alkylene or alkylidene group having 1 to 10 C atoms or a branched or cyclic alkylene or alkylidene group having 3 to 10 C atoms, which may be substituted by in each case one or more radicals R, where one or more non-adjacent CH$_2$ groups may be replaced by —RC=CR—, —C≡C—, Si(R)$_2$, C=O, —O—, —S— or —CONR— and where one or more H atoms may be replaced by D or F, or an aromatic or heteroaromatic ring system having 5 to 24 aromatic ring atoms, which may be substituted by one or more radicals R. L particularly preferably stands for a single bond, NR, a straight-chain alkylene or alkylidene group having 1 to 6 C atoms or a branched or cyclic alkylene or alkylidene group having 3 to 6 C atoms, where one or more non-adjacent CH$_2$ groups may be replaced by —O—, or an aromatic or heteroaromatic ring system having 5 to 18 aromatic ring atoms, which may be substituted by one or more radicals R. As described above, the group L is not present for n=0, and, for n≥1, the group L is in each case bonded to the benzene skeleton instead of one of the radicals R. For n=2, preferred groups L may furthermore also be selected from N, B or P=O.

Preferred embodiments of the compounds of the formula (1) are the compounds of the following formulae (1a) to (1e) for n=0 and the compounds of the following formulae (1f) to (1h) for n≥1. Preferred embodiments of the compounds of the formula (2) are the compounds of the following formulae (2a) to (2g) for n=0 and the compounds of the following formulae (2h) to (2l) for n≥1. Preferred embodiments of the compounds of the formula (3) are the compounds of the following formulae (3a) to (3f) for n≥1.

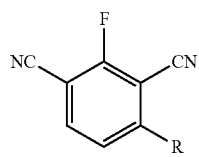

formula (1a)

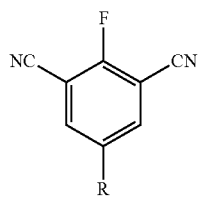

formula (1b)

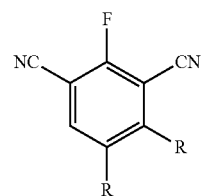

formula (1c)

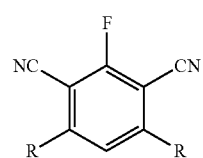

formula (1d)

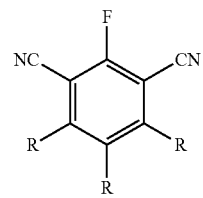

formula (1e)

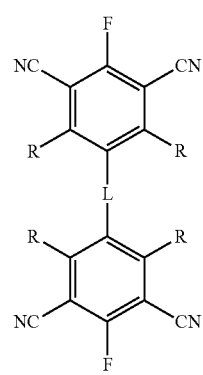

formula (1f)

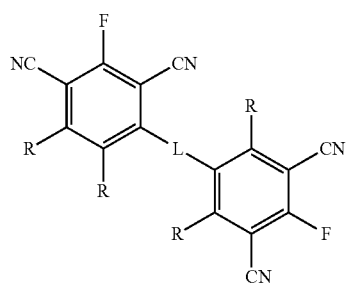

formula (1g)

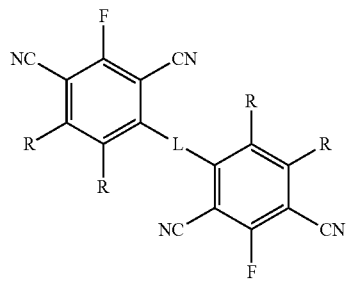

formula (1h)

formula (2a)

formula (2b)

formula (2c)

formula (2d)

formula (2e)

formula (2f)

formula (2g)

formula (2h)

formula (2i)

formula (2j)

formula (2k)

formula (2k)

formula (2l)

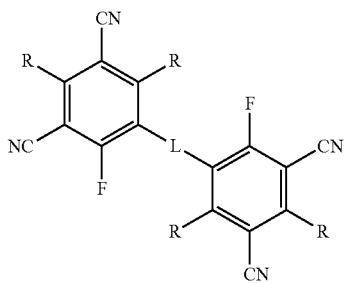

formula (3a)

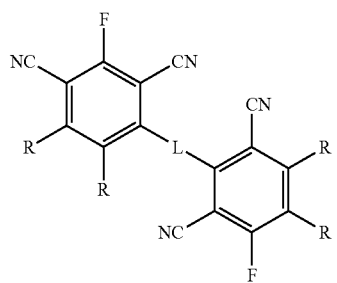

formula (3b)

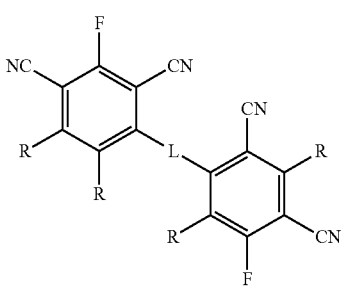

formula (3c)

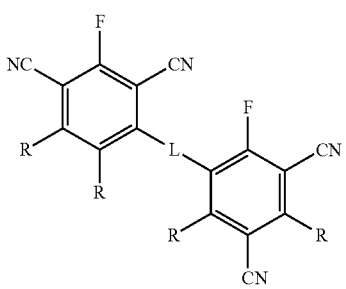

formula (3d)

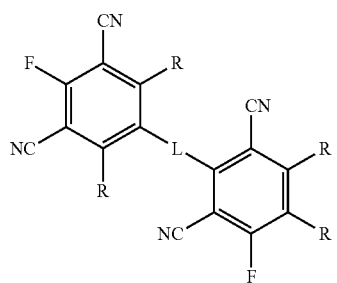

formula (3e)

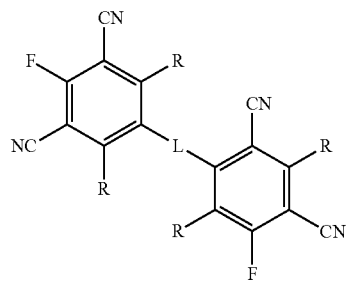

formula (3f)

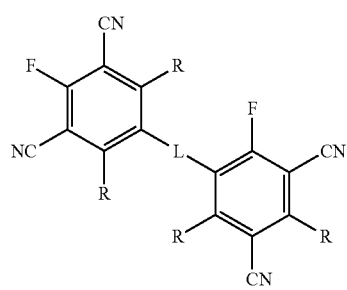

where R and L have the meanings given above. In the monomeric structures, i.e. the structures of the formulae (1a) to (1e) and (2a) to (2g), the radicals R are preferably not equal to H or D.

As mentioned above, a plurality of adjacent radicals R may also form a ring with one another, so that, for example through the formation of a condensed-on benzo group, a naphthalene forms overall. Preference is also given to the formation of a condensed-on aliphatic ring, where the ring system preferably has in total 5 to 7 ring atoms. Preferred condensed-on rings which form through ring formation of adjacent radicals R are furthermore the structures of the following formula (4), formula (4)

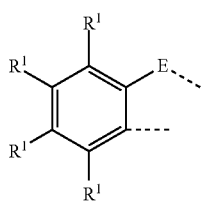

where $R^1$ has the meanings given above, the dashed bonds indicate the linking of the group to the benzene skeleton and furthermore:

E is selected from the group consisting of $C(R^1)_2$, $NR^1$, O, S, $BR^1$ or $Si(R^1)_2$, preferably $NR^1$, O or S.

Preferred embodiments of the formula (1) which contain a group of the formula (4) are the compounds of the following formulae (5a) and (5b), and preferred embodiments of the formula (2) which contain a group of the formula (4) are the compounds of the following formulae (6a) and (6b),

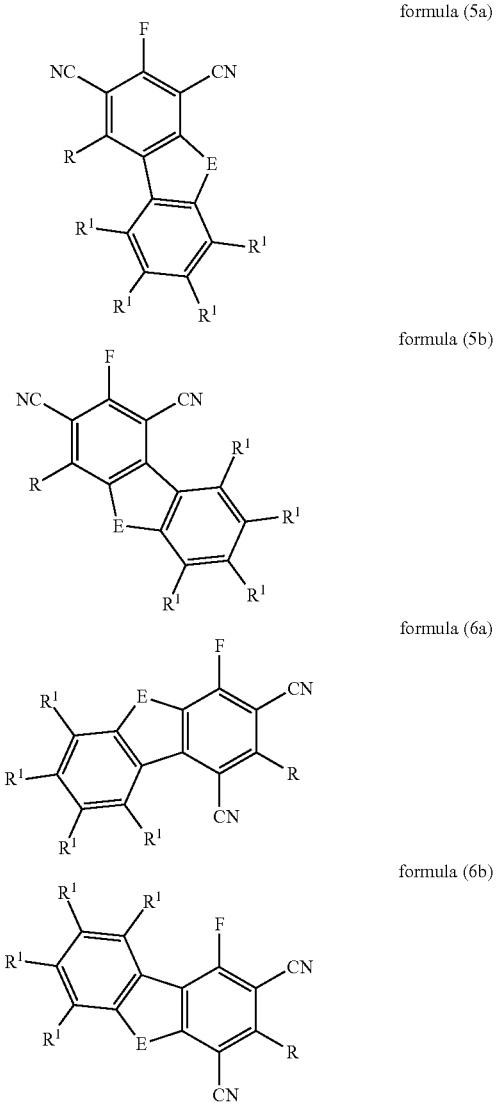

formula (5a)

formula (5b)

formula (6a)

formula (6b)

where the symbols used have the meanings given above,

In each case here, only structures where n=0 are depicted. Entirely correspondingly, structures may also contain units of the formula (4) where n≥1.

Preferred radicals R are selected on each occurrence, identically or differently, from the group consisting of H, NAr$_2$, C(=O)Ar, P(=O)Ar$_2$, PAr$_2$, Si(R$^1$)$_3$, a straight-chain alkyl group having 1 to 10 C atoms or a branched or cyclic alkyl group having 3 to 10 C atoms or an alkenyl group having 2 to 10 C atoms, each of which may be substituted by one or more radicals R$^1$, where in each case one or more non-adjacent CH$_2$ groups may be replaced by R$^1$C=CR$^1$ or O and where one or more H atoms may be replaced by F, an aromatic or heteroaromatic ring system having 5 to 40 aromatic ring atoms, which may in each case be substituted by one or more radicals R$^1$; two or more adjacent substituents R here may optionally form a monocyclic or polycyclic, aliphatic, aromatic or heteroaromatic ring system, which may be substituted by one or more radicals R$^1$.

Particularly preferred radicals R are selected on each occurrence, identically or differently, from the group consisting of H, NAr$_2$, a straight-chain alkyl group having 1 to 6 C atoms or a branched or cyclic alkyl group having 3 to 8 C atoms, each of which may be substituted by one or more radicals R$^1$, an aromatic or heteroaromatic ring system having 5 to 24 aromatic ring atoms, which may in each case be substituted by one or more radicals R$^1$; two or more adjacent substituents R here may optionally form a monocyclic or polycyclic, aliphatic, aromatic or heteroaromatic ring system, which may be substituted by one or more radicals R$^1$.

Preferred groups Ar are selected from aromatic or heteroaromatic ring systems having 5 to 24 aromatic ring atoms, particularly preferably having 5 to 18 aromatic ring atoms, which may in each case be substituted by one or more radicals R$^1$. Ar here preferably contains no condensed aryl or heteroaryl groups in which more than two six-membered rings are condensed directly onto one another. In particular, it is preferred if Ar contain no condensed aryl or heteroaryl group in which two or more six-membered rings are condensed directly onto one another.

If R stands for an alkyl group, it is preferred if this alkyl group has no benzylic protons, i.e. if no hydrogen atom is bonded to the carbon atom which is bonded directly to the benzene ring. This is achieved, for example, through the use of tertiary alkyl groups, such as, for example, tert-butyl.

If R stands for a group Si(R$^1$)$_3$, R$^1$ in this group preferably stands, identically or differently on each occurrence, for an alkyl group having 1 to 10 C atoms, particularly preferably having 1 to 4 C atoms.

In a preferred embodiment of the invention, at least one of the radicals R is an aromatic or heteroaromatic ring system or a diarylamino group NAr$_2$.

If R stands for an aromatic or heteroaromatic ring system, this preferably has, as described above, 5 to 24 aromatic ring atoms and may be substituted by one or more radicals R$^1$. Preferred aromatic or heteroaromatic groups R are selected from benzene, biphenyl, in particular ortho-, meta- or para-biphenyl, terphenyl, in particular ortho-, meta-, para- or branched terphenyl, quaterphenyl, in particular ortho-, meta-, para- or branched quaterphenyl, 1-, 2-, 3- or 4-spirobifluorene, 1-, 2-, 3- or 4-fluorene, 1- or 2-naphthyl, pyrrole, furan, thiophene, indole, benzofuran, benzothiophene, carbazole, azacarbazole, dibenzofuran, dibenzothiophene, pyridine, pyrimidine, pyrazine, pyridazine, triazine, imidazole, benzimidazole, pyrazole, thiazole, oxazole, oxadiazole, triazole, phenanthrene, triphenylene or combinations of two or three of these groups, each of which may be substituted by one or more radicals R$^1$.

If the radical R is an aromatic or heteroaromatic ring system, the compound preferably contains no condensed aryl or heteroaryl groups in which more than two six-membered rings are condensed directly onto one another. In particular, it is preferred if R contain no condensed aryl or heteroaryl group in which two or more six-membered rings are condensed directly onto one another. The compound of the formula (1), formula (2), formula (3) or the preferred embodiments particularly preferably does not contain condensed aryl or heteroaryl groups in which six-membered rings are condensed directly onto one another in any of the radicals R, R$^1$ or R$^2$.

Suitable and preferred aromatic ring systems R are the groups of the following formulae (7) to (14),

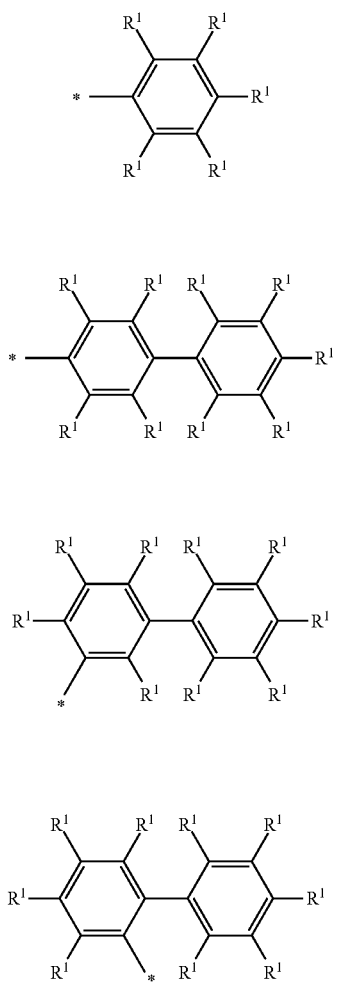
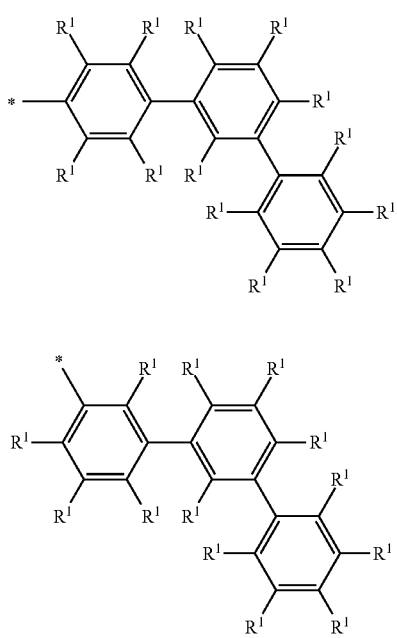
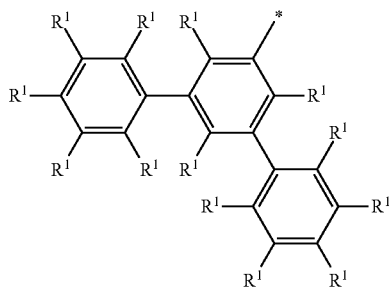
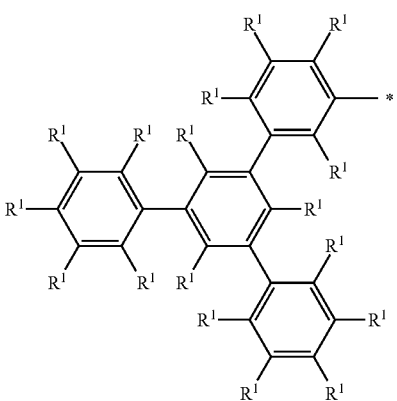
where the symbols used have the meanings given above and * indicates the position of the bonding of the group of the formula (7) to (14).
Suitable electron-deficient groups R are the groups of the following formulae (15) to (18),
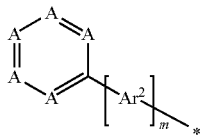
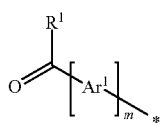
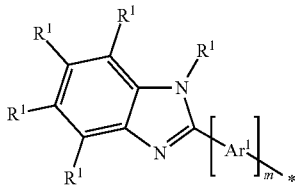

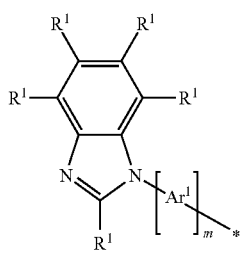

formula (18)

where R¹ has the meaning given above, * indicates the position of the bonding of the group of the formula (15) to (18) and furthermore:

A is on each occurrence, identically or differently, CR¹ or N, with the proviso that one, two or three groups A stand for N;

Ar¹ is, identically or differently on each occurrence, a divalent aromatic or heteroaromatic ring system having 5 to 16 aromatic ring atoms, which may be substituted by one or more radicals R¹;

m is 0 or 1.

Preferred groups of the formula (15) are the groups of the following formulae (15a) to (15g),

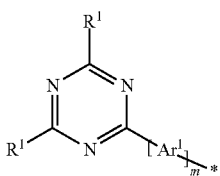

formula (15a)

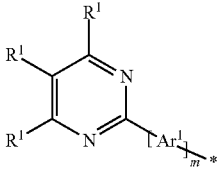

formula (15b)

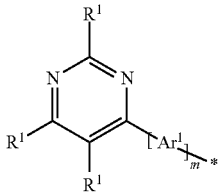

formula (15c)

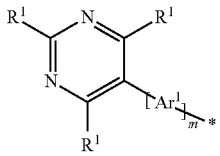

formula (15d)

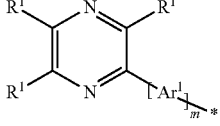

formula (15e)

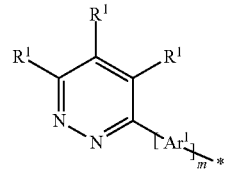

formula (15f)

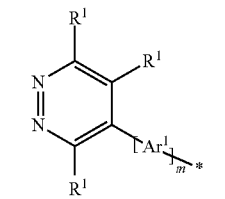

formula (15g)

where the symbols and indices used have the meanings given above.

The radical R¹ in formula (15a) preferably stands, identically or differently on each occurrence, for an aromatic or heteroaromatic ring system having 5 to 24 aromatic ring atoms, which may be substituted by one or more radicals R², in particular for phenyl, ortho-, meta- or para-biphenyl, ortho-, meta-, para- or branched terphenyl or ortho-, meta-, para- or branched quaterphenyl. These preferably have the same structures as shown above in the formulae (7) to (14), where radicals R² are bonded instead of radicals R¹.

The radical R¹ in the formulae (15b) to (15g) preferably stands, identically or differently on each occurrence, for H, D or an aromatic or heteroaromatic ring system having 5 to 24 aromatic ring atoms, which may be substituted by one or more radicals R², in particular for H or phenyl, ortho-, meta- or para-biphenyl, ortho-, meta-, para- or branched terphenyl or ortho-, meta-, para- or branched quaterphenyl. These preferably have the same structures as shown above in the formulae (7) to (14), where radicals R² are bonded instead of radicals R¹.

Furthermore preferably, at least one radical R in compounds of the formula (1), (2) or (3) is selected from the group consisting of triarylamine derivatives, carbazole derivatives, indenocarbazole derivatives, indolocarbazole derivatives, azacarbazole derivatives, indole derivatives, furan derivatives, benzofuran derivatives, dibenzofuran derivatives, thiophene derivatives, benzothiophene derivatives or dibenzothiophene derivatives, each of which may be substituted by one or more radicals R¹, or at least one substituent R stands for —NAr₂, where the two groups Ar may also be bridged to one another by a group selected from NR¹, O, S, C(R¹)₂, Si(R¹)₂ or BR¹. These groups are preferably selected from the groups of the following formulae (19) to (33),

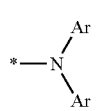

formula (19)

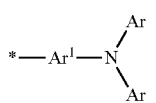

formula (20)

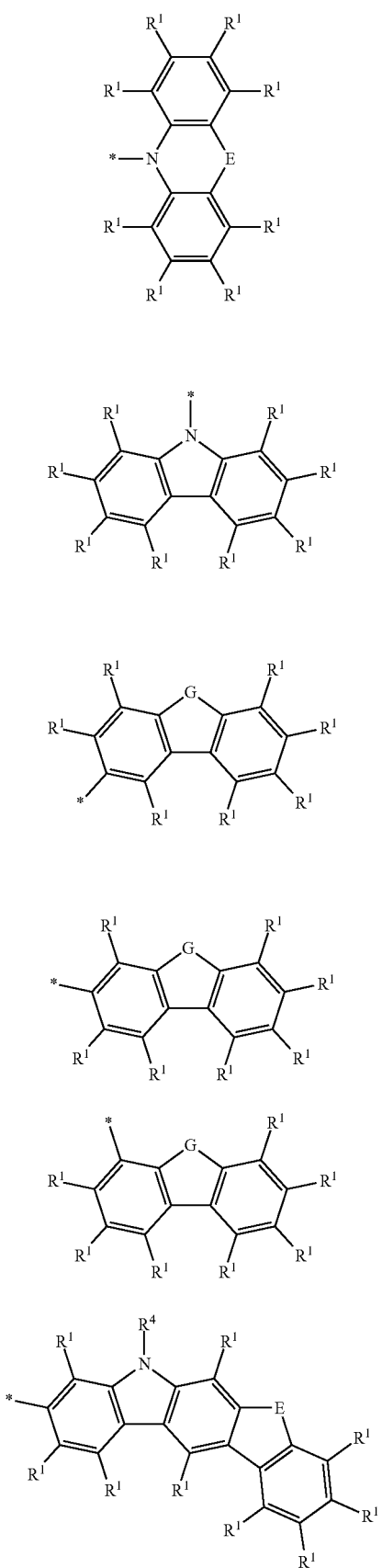
formula (21)
formula (22)
formula (23)
formula (24)
formula (25)
formula (26)
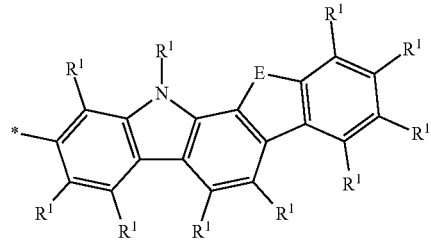
formula (27)
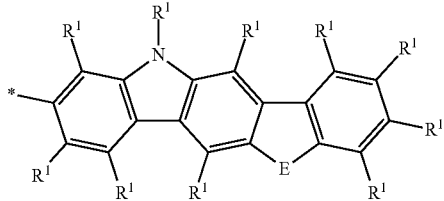
formula (28)
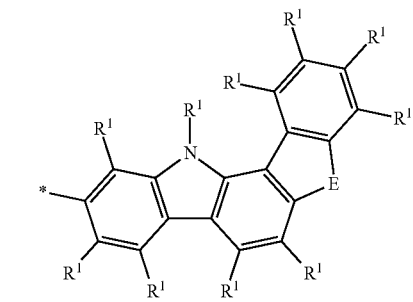
formula (29)
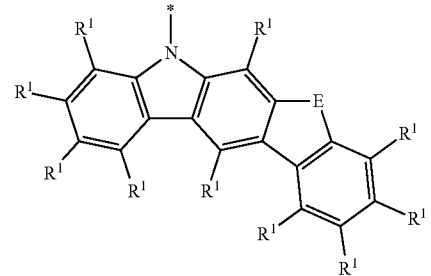
formula (30)
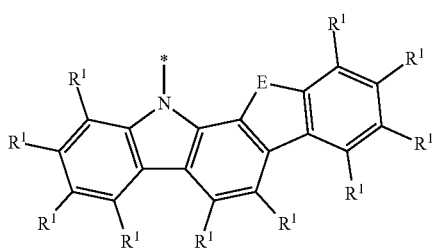
formula (31)
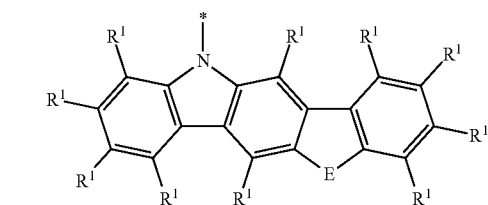
formula (32)

formula (33)

where the symbols used have the meanings given above and furthermore

G is selected from the group consisting of $NR^1$, O or S.

Furthermore preferably, one or two groups $CR^1$ in the above-mentioned structures may be replaced by N.

Preferred substituents $R^1$ on the above-mentioned structures are H, CN, alkyl groups having 1 to 10 C atoms, which are substituted by one or more radicals $R^2$, or aromatic or heteroaromatic ring systems having 5 to 24 aromatic ring atoms, which are substituted by one or more radicals $R^2$.

If E stands for $BR^1$, $R^1$ is preferably an aryl or heteroaryl group having 5 to 10 aromatic ring atoms, which may be substituted by one or more radicals $R^2$. A substituent $R^2$ other than H, for example an alkyl group, CN or an aryl group, is particularly preferably bonded to the aryl or heteroaryl group in both positions ortho to the link to the boron atom.

If E stands for $C(R^1)_2$ or $Si(R^1)_2$, $R^1$ is preferably, identically or differently on each occurrence, an alkyl group, an aryl group or a heteroaryl group, each of which may be substituted by one or more radicals $R^2$; the two groups $R^1$ here may also form a ring system with one another.

If E stands for $NR^1$, $R^1$ is preferably, identically or differently on each occurrence, an alkyl group, an aryl group or a heteroaryl group, in particular an aryl group, each of which may be substituted by one or more radicals $R^2$; the two groups $R^1$ here may also form a ring system with one another.

The above-mentioned preferred embodiments may be combined with one another as desired. In a particularly preferred embodiment of the invention, the above-mentioned preferences occur simultaneously.

Examples of preferred compounds in accordance with the embodiments described above are the compounds of the following structures 1 to 246.

11
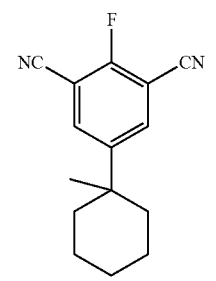
12
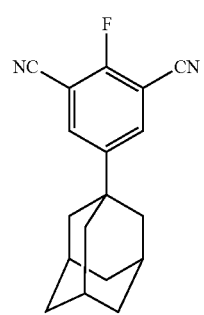
13
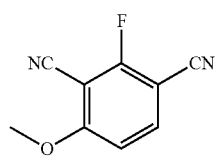
14
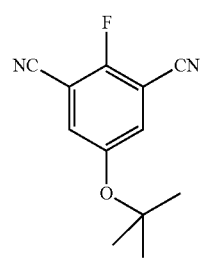
15
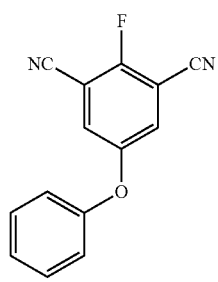
16
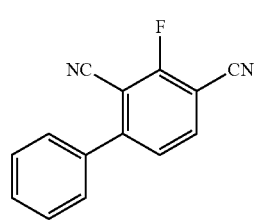
17
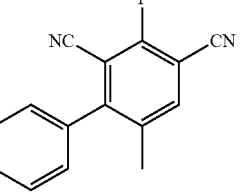
18
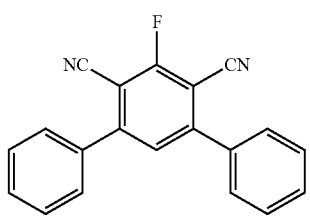
19
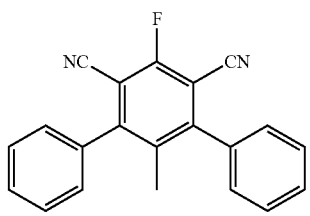
20
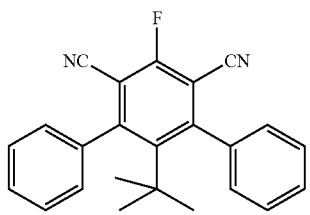
21
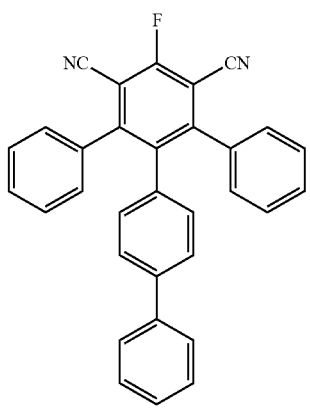
22
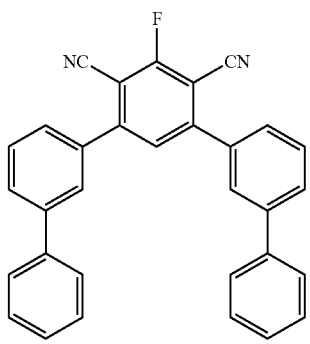

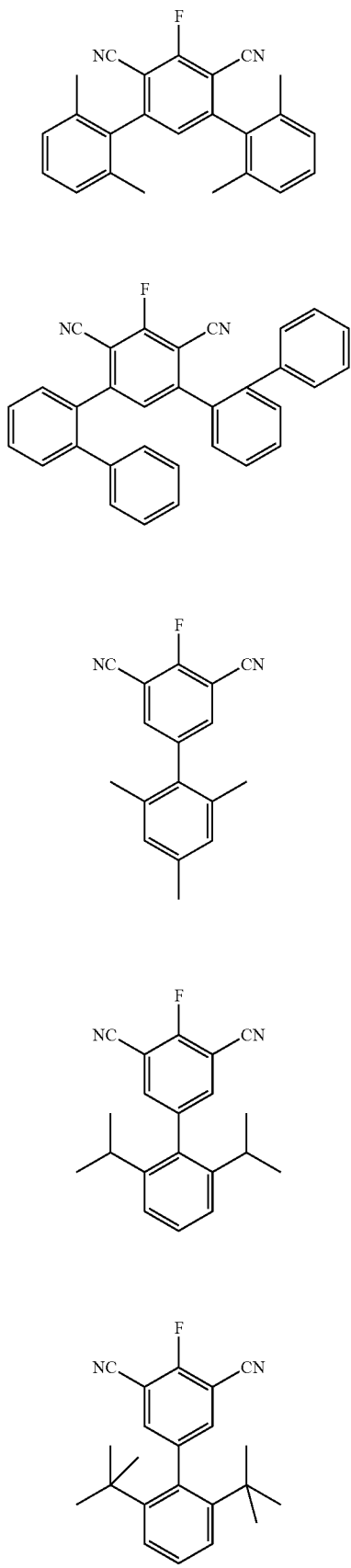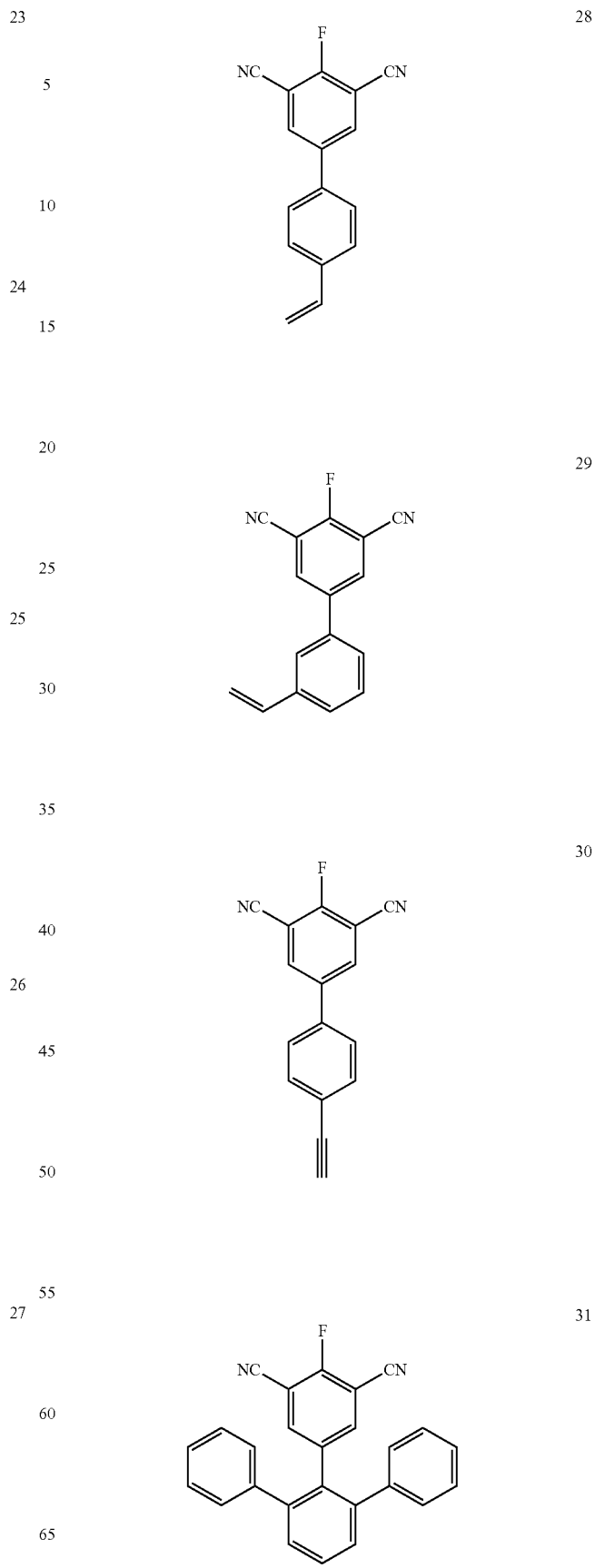

32
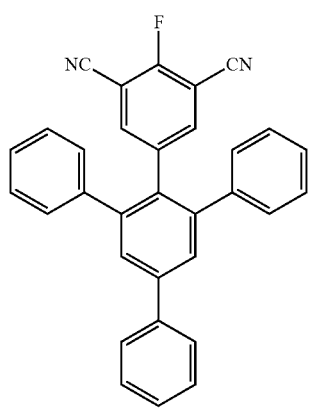
33
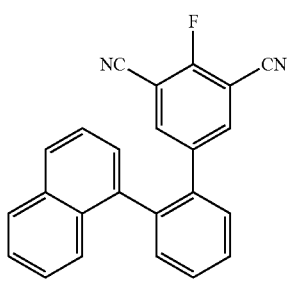
34
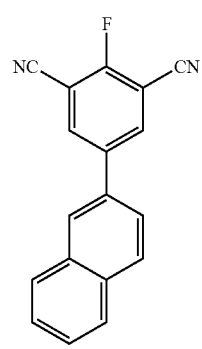
35
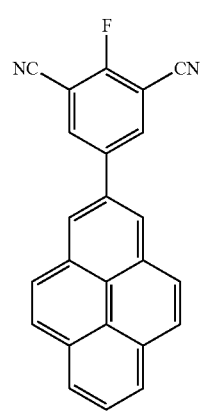
36
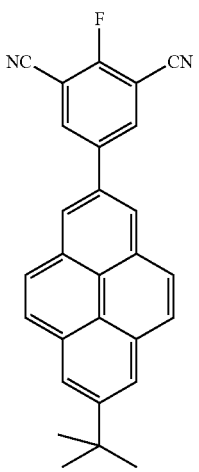
37
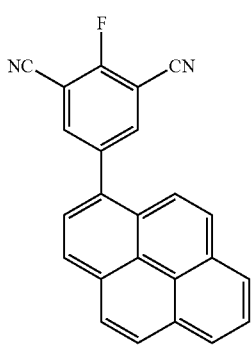
38
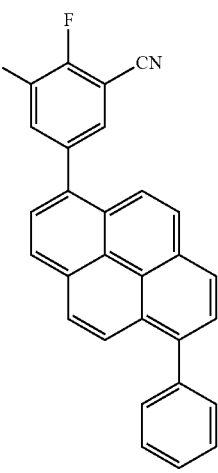

-continued

48
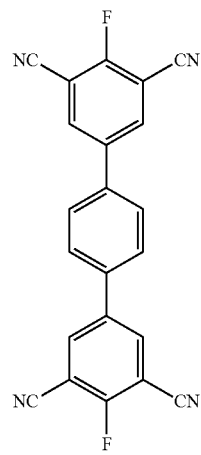
49
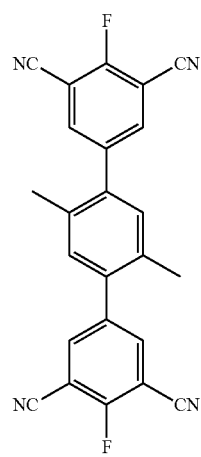
50
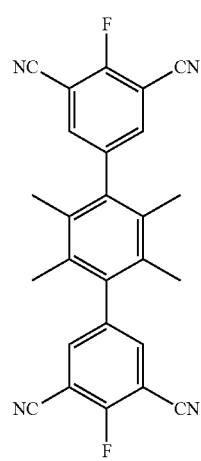
51
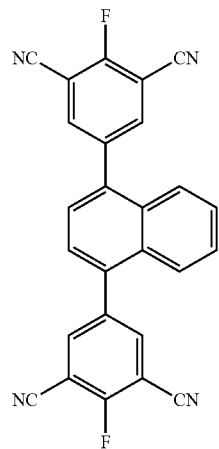
52
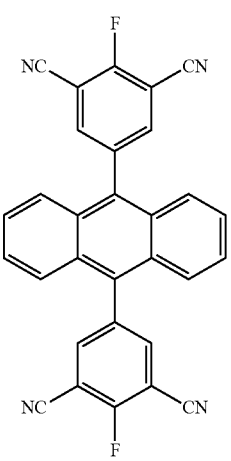
53
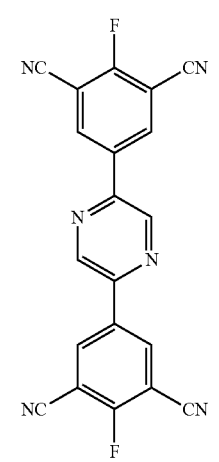

54
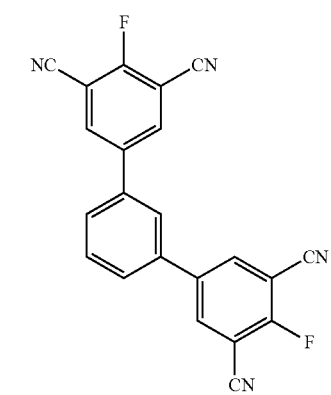
55
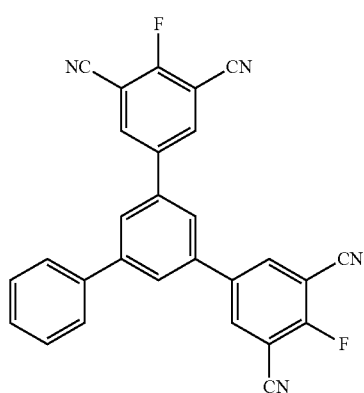
56
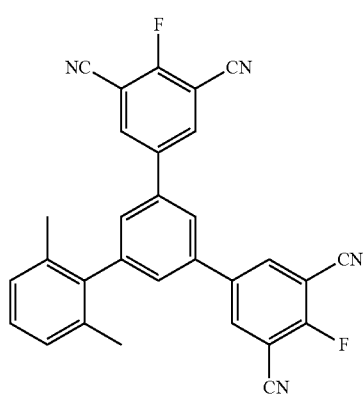
57
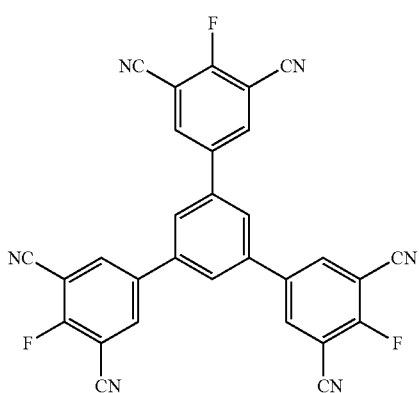
58
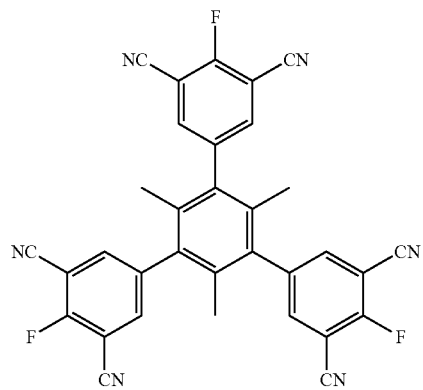
59
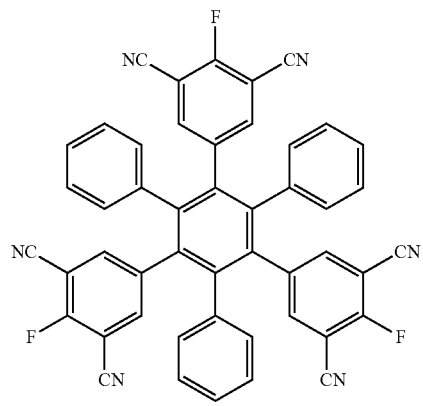
60
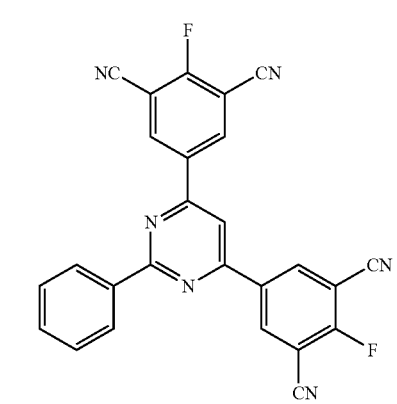
61
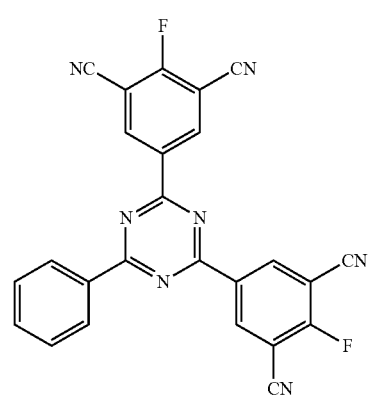

-continued
62
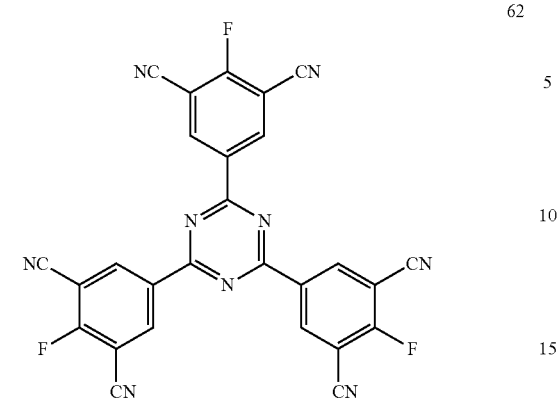
63
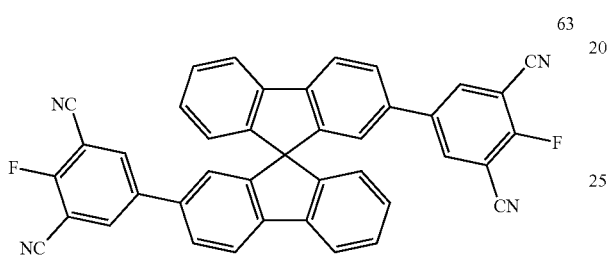
64
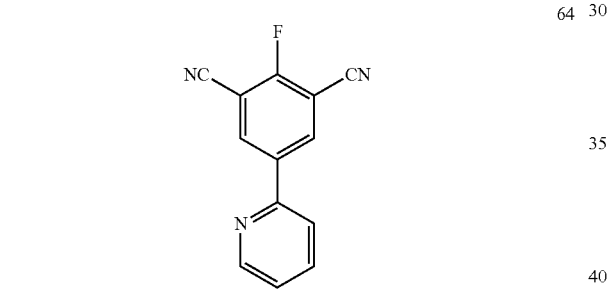
65
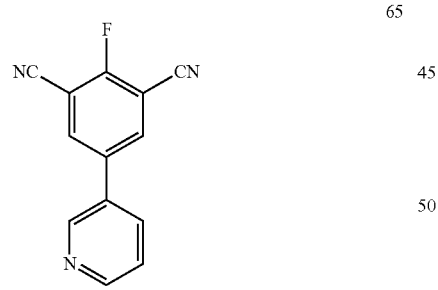
66
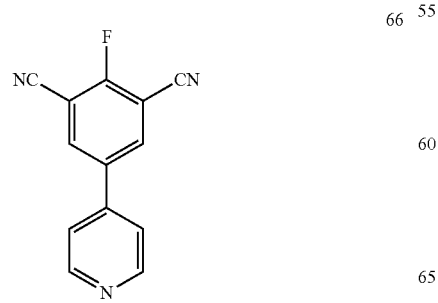
-continued
67
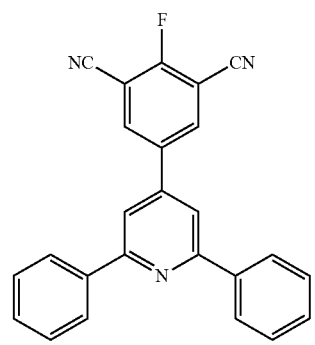
68
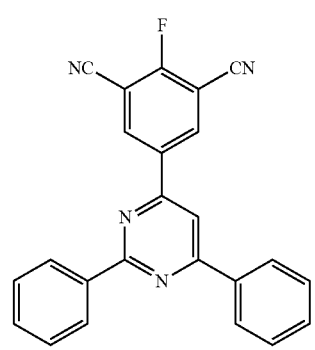
69
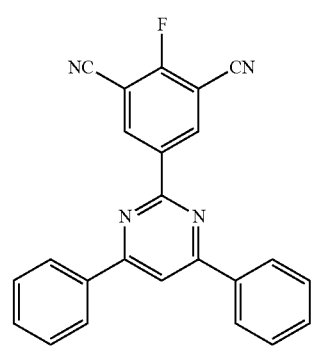
70
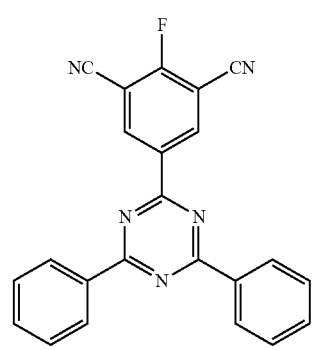

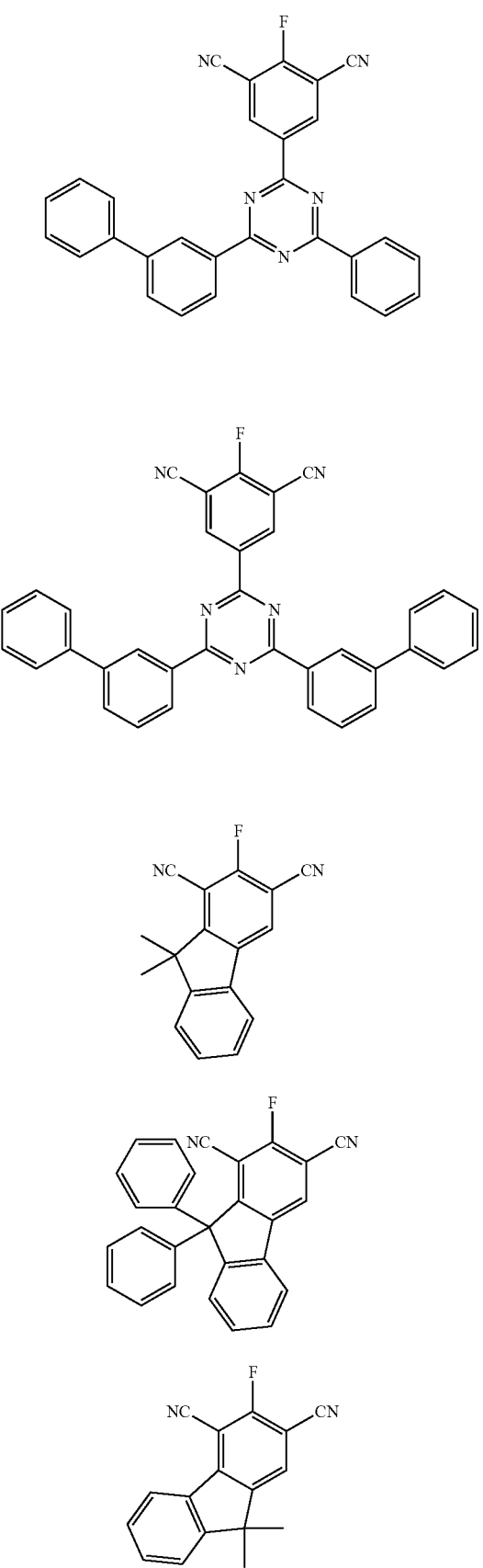
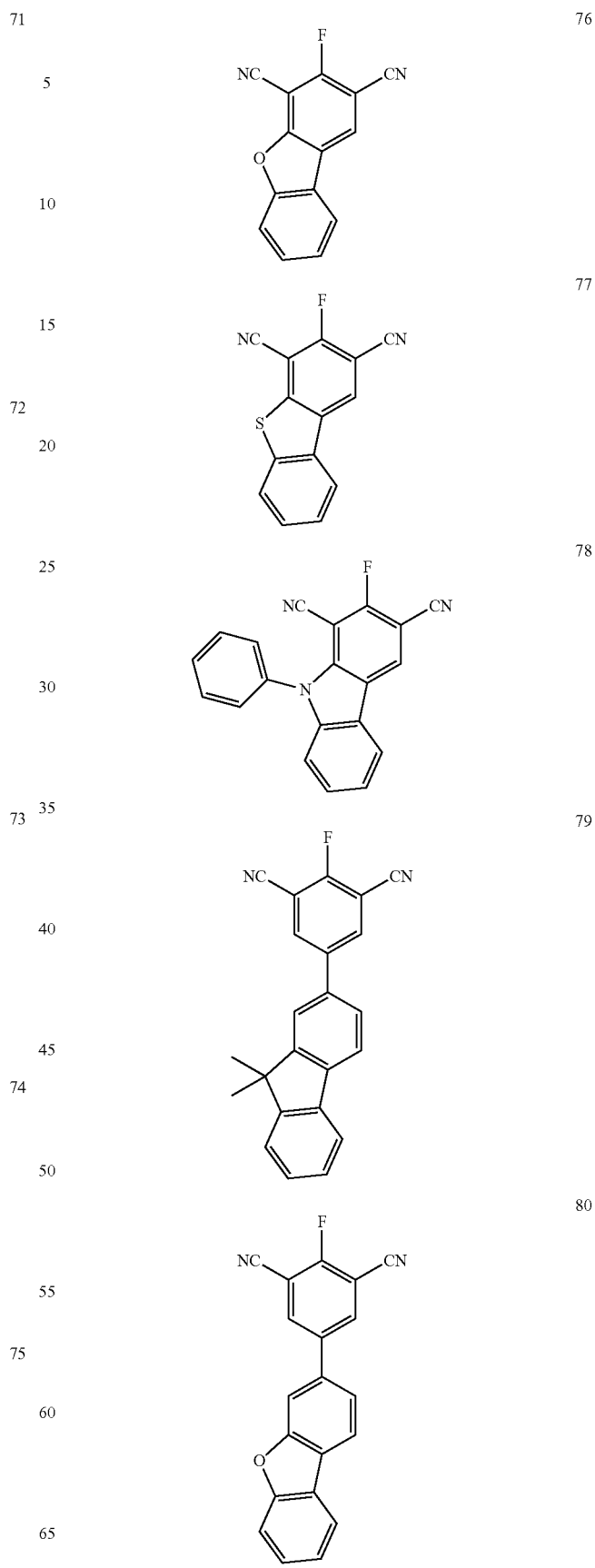

81
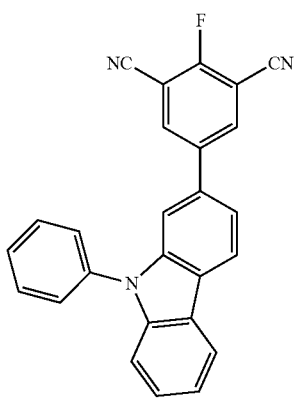
82
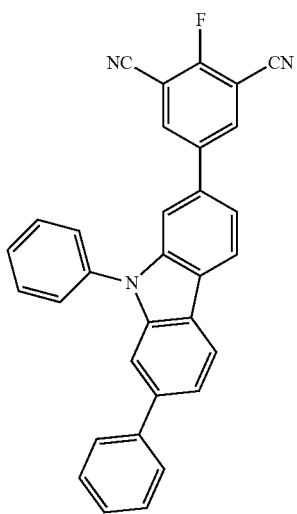
83
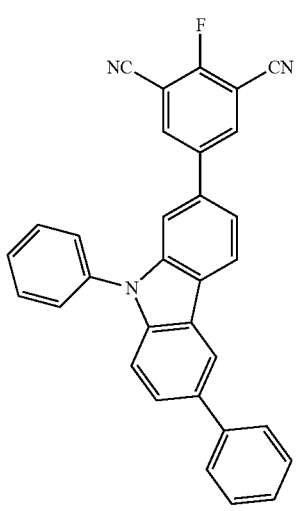
84
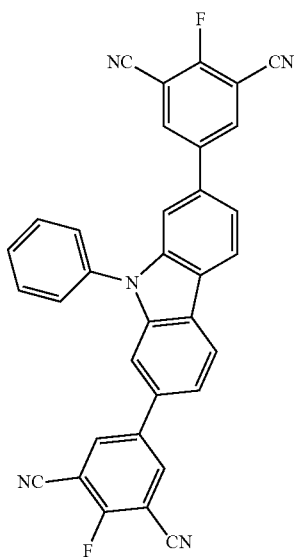
85
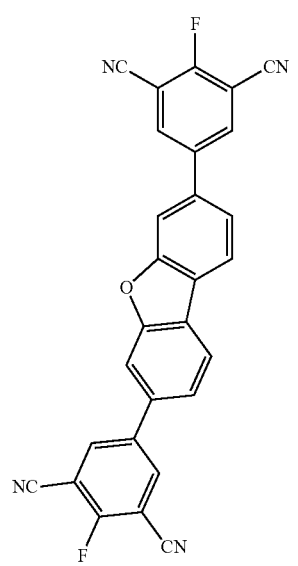
86
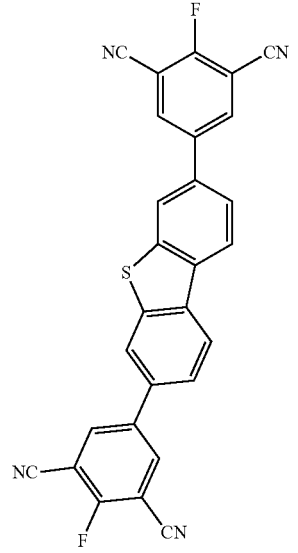

87 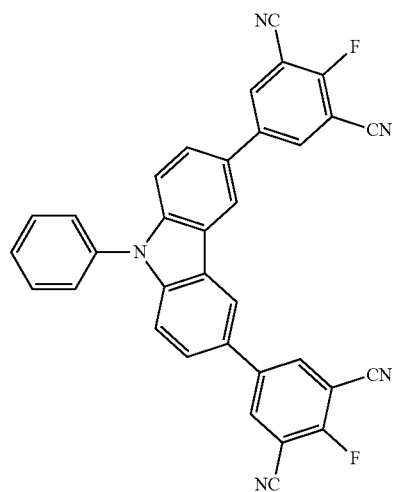
88 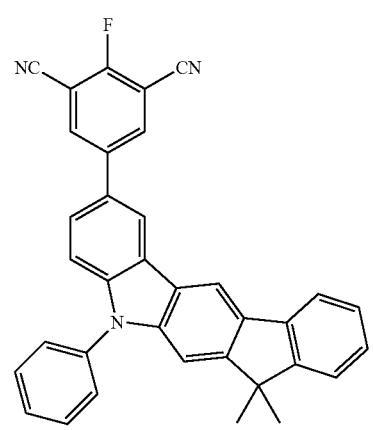
89 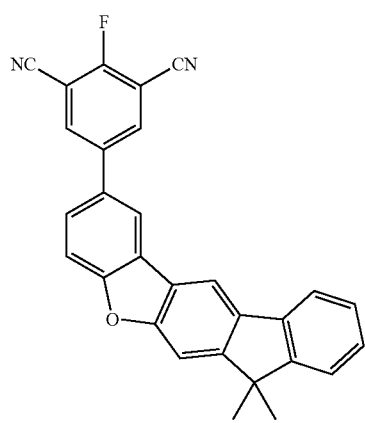
90 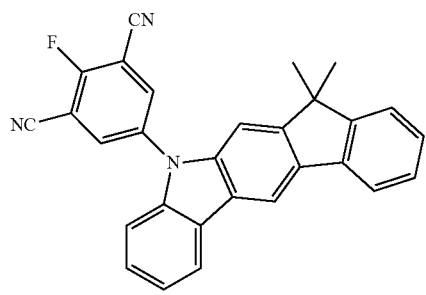
91 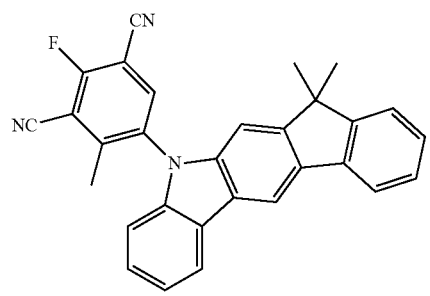
92 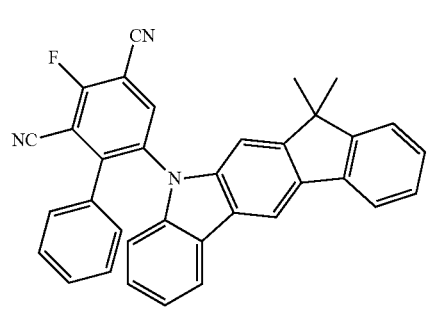
93 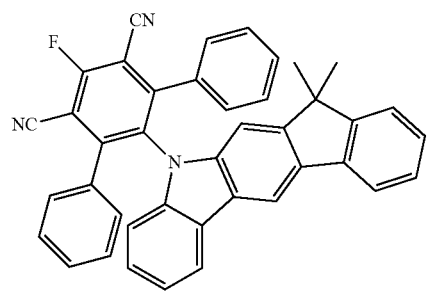
94 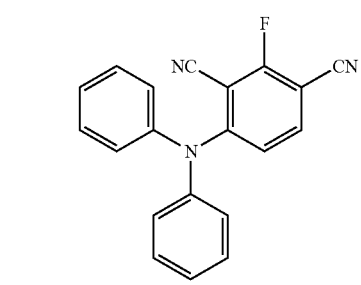
95 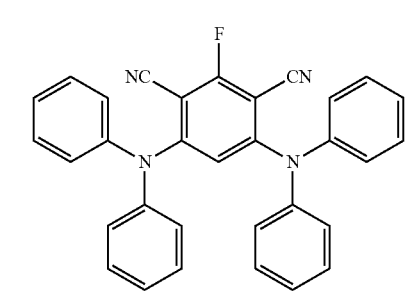

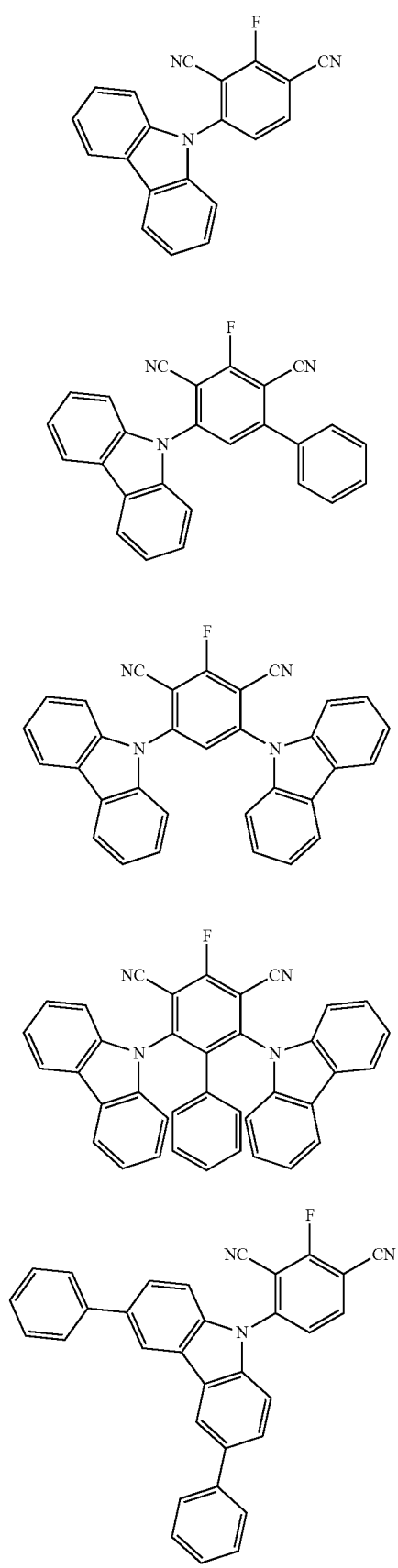
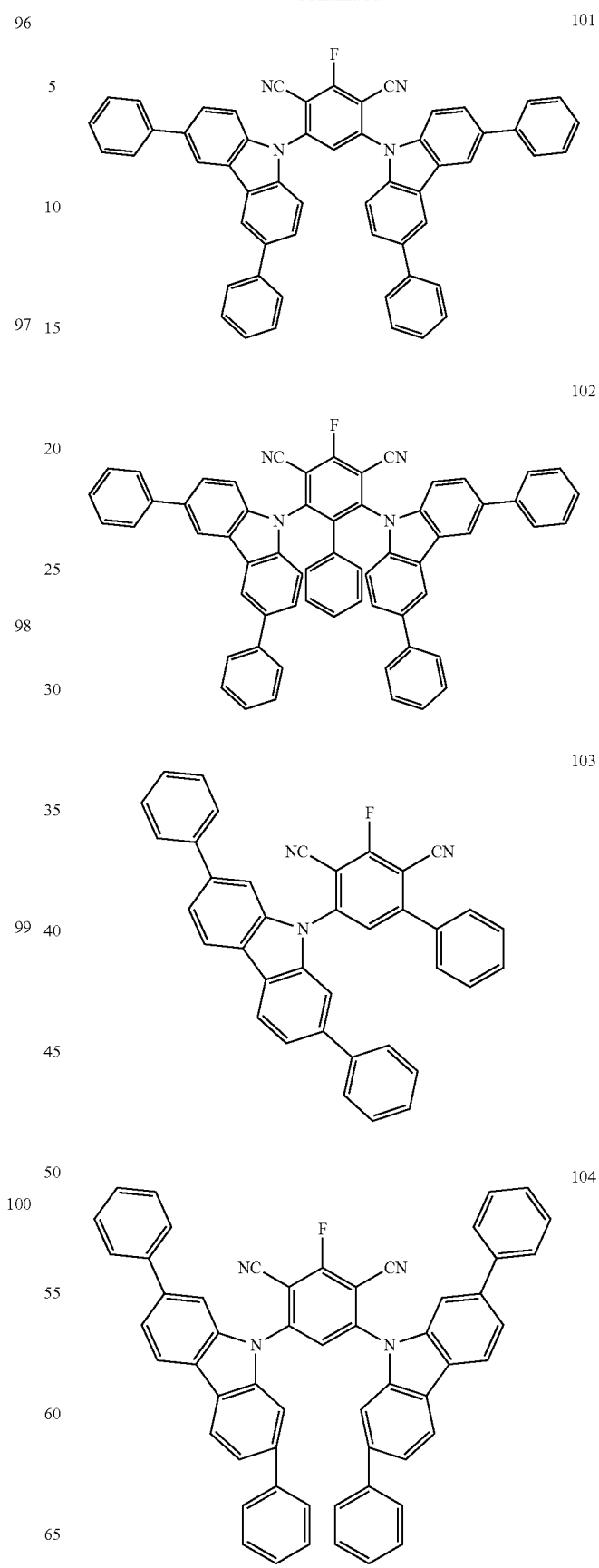

-continued
105
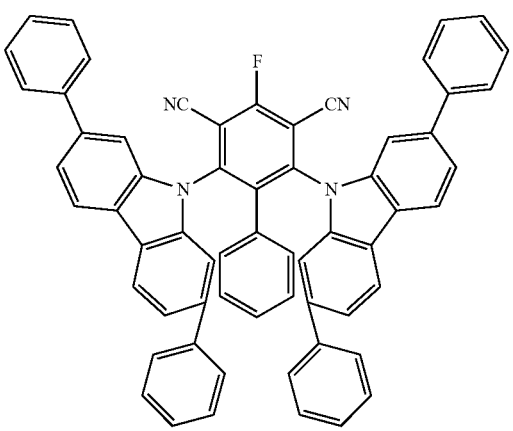
106
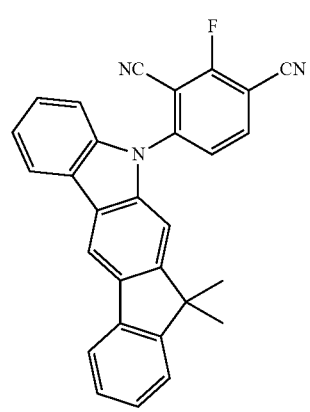
107
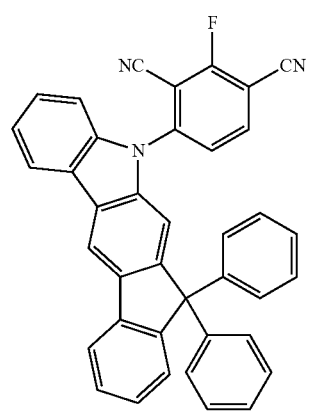
108
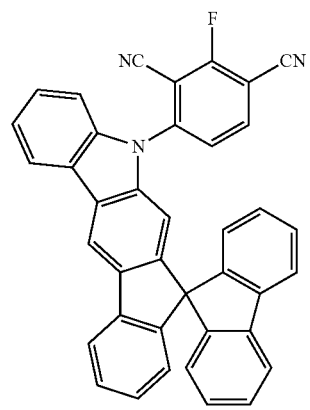
-continued
109
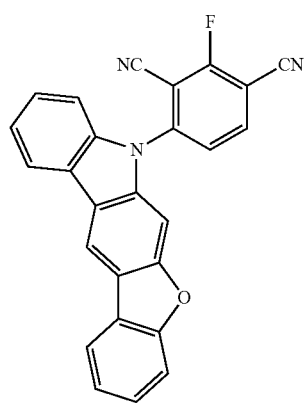
110
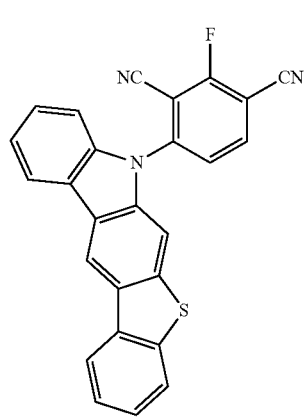
111
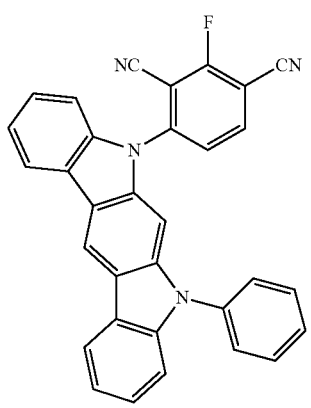
112
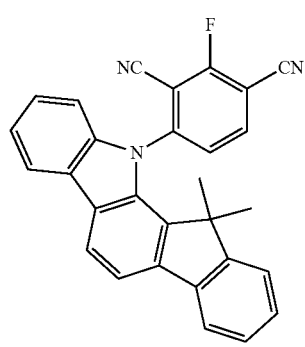

113
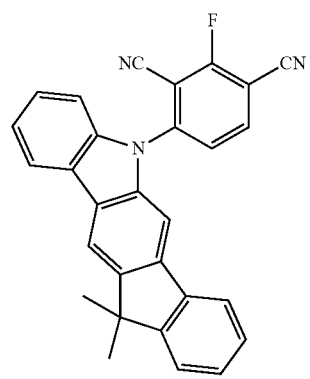
114
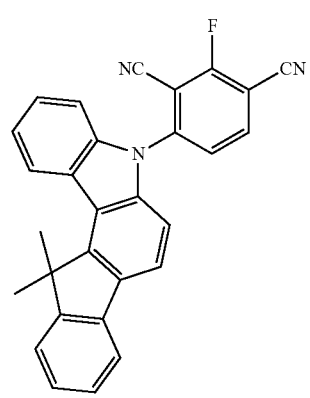
115
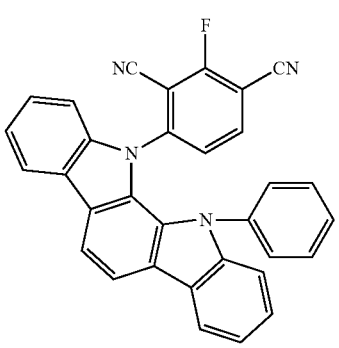
116
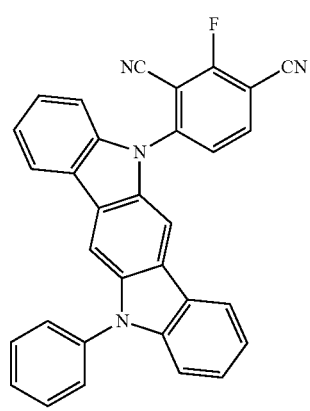
117
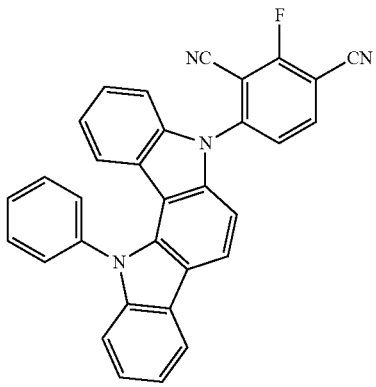
118
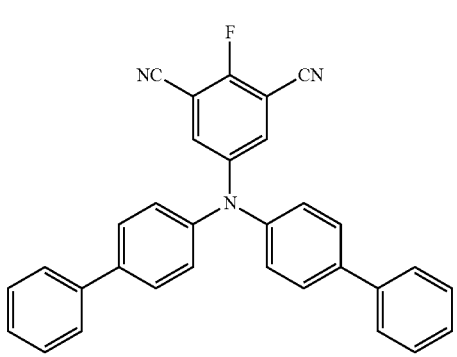
119
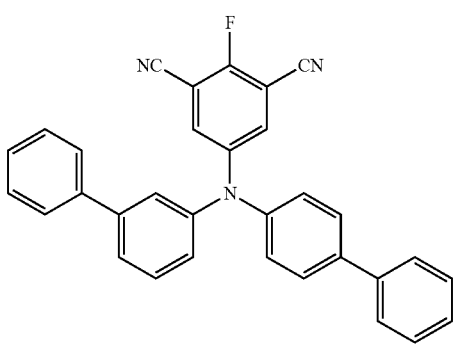
120
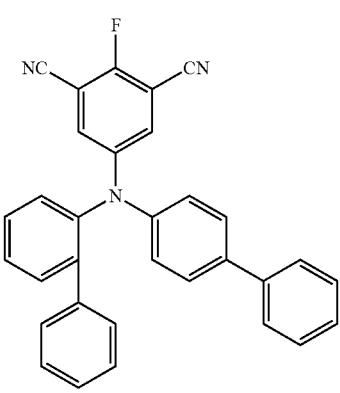

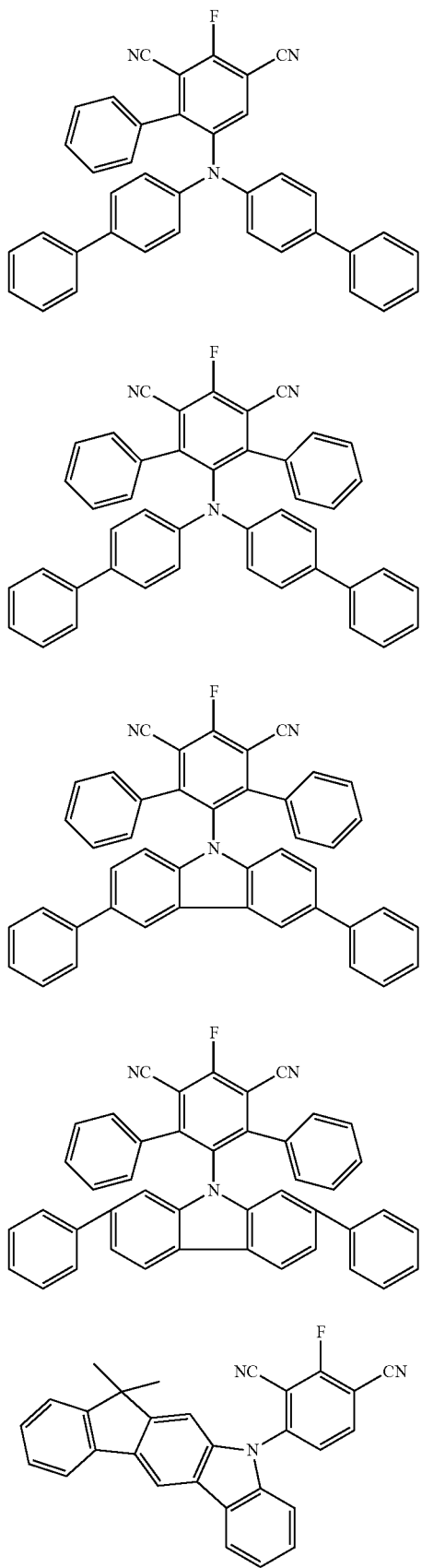
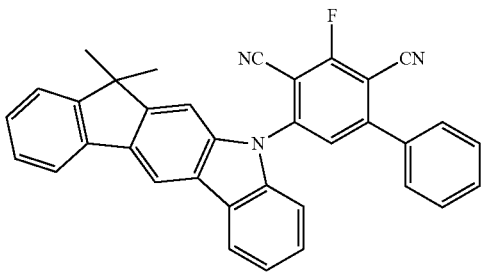
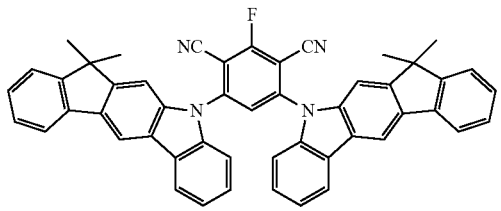
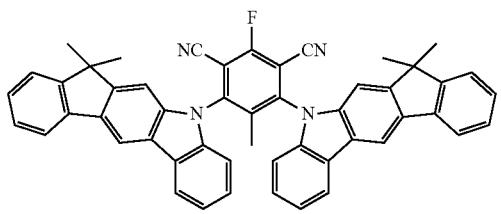
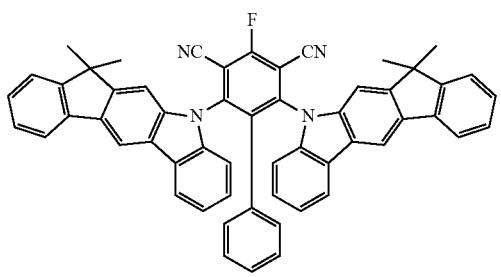
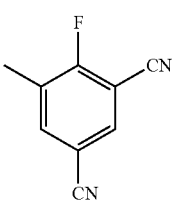
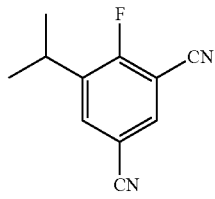
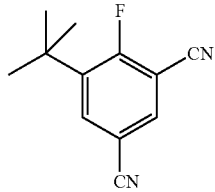

133 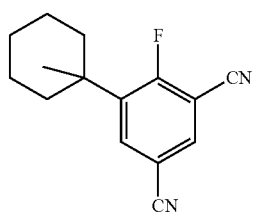
134 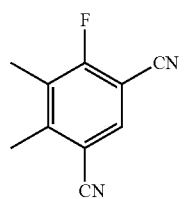
135 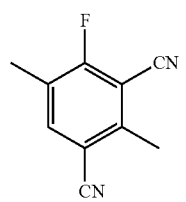
136 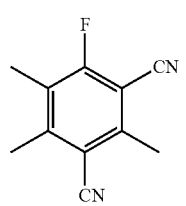
137 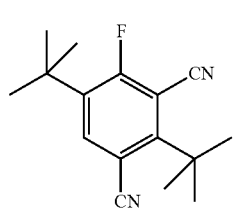
138 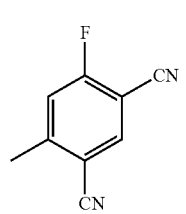
139 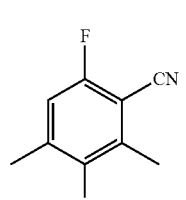
140 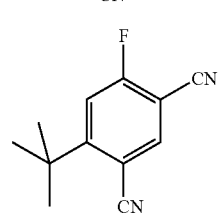
141 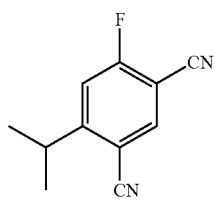
142 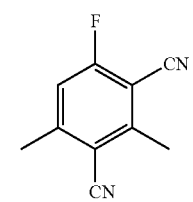
143 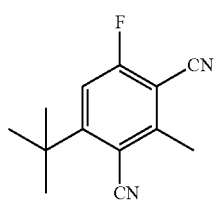
144 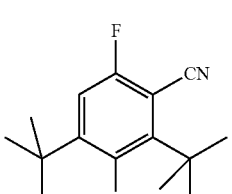
145 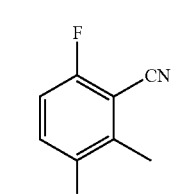
146 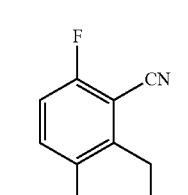
147 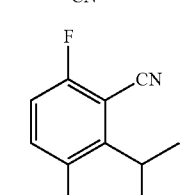
148 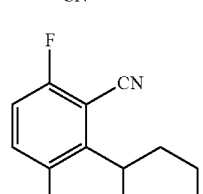

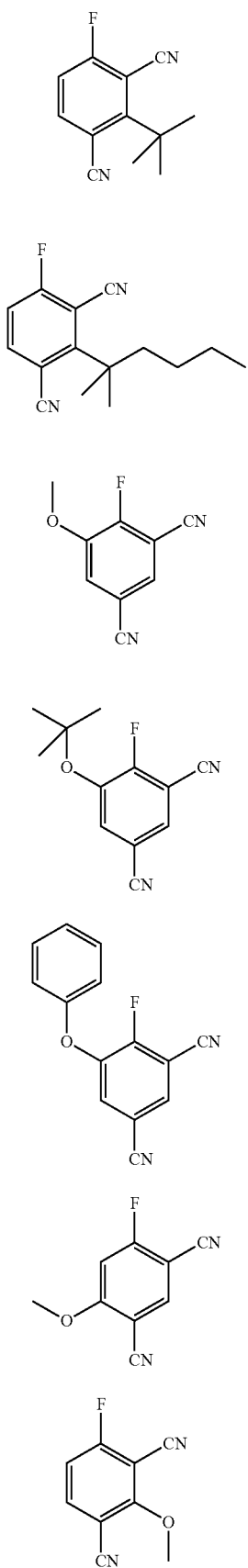
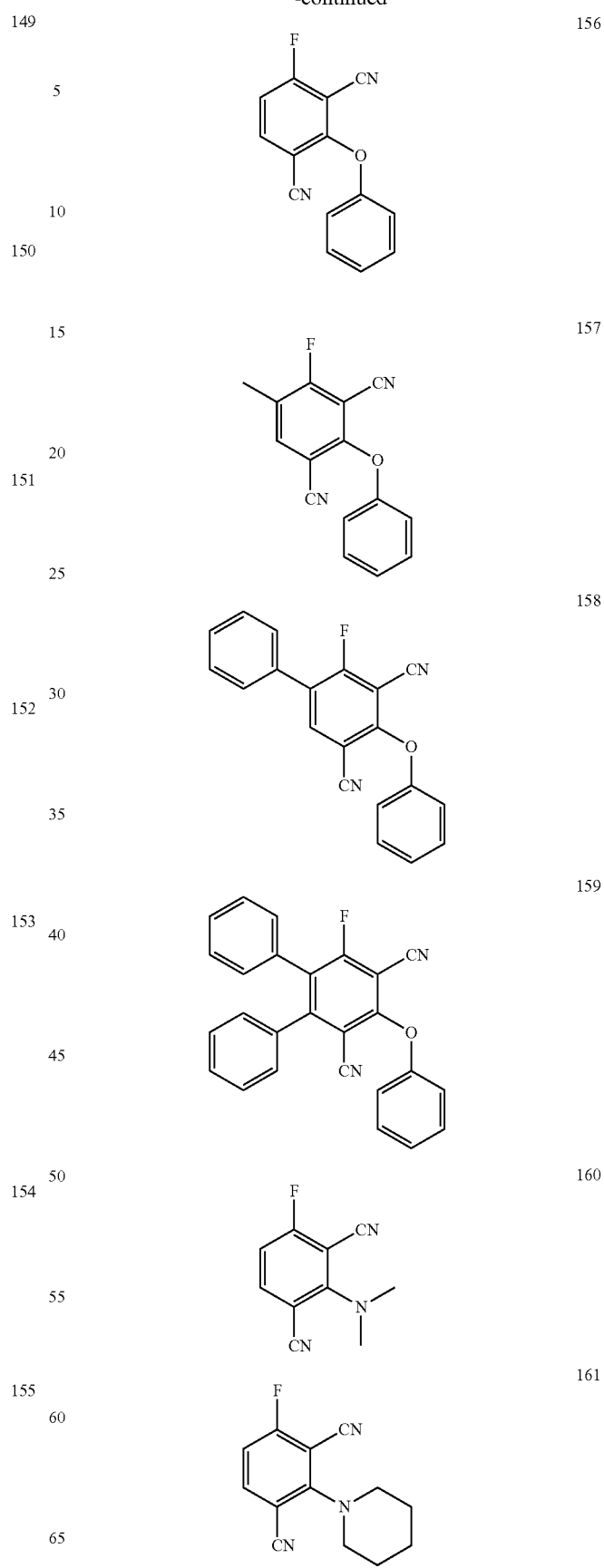

-continued
162 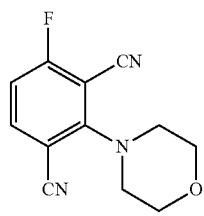
163 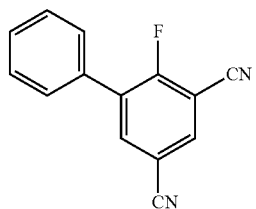
164 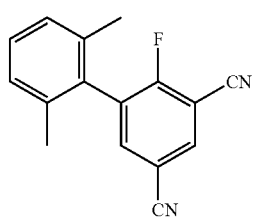
165 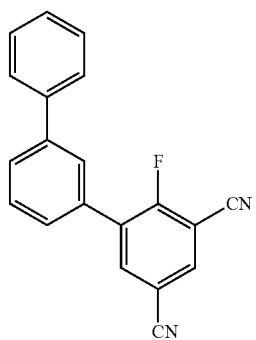
166 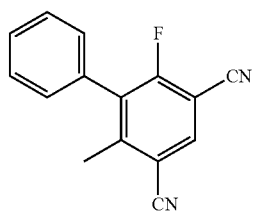
167 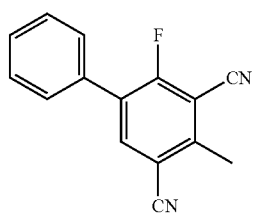
-continued
168 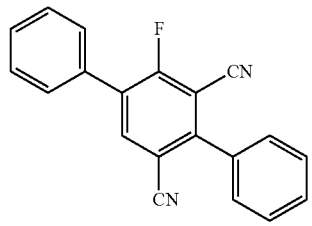
169 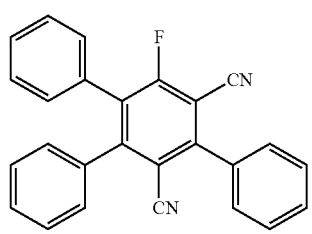
170 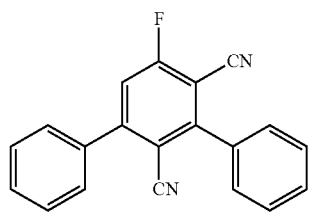
171 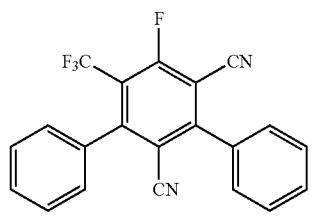
172 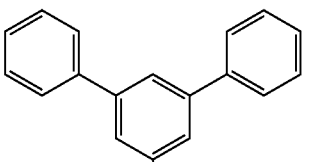
173 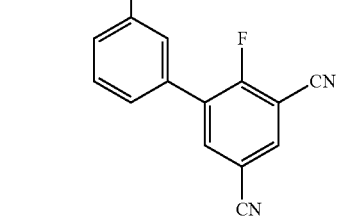

174 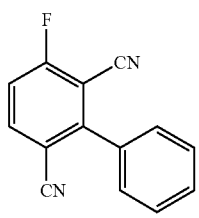
175 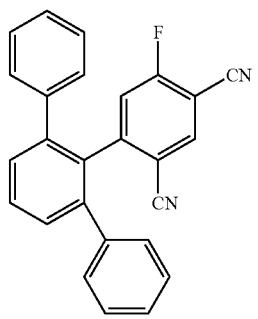
176 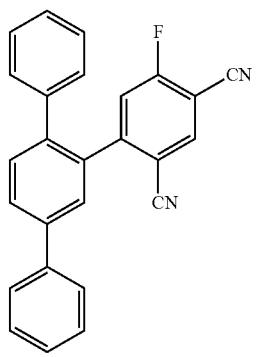
177 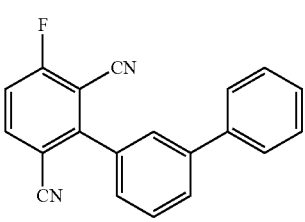
178 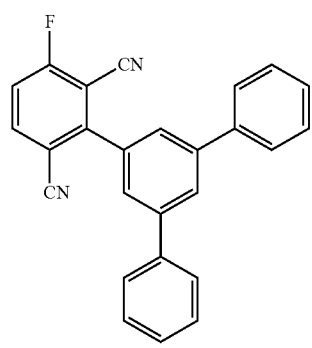
179 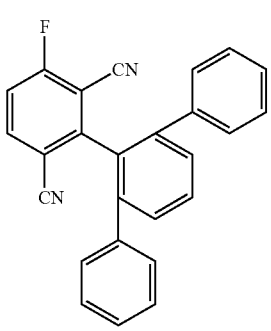
180 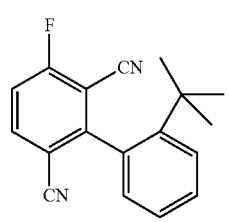
181 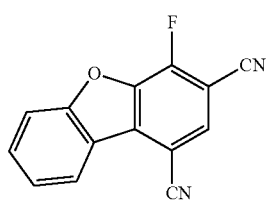
182 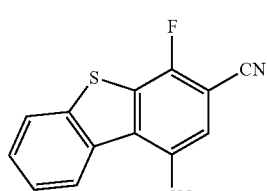
183 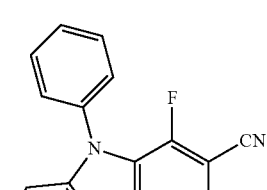
184 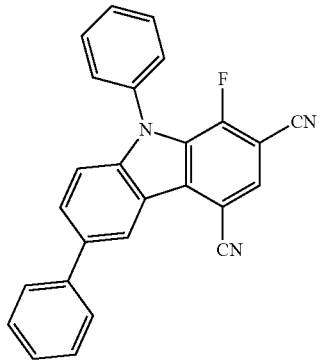

| | |
|---|---|
| 185 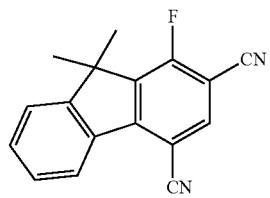 | 191 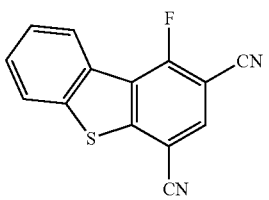 |
| 186 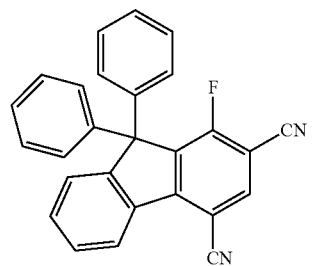 | 192 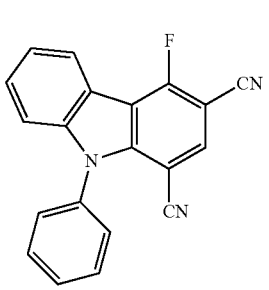 |
| 187 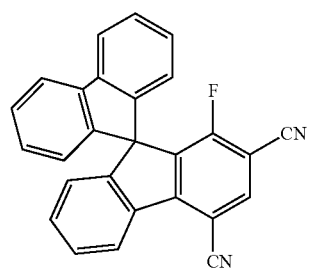 | 193 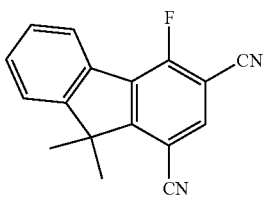 |
| 188 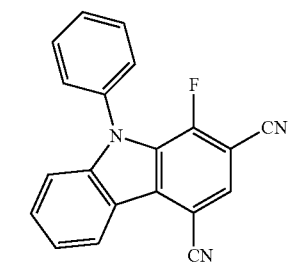 | 194 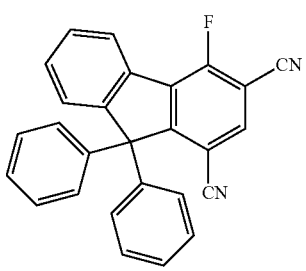 |
| 189 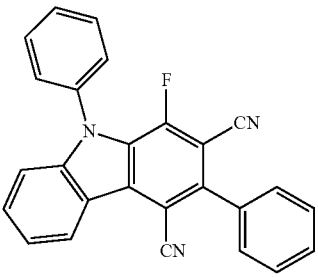 | 195 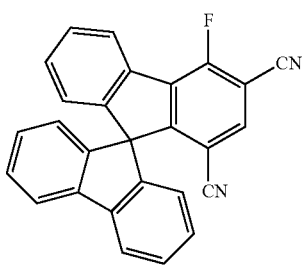 |
| 190 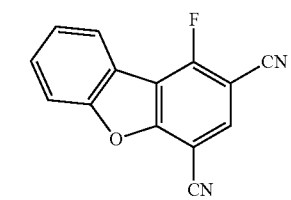 | 196 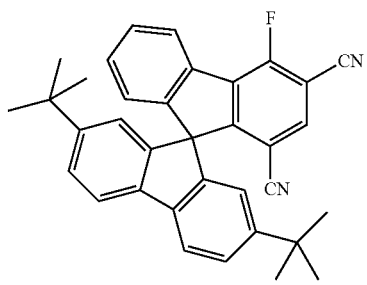 |

-continued
197
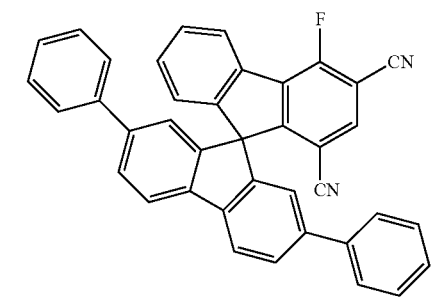
198
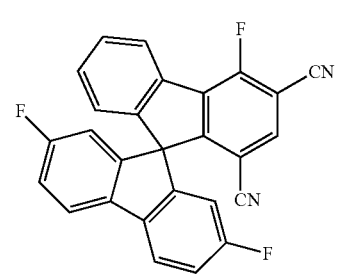
199
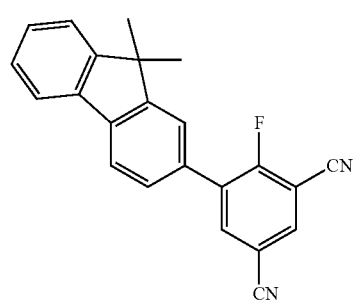
200
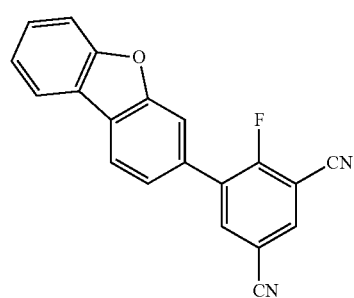
201
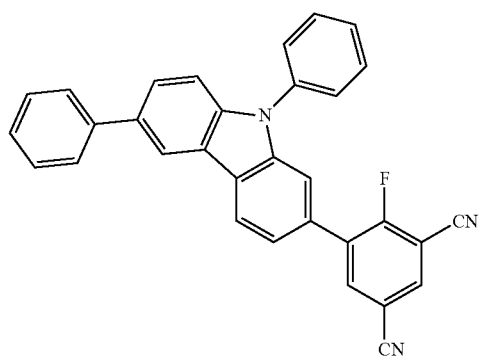
-continued
202
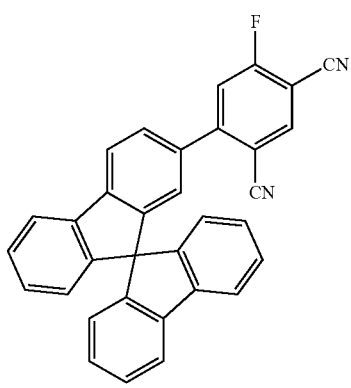
203
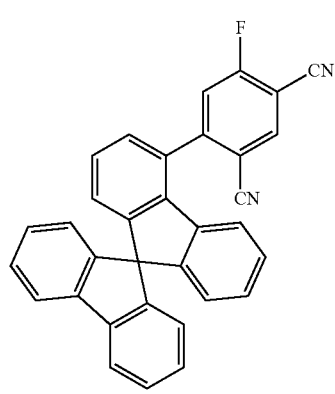
204
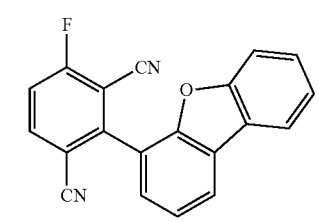
205
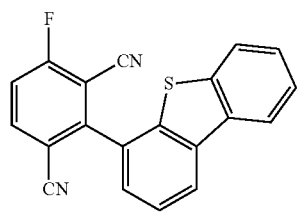
206
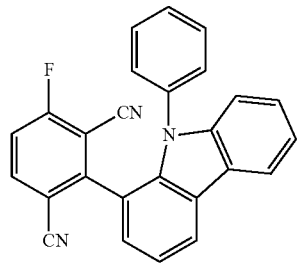

207 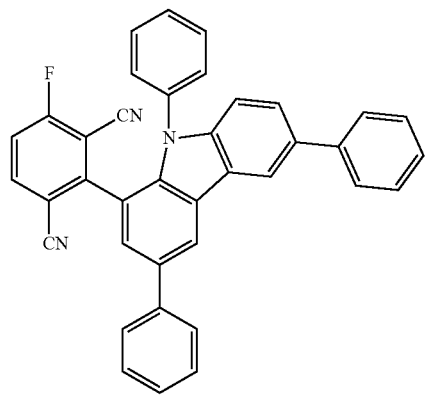
208 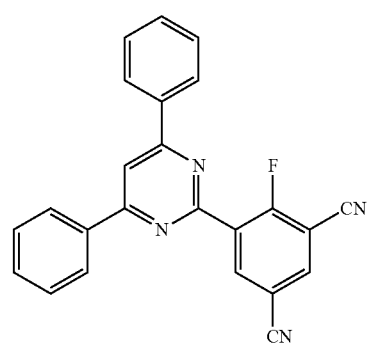
209 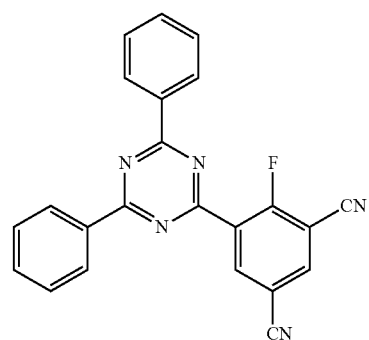
210 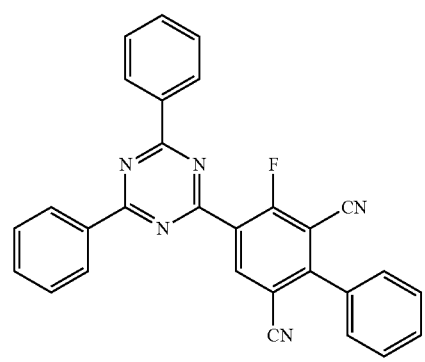
211 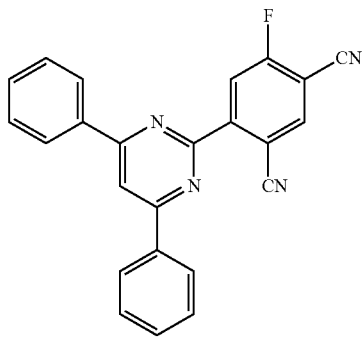
212 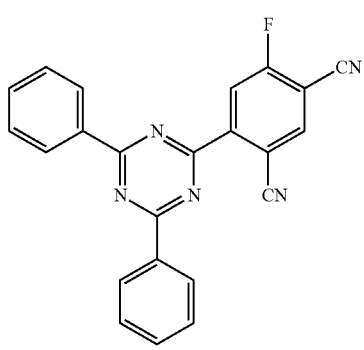
213 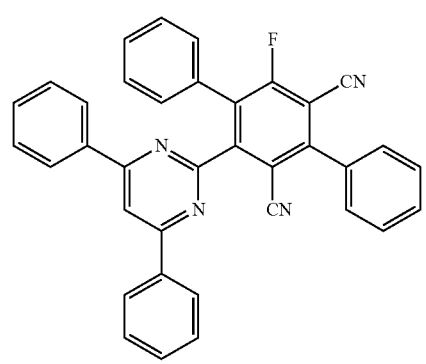
214 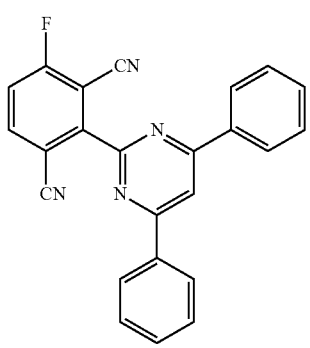

-continued
215
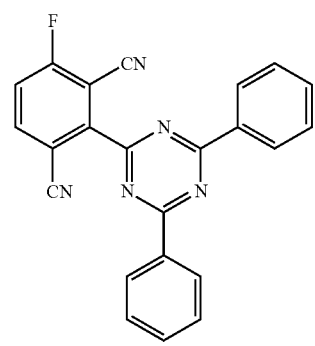
216
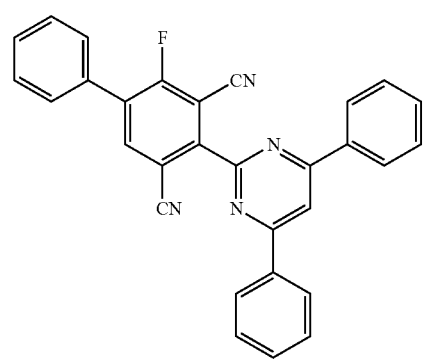
217
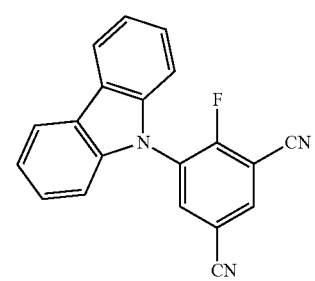
218
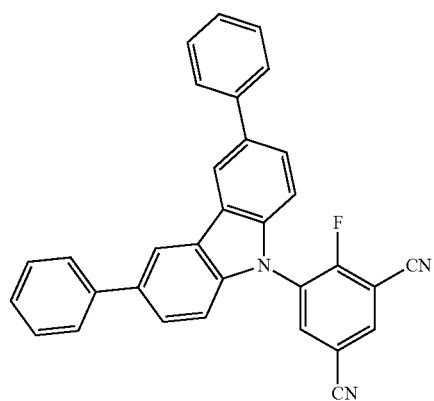
-continued
219
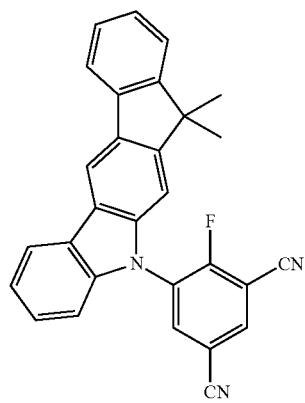
220
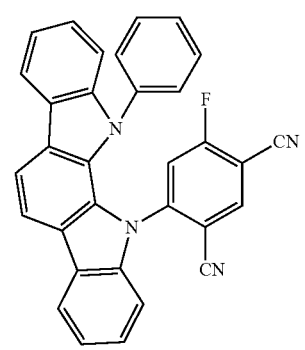
221
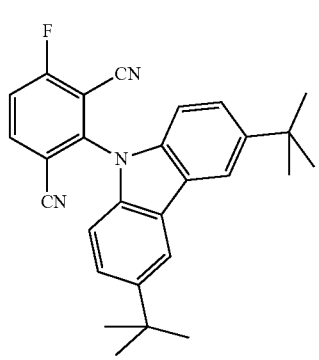
222
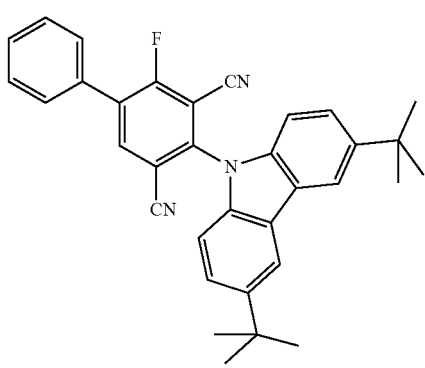

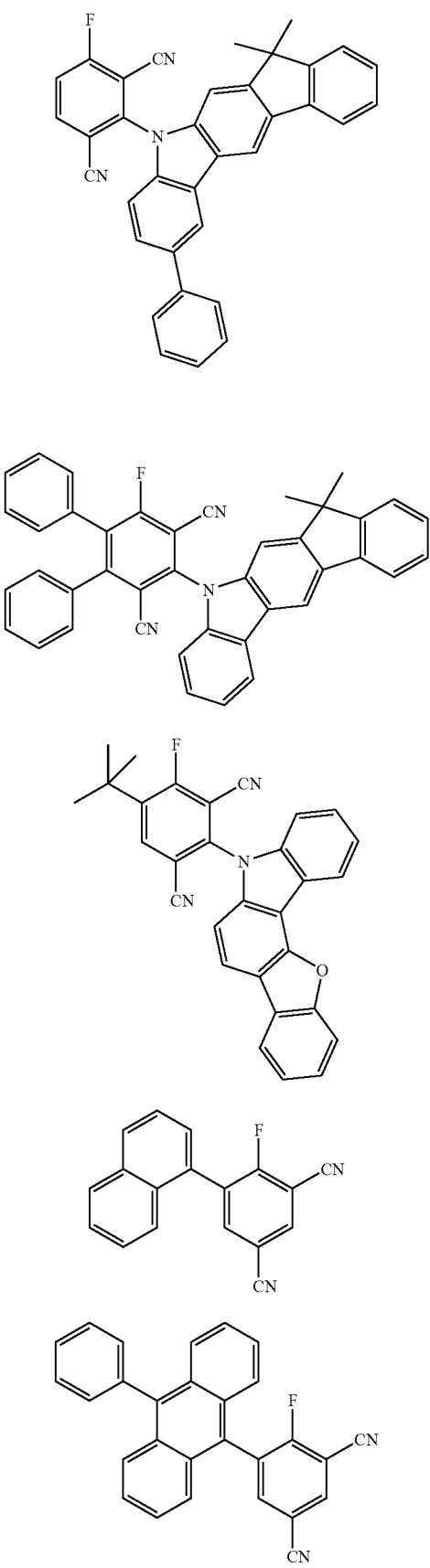
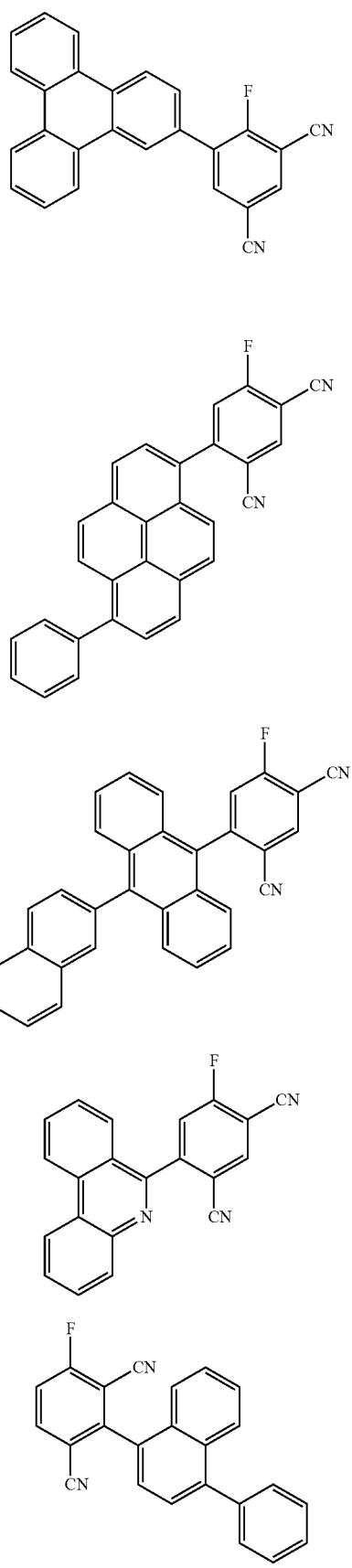

233 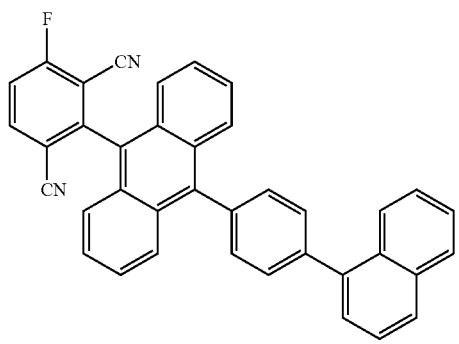
234 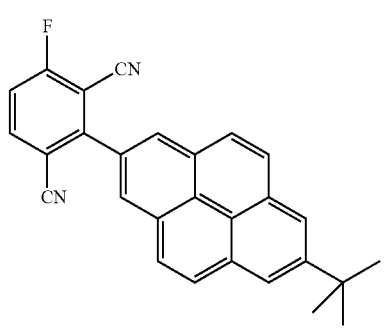
235 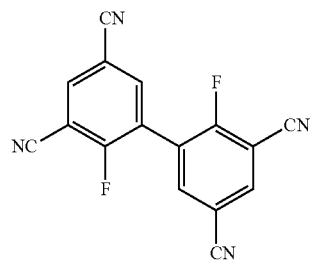
236 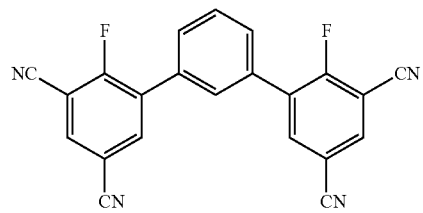
237 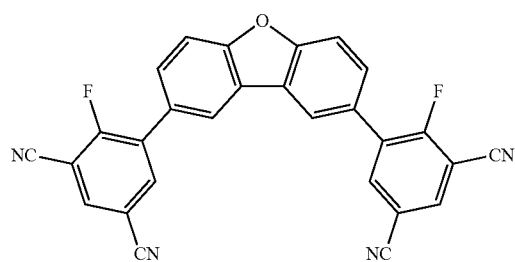
238 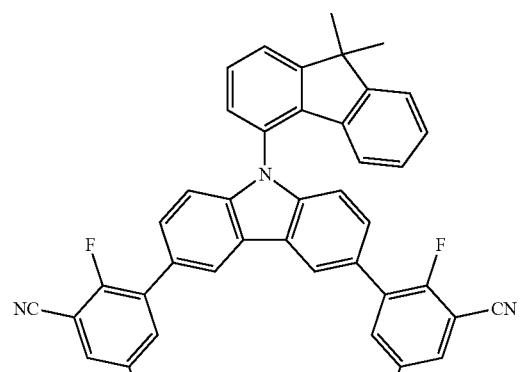
239 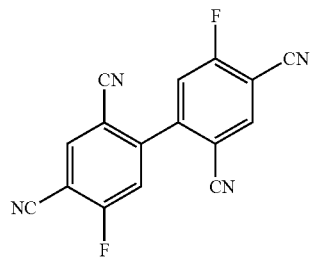
240 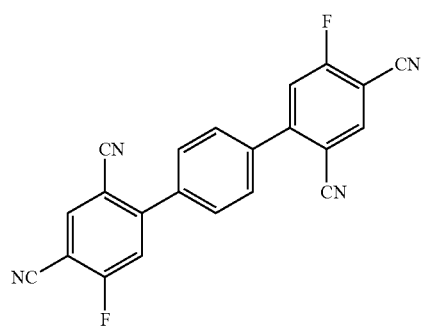
241 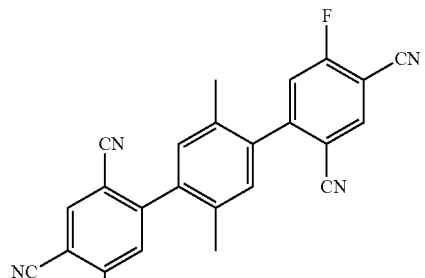
242 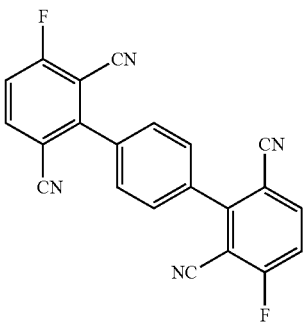

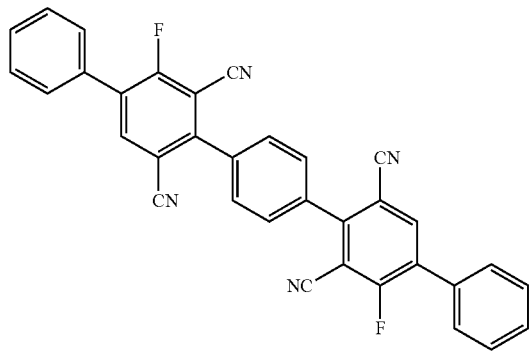

243

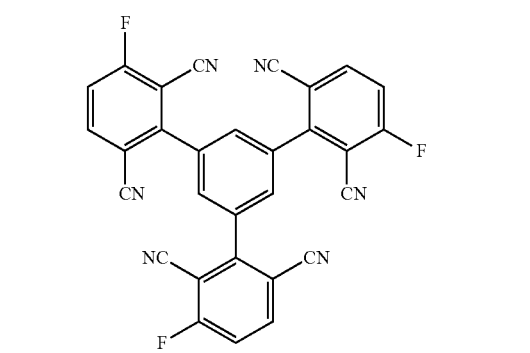

244

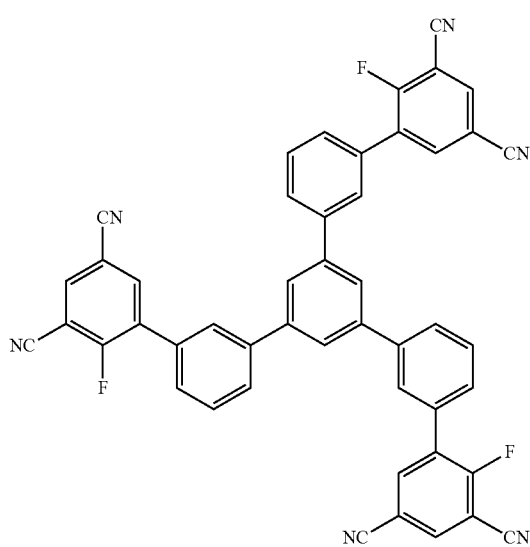

245

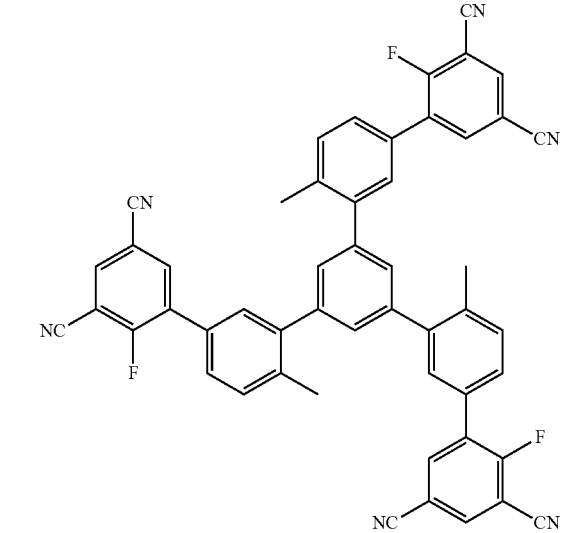

246

The compounds according to the invention can be prepared, for example, by the routes outlined in Scheme 1 and 2.

Scheme 1:

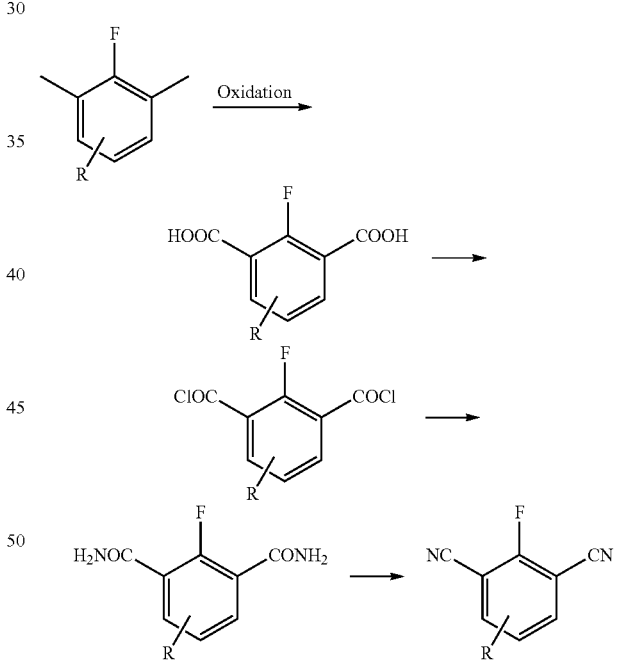

The synthesis depicted in Scheme 1 starts from 2-fluoro-meta-xylene derivatives, where the radical R is as defined above. Depending on the precise structure of the substituents R, a protecting group may also be necessary here. Suitable protecting groups are known to the person skilled in the art of organic synthesis. These are oxidised in a first step to give the corresponding isophthalic acids. Suitable oxidants are, for example, inorganic oxidants, such as permanganates, chromates, peroxodisulfates, persulfates (ozone), hypochlorites, chlorites, hydrogen peroxide or oxygen, or organic oxidants, such as peroxides or percarboxylic acids. In the next step, the carboxylic acid groups are converted into the corresponding carboxylic acid chlorides, for example by means of the action of inorganic acid chlorides, such as thionyl chloride, phosphoryl chloride or oxalyl chloride, optionally in the presence of an activator, such as DMF. In the next step, the carboxylic acid chloride is converted into the carboxylic acid amide by the action of ammonia. This is dehydrated to give the nitrile by the action of dehydrating agents, such as, for example, inorganic acid chlorides, such as thionyl chloride, phosphoryl chloride or oxalyl chloride, optionally in the presence of an activator, such as DMF.

The analogous reaction sequence can also be carried out starting from 6-fluoro-meta-xylene derivatives.

If R stands for Cl, Br or iodine, the compounds can be functionalised further by C—C or C—N coupling reactions known to the person skilled in the art, such as Suzuki, Negishi, Yamamoto, Grignard-Cross, Heck, Sonogashira, Buchwald, etc., coupling. It is also possible firstly to convert the halogen functionality into a boronic acid derivative. These halogen- or boronic acid-substituted compounds are also suitable as starting material for the corresponding dimeric, trimeric, etc., structures, i.e. structures of the formulae (1), (2) and (3) in which n is 1, since these above-mentioned coupling reactions can also be carried out with a corresponding disubstituted, trisubstituted, etc., group L.

Scheme 2:

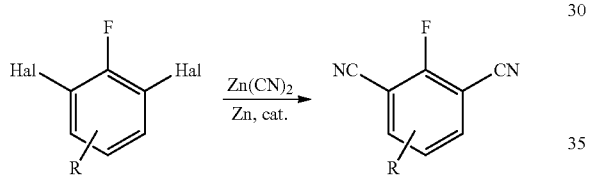

The synthesis depicted in Scheme 2 starts from 2-fluoro-1,3-dihalobenzene derivatives, where Hal stands for Cl, Br or I and the radical R is as defined above. Depending on the precise structure of the substituents R, a protecting group may also be necessary here. Suitable protecting groups are known to the person skilled in the art of organic synthesis. These are reacted with $Zn(CN)_2$ in the presence of zinc and a catalyst to give the corresponding cyano compounds. Suitable as catalyst are palladium compounds having phosphine ligands, for example $Pd(OAc)_2$ with XPhos.

The analogous reaction sequence can also be carried out starting from 6-fluoro-1,3-dihalobenzene derivatives.

The present invention therefore furthermore relates to a process for the preparation of a compound of the formula (1) or (2) or (3), comprising the reaction steps:
a) oxidation of a fluoro-meta-xylene derivative to give the carboxylic acid; and
b) conversion of the carboxylic acid functionalities into nitrile groups.

The present invention again furthermore relates to a process for the preparation of a compound of the formula (1) or (2) or (3) by reaction of a fluoro-meta-dihalobenzene derivative with $Zn(CN)_2$ and Zn in the presence of a catalyst.

The compounds according to the invention are suitable as synthesis precursor for the synthesis of materials which can be employed in organic electroluminescent devices. The fluorine substituent of these compounds is a reactive leaving group which can be replaced selectively by a nucleophile in a nucleophilic aromatic substitution ($S_N2$ aromatic).

The present invention therefore furthermore relates to the use of a compound according to the invention as starting material in a nucleophilic aromatic substitution reaction.

The present invention again furthermore relates to a process for the preparation of a compound of the formula (34) or formula (35) or formula (36),

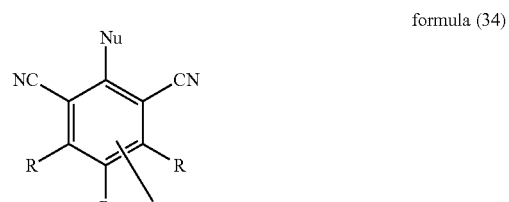
formula (34)

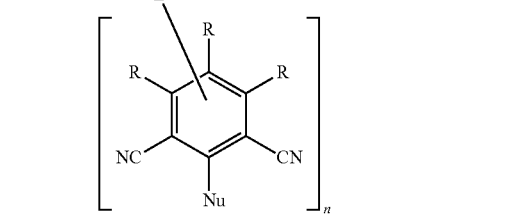
formula (35)

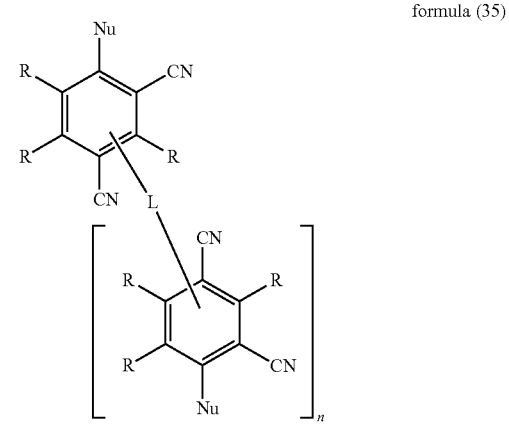
formula (36)

where Nu stands for a nucleophilic group and the other symbols used have the meanings given above,
by reaction of a compound of the formula (1) or formula (2) or formula (3) with a nucleophile.

This reaction is a nucleophilic aromatic substitution. This type of reaction is known to the person skilled in the art and he also knows which structures are nucleophiles.

The compounds of the formula (34) or (35) or (36), which are the reaction product of the process according to the invention, are suitable for use in an electronic device, in particular in an organic electroluminescent device. An electronic device in the sense of the present invention is a device which comprises at least one layer which comprises at least one organic compound.

The component here may also comprise inorganic materials or also layers which are built up entirely from inorganic materials.

The compounds according to the invention are distinguished over the prior art by one or more of the following surprising advantages:

1. The compounds according to the invention can be reacted in high yield, with high selectivity and under mild reaction conditions in a nucleophilic aromatic substitution reaction. The reaction products are formed here in very high purity, making complex purification, which is always also associated with losses of material, superfluous or at least only necessary to a slight extent. In particular, chromatographic purification of the materials is not necessary.
2. The compounds according to the invention are valuable precursors for the synthesis of materials which can be employed in organic electroluminescent devices.

The invention is explained in greater detail by the following examples without wishing to restrict it thereby. The person skilled in the art will be able to use the descriptions to carry out the invention throughout the range disclose and will be able to prepare further compounds according to the invention without inventive step and use them in electronic devices or use the process according to the invention.

EXAMPLES

The following syntheses are carried out, unless indicated otherwise, in dried solvents under a protective-gas atmosphere. The solvents and reagents can be purchased from Sigma-ALDRICH or ABCR. The respective numbers in square brackets or the numbers indicated for individual compounds relate to the CAS numbers of the compounds which are known from the literature, but are not commercially available.

A: Synthesis:

Example S1: 5-Bromo-2-fluoroisophthalonitrile, S1

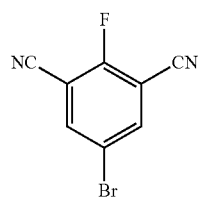 [SMILES: N#Cc1cc(Br)cc(C#N)c1F]

a) S1a: 5-Bromo-2-fluoroisophthalic acid, S1a

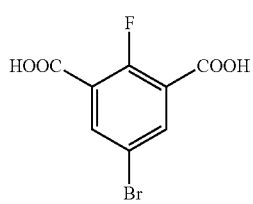

Procedure analogous to H. G. Menzella, J. Med. Chem., 2009, 52 (6), 1518. 663.8 g (4.2 mol) of potassium permanganate are added spoonwise with vigorous stirring to a mixture, warmed to 90° C., of 203.1 g (1 mol) of 5-bromo-2-fluoro-m-xylene [99725-44-7] and 2000 ml of water (attention: slightly exothermic reaction). When the addition is complete, the reaction mixture is stirred under reflux for a further 12 h. The mixture is allowed to cool to 70° C., the manganese dioxide formed is filtered off with suction through a Celite layer, rinsed twice with 300 ml of warm water each time and rendered acidic using conc. 300 ml of HCl with stirring. The water phase is allowed to cool, and the product which has precipitated out is then filtered off with suction, rinsed three times with 300 ml of water each time and then dried in vacuo. Yield: 205.7 g (782 mmol), 78%. Purity: about 98% according to $^1$H-NMR.

The following compounds are prepared analogously:

| Ex. | Starting material | Product | Yield |
|---|---|---|---|
| S2a | 1416549-07-9 | S2a | 66% |
| S3a | 26584-26-9 | S3a | 69% |
| S4a | 1407493-64-4 | S4a | 76% |
| S5a | 67205-30-5 | S5a | 70% |

-continued

| Ex. | Starting material | Product | Yield |
|---|---|---|---|
| S6a | 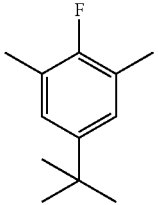\n2366-75-8 | 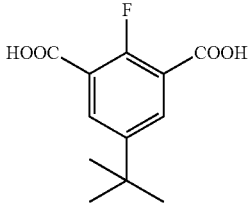\nS6a | 63% |
| S7a | 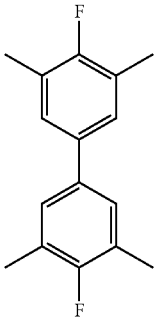\n1314888-40-8\nUse of 500 mmol | 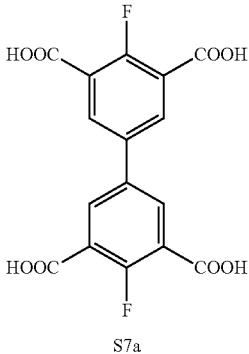 [SMILES: O=C(O)c1cc(-c2cc(C(=O)O)c(F)c(C(=O)O)c2)cc(C(=O)O)c1F]\nS7a | 46% |
| S8a | 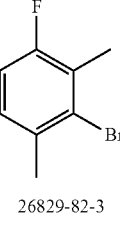\n344-16-1 | 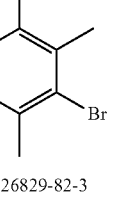\nS8a | 81% |
| S9a | 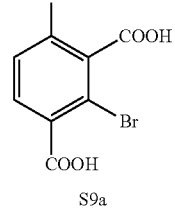\n26829-82-3 | 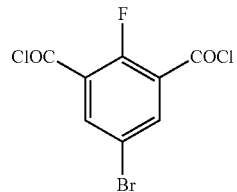\nS9a | 67% | b) S1 b: 5-Bromo-2-fluoroisophthaloyl chloride, S1b

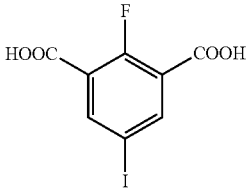

Procedure analogous to W. P. Heilmann, J. Med. Chem., 1978, 21 (9), 906. 20 drops of DMF are added with stirring to a mixture of 131.5 g (500 mmol) of 5-bromo-2-fluoroisophthalic acid, S1a and 500 ml of thionyl chloride, and the mixture is then slowly warmed to 70° C. When the evolution of HCl is complete, the mixture is stirred for a further 4 h, and the excess thionyl chloride is then distilled off until the residue solidifies to give a pale-yellow crystalline mass. The acid chloride is used without further purification. Yield: quantitative. Purity: about 98% according to $^1$H-NMR.

The following compounds are prepared analogously:

| Ex. | Starting material | Product | Yield |
|---|---|---|---|
| S2b | 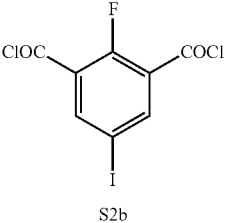\nS2a | 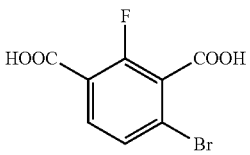\nS2b | quantitative |
| S3b | \nS3a | \nS3b | quantitative |

-continued
| Ex. | Starting material | Product | Yield |
|---|---|---|---|
| S4b | 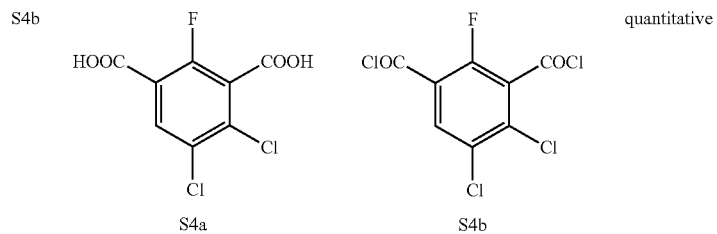 S4a | S4b | quantitative |
| S5b | 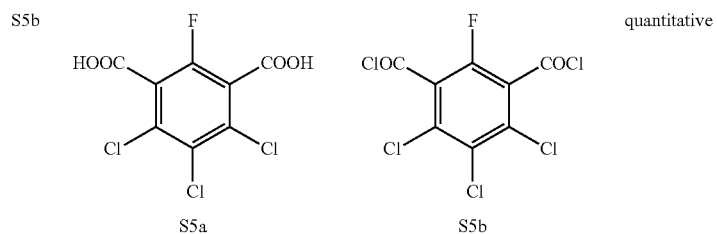 S5a | S5b | quantitative |
| S6b | 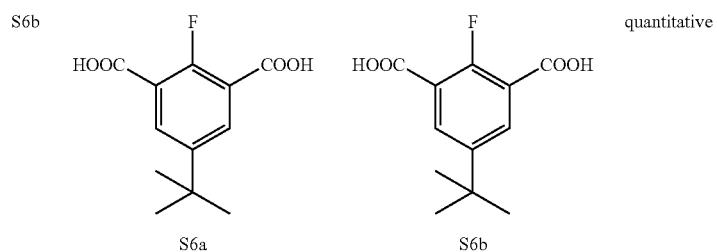 S6a | S6b | quantitative |
| S7b | 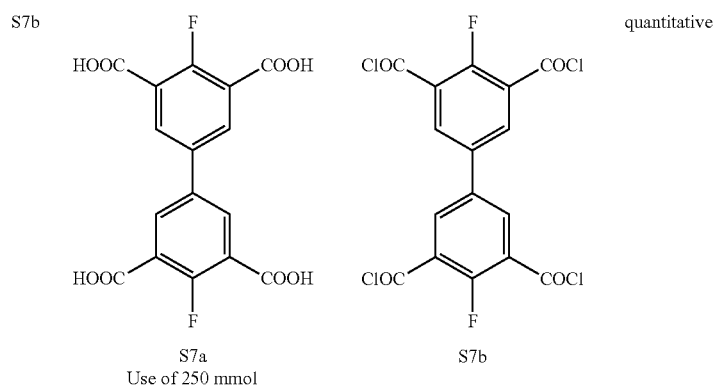 S7a Use of 250 mmol | S7b | quantitative |
| S8b | 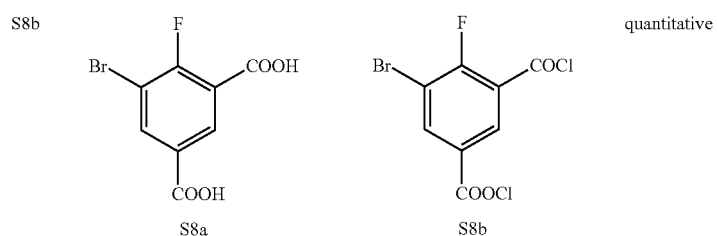 S8a | S8b | quantitative |

-continued

| Ex. | Starting material | Product | Yield |
|---|---|---|---|
| S9b | S9a | S9b | quantitative | c) S1c: 5-Bromo-2-fluoroisophthalamide, S1c

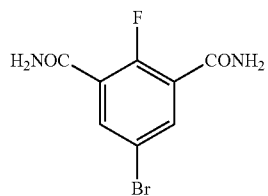 [SMILES: NC(=O)c1cc(Br)cc(C(N)=O)c1F]

Procedure analogous to W. P. Heilmann, J. Med. Chem., 1978, 21 (9), 906. A solution of 150.0 g (500 mmol) of 5-bromo-2-fluoroisophthaloyl chloride, S1b in 300 ml of dioxane is added dropwise to a vigorously stirred mixture of 300 ml of conc. ammonium hydroxide and 800 ml of dioxane with ice-cooling at such a rate that the temperature does not exceed 50° C. When the exothermic reaction is complete, the cooling bath is removed, the reaction mixture is stirred further until an internal temperature of 25° C. has been reached, the solid which has precipitated out is filtered off with suction, washed three times with 200 ml of water and then dried in vacuo. Yield: 87.5 g (335 mmol) 67%. Purity: about 98% according to $^1$H-NMR The following compounds are prepared analogously:

| Ex. | Starting material | Product | Yield |
|---|---|---|---|
| S2c | S2b | S2c | 64% |
| S3c | S3b | S3c | 70% |
| S4c | S4b | S4c | 66% |
| S5c | S5b | S5c | 68% |
| S6c | S6b | S6c | 73% |
| S7c | S7b Use of 250 mmol | S7c | 59% |

| Ex. | Starting material | Product | Yield |
|---|---|---|---|
| S8c | S8b | S8c | 79% |
| S9c | S9b | S9c | 77% | d) S1: 5-Bromo-2-fluoroisophthalonitrile, S1

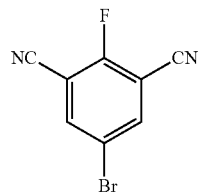 [SMILES: N#Cc1cc(Br)cc(C#N)c1F]

Procedure analogous to W. P. Hellmann, J. Med. Chem., 1978, 21 (9), 906.

A mixture of 65.3 g (250 mmol) of 5-bromo-2-fluoroisophthalamide, S1c and 142 ml (1.5 mol) of phosphoryl chloride and 10 drops of DMF is slowly heated to 90° C. with vigorous stirring. When the evolution of HCl is complete, the reaction mixture is allowed to cool, then poured into a mixture of 5 kg of ice and 1000 ml of water. The product which has precipitated out is filtered off, washed three times with 200 ml of water each time and dried in vacuo. The purification is carried out by recrystallisation from chlorobenzene. Yield: 49.5 g (220 mmol) 88%. Purity: about 98% according to $^1$H-NMR The following compounds are prepared analogously:

| Ex. | Starting material | Product | Yield |
|---|---|---|---|
| S2 | S2c | S2 | 87% |
| S3 | S3c | S3 | 86% |
| S4 | S4c | S4 | 82% |
| S5 | S5c | S5 | 90% |
| S6 | S6c | S6 | 84% |
| S7 | S7c Use of 125 mmol | S7 | 68% |
| S8 | S8c | S8 | 72% |

-continued

| Ex. | Starting material | Product | Yield |
|---|---|---|---|
| S9 | 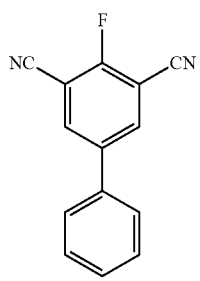 [SMILES: N#Cc1cc(-c2ccccc2)cc(C#N)c1F] S9c | S9 | 77% |

S10: 5-Phenyl-2-fluoroisophthalonitrile, S10

Variant A:
A mixture of 22.5 g (100 mmol) of 5-bromo-2-fluoroisophthalonitrile, S1, 14.6 g (120 mmol) of phenylboronic acid [98-80-6], 42.5 g (200 mmol) of tripotassium phosphate, 1.8 g (6 mmol) of tri-o-tolylphosphine, 224 mg (1 mmol) of palladium(II) acetate, 200 ml of toluene, 50 ml of dioxane and 200 ml of water is heated under reflux until the 5-bromo-2-fluoroisophthalonitrile, S1 has been consumed (about 6 h). After cooling, the aqueous phase is separated off, the organic phase is filtered through a Celite bed in order to remove palladium, the filtrate is washed three times with 200 ml of water each time, once with 200 ml of saturated sodium chloride solution and dried over magnesium sulfate. The residue obtained after removal of the solvent is recrystallised twice from DMF. Yield: 15.1 g (68 mmol) 68%. Purity: about 99% according to $^1$H-NMR.

Variant B:
A mixture of 22.5 g (100 mmol) of 5-bromo-2-fluoroisophthalonitrile, S1, 14.6 g (120 mmol) of phenylboronic acid, 17.5 g (300 mmol) of potassium fluoride, anhydrous, 263 mg (1.3 mmol) of tri-tert-butylphosphine, 224 mg (1 mmol) of palladium(II) acetate, 250 ml of THF is heated under reflux until the 5-bromo-2-fluoroisophthalonitrile, S1 has been consumed (about 2 h). After cooling, the mixture is filtered off through a Celite bed and rinsed with 200 ml of THF in order to remove salts and palladium. The filtrate is evaporated to dryness, the residue is washed by stirring with 200 ml of a mixture of water/EtOH (1:1, vv), the solid is filtered off with suction, washed three times with 100 ml of ethanol each time and dried in vacuo. The solid obtained in this way is recrystallised twice from DMF. Yield: 16.9 g (76 mmol) 76%. Purity: about 99% according to $^1$H-NMR. A further purification can be carried out by repeated recrystallisation or chromatography and by fractional sublimation in vacuo.

The following compounds are prepared analogously:

| Ex. | Starting material | Boronic acid | Product | Variant | Yield |
|---|---|---|---|---|---|
| S11 | S1 | 100379-00-8 | B | | 76% |
| S12 | S1 | 4688-76-0 | A | | 64% |

-continued
| Ex. | Starting material | Boronic acid | Product Variant | Yield |
|---|---|---|---|---|
| S13 | 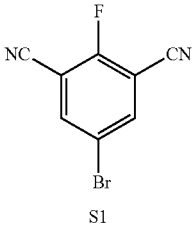 S1 | 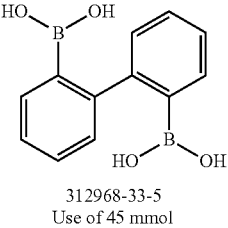 312968-33-5 Use of 45 mmol | 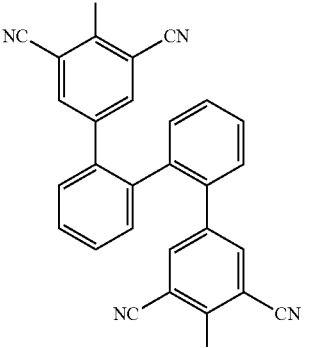 A | 48% |
| S14 | 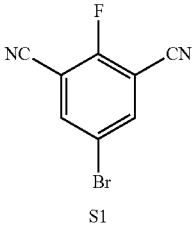 S1 | 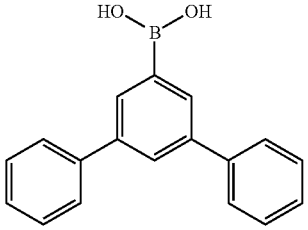 128388-54-5 | 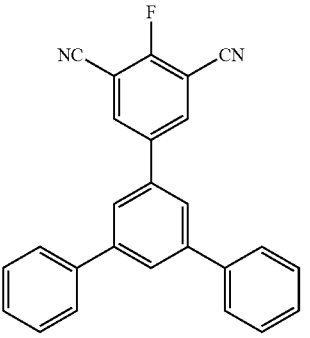 A | 78% |
| S15 | 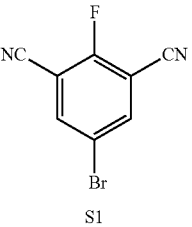 S1 | 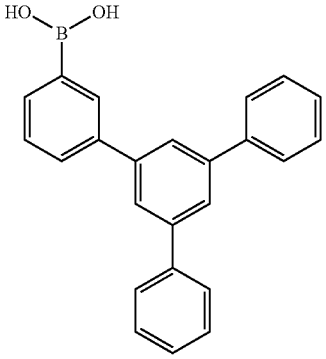 1233200-59-3 | 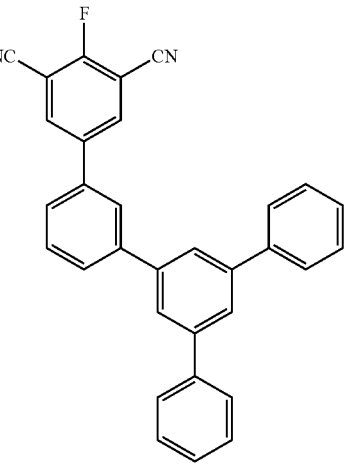 A | 63% |

| Ex. | Starting material | Boronic acid | Product Variant | Yield |
|---|---|---|---|---|
| S16 | 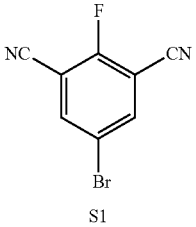 S1 | 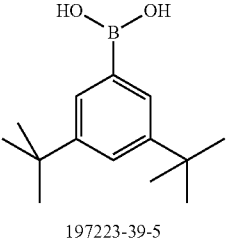 [SMILES: CC(C)(C)c1cc(B(O)O)cc(C(C)(C)C)c1] 197223-39-5 | 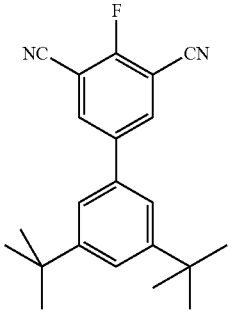 A | 75% |
| S17 | 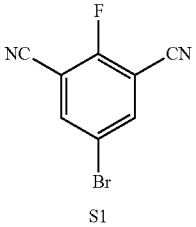 S1 | 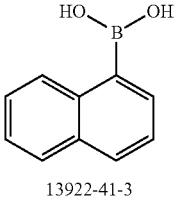 [SMILES: OB(O)c1cccc2ccccc12] 13922-41-3 | 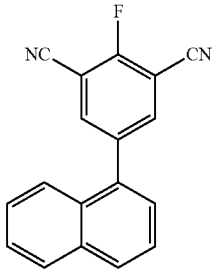 A | 71% |
| S18 | 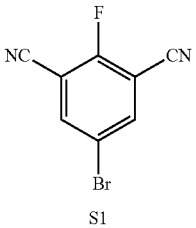 S1 | 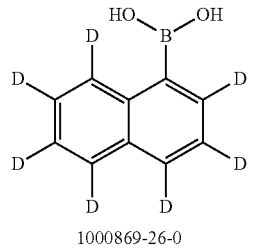 1000869-26-0 | 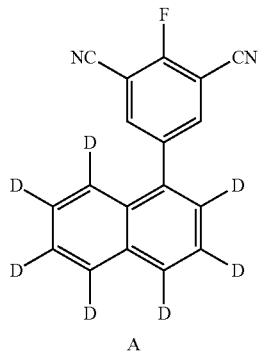 A | 70% |
| S19 | 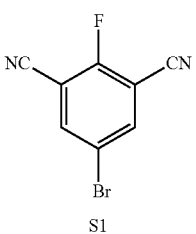 S1 | 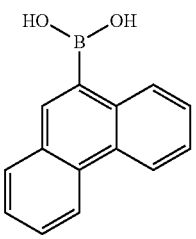 68572-87-2 | 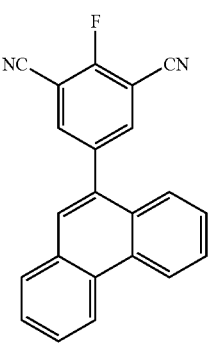 A | 73% |

| Ex. | Starting material | Boronic acid | Product Variant | Yield |
|---|---|---|---|---|
| S20 | 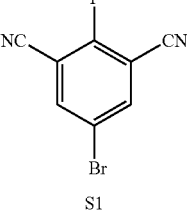 S1 | 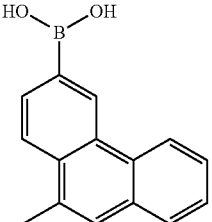 654664-63-8 | 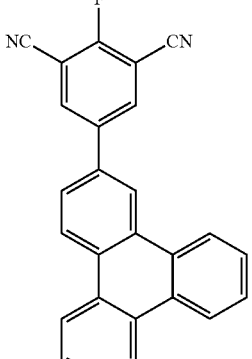 B | 56% |
| S21 | 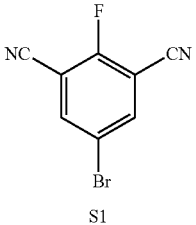 S1 | 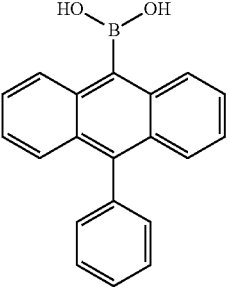 334658-75-2 | 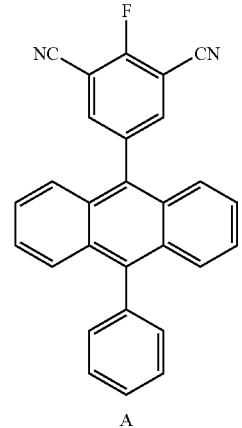 A | 58% |
| S22 | 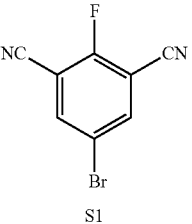 S1 | 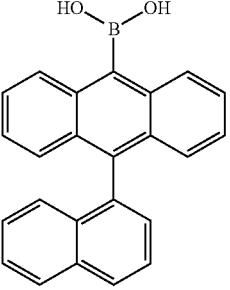 400607-46-7 | 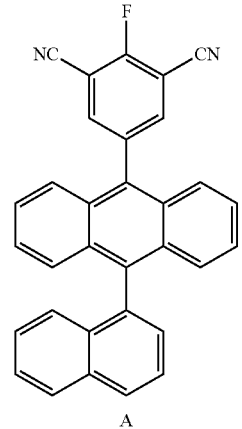 A | 53% |

| Ex. | Starting material | Boronic acid | Product Variant | Yield |
|---|---|---|---|---|
| S23 | 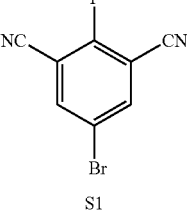 S1 | 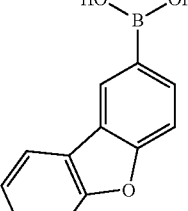 402936-15-6 | 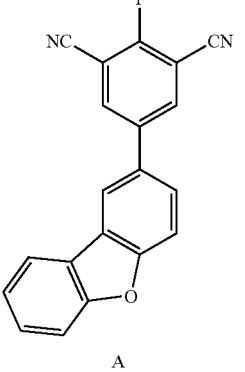 A | 77% |
| S24 | 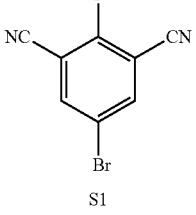 S1 | 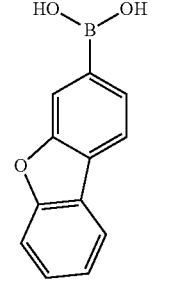 395087-89-5 | 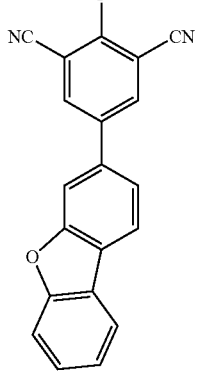 A | 80% |
| S25 | 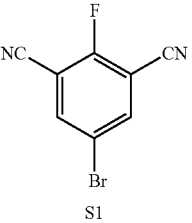 S1 | 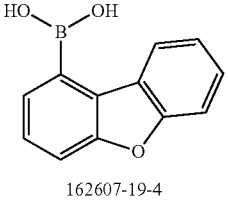 162607-19-4 | 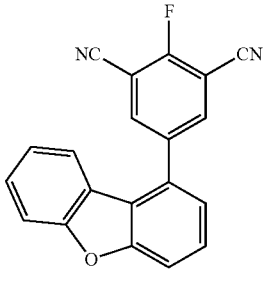 A | 76% |
| S26 | 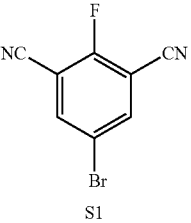 S1 | 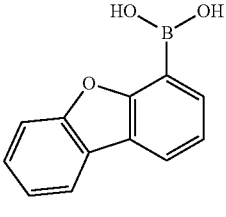 100124-06-9 | 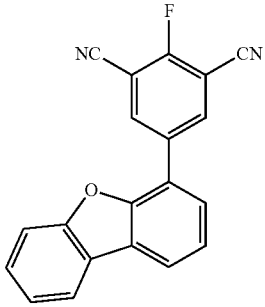 A | 69% |

-continued
| Ex. | Starting material | Boronic acid | Product Variant | Yield |
|---|---|---|---|---|
| S27 | 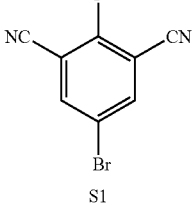 S1 | 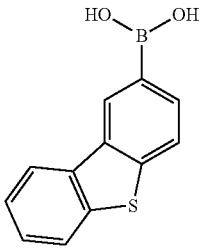 668983-97-9 | 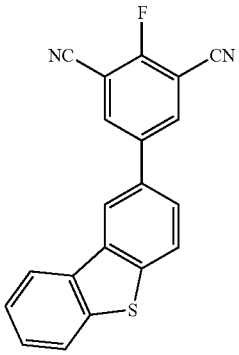 A | 83% |
| S28 | 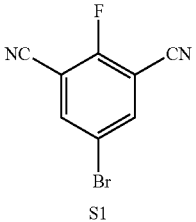 S1 | 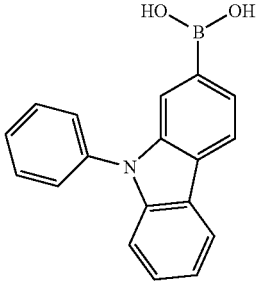 1001911-63-2 | 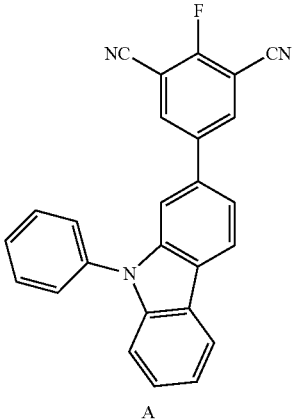 A | 81% |
| S29 | 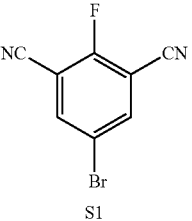 S1 | 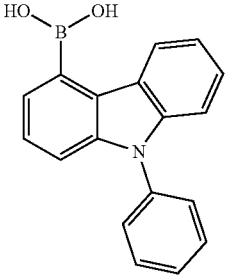 1370555-65-9 | 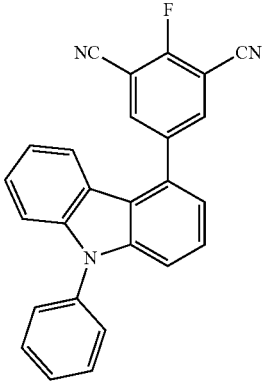 A | 70% |

-continued
| Ex. | Starting material | Boronic acid | Product Variant | Yield |
|---|---|---|---|---|
| S30 | 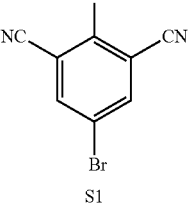 S1 | 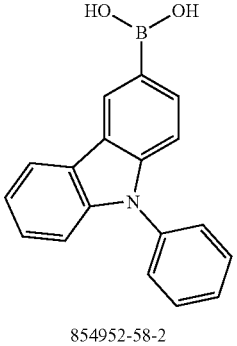 [SMILES: OB(O)c1ccc2c(c1)c1ccccc1n2-c1ccccc1] 854952-58-2 | 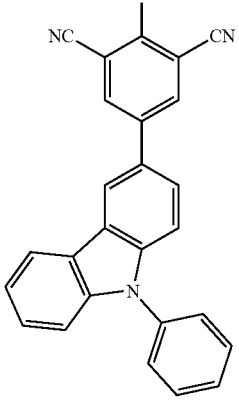 A | 74% |
| S31 | 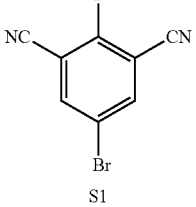 S1 | 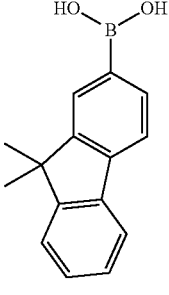 333432-28-3 | 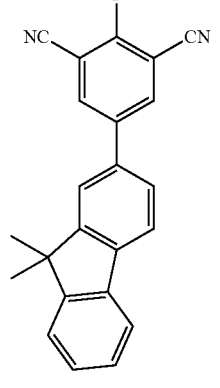 A | 80% |
| S32 | 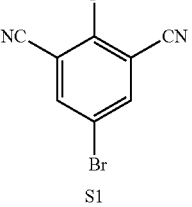 S1 | 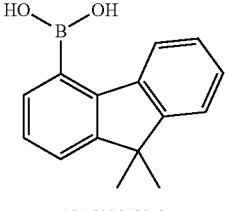 1246022-50-3 | 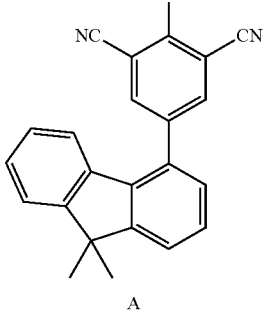 A | 69% |
| S33 | 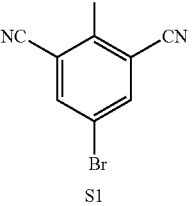 S1 | 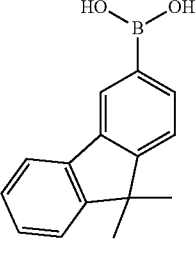 1251773-34-8 | 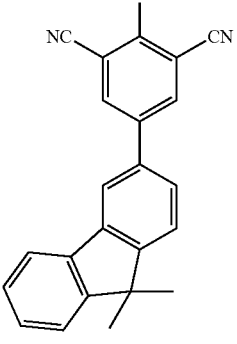 A | 77% |

-continued
| Ex. | Starting material | Boronic acid | Product Variant | Yield |
|---|---|---|---|---|
| S34 | 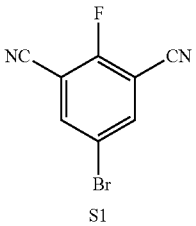 S1 | 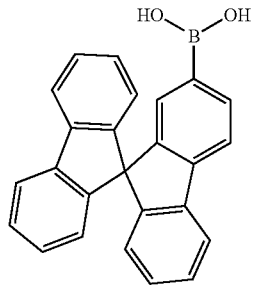 236389-21-2 | 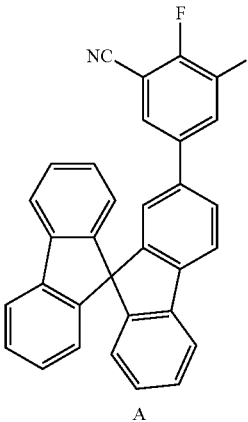 A | 79% |
| S35 | 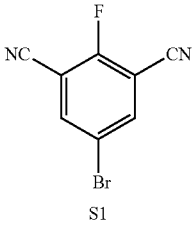 S1 | 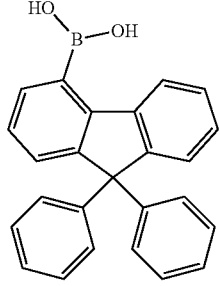 1224976-40-2 | 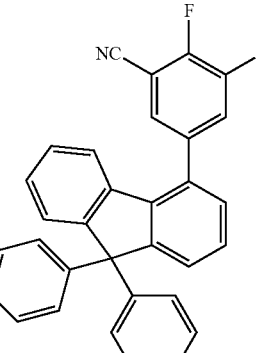 A | 72% |
| S36 | 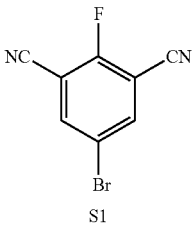 S1 | 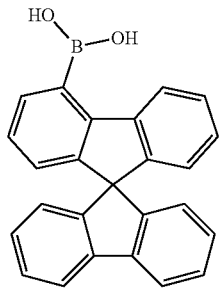 1421789-05-0 | 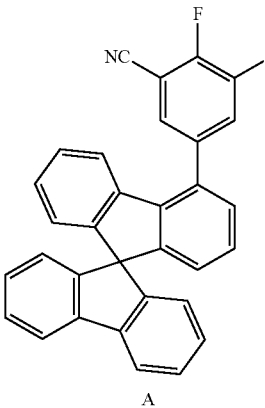 A | 71% |

-continued
| Ex. | Starting material | Boronic acid | Product Variant | Yield |
|---|---|---|---|---|
| S37 | S1 | 1214723-25-7 | B | 66% |
| S38 | S1 | 1313018-07-3 | A | 78% |
| S39 | S1 | 201802-67-7 | A | 67% |
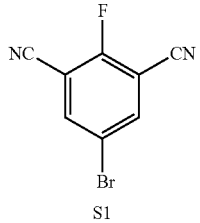
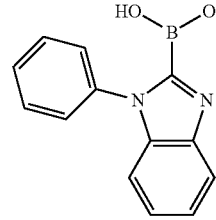
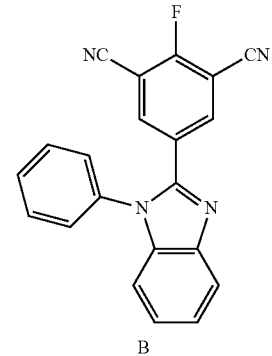
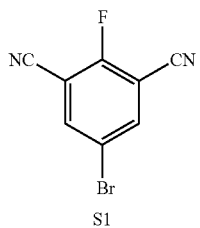
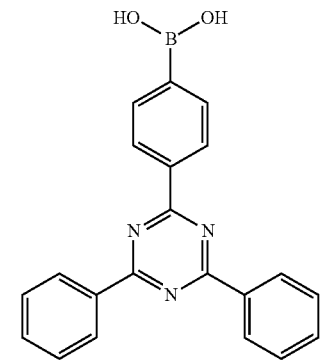
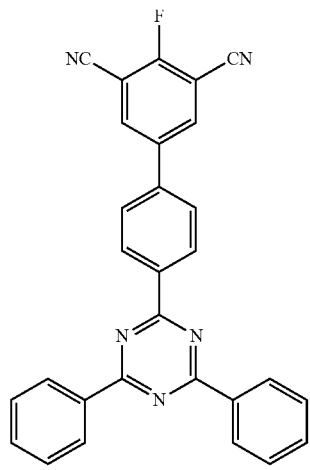
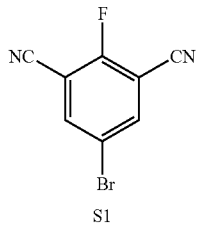
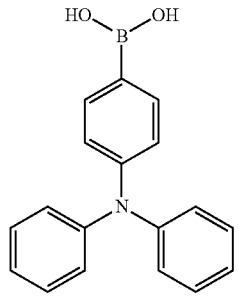
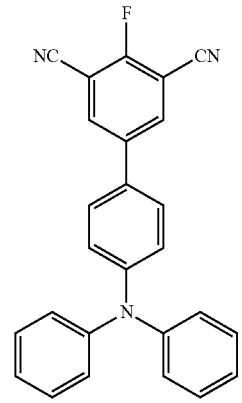

| Ex. | Starting material | Boronic acid | Product Variant | Yield |
|---|---|---|---|---|
| S40 | S1 | 943836-24-6 | A | 69% |
| S41 | S1 | 823-96-1 | B | 38% |
| S42 | S2 | 4612-28-6<br>Use of 45 mmol | A | 46% |
| S43 | S3 | 5122-95-2 | A | 55% |
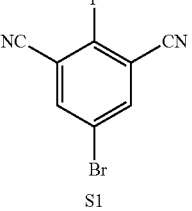
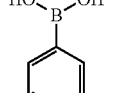
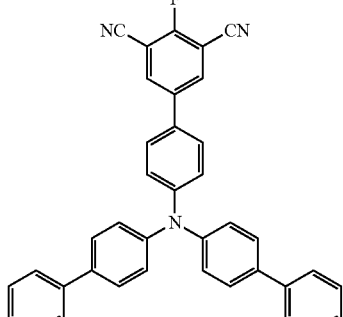
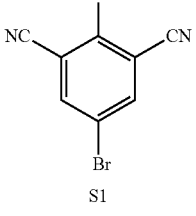
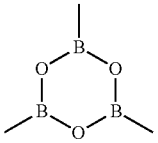
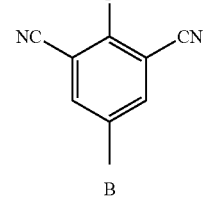
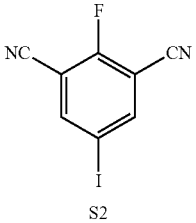
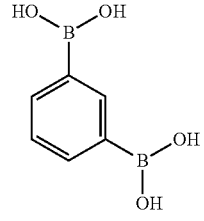
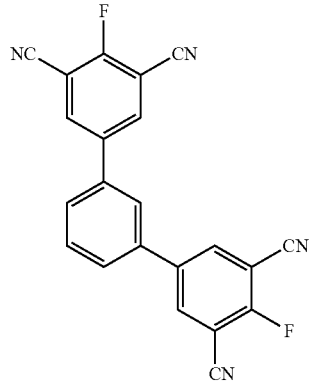
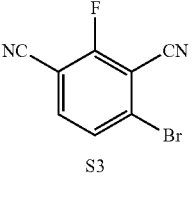
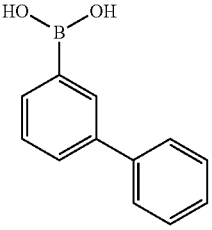
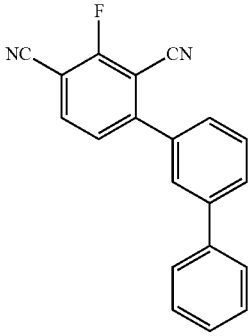

-continued

| Ex. | Starting material | Boronic acid | Product Variant | Yield |
|---|---|---|---|---|
| S44 | S4 Use of 50 mmol | 98-80-6 | B | 34%. |
| S45 | S5 Use of 30 mmol | 98-80-6 | B | 23% |
| S46 | S8 | 123324-71-0 | A | 64% |
| S47 | S9 | 854952-45-7 | A | 75% |

| Ex. | Starting material | Boronic acid | Product Variant | Yield |
|---|---|---|---|---|
| S48 | (17654-69-2) | (1314221-56-1) | | 73% |

S49: 5-(N-Diphenylamino)-2-fluoroisophthalonitrile, S49

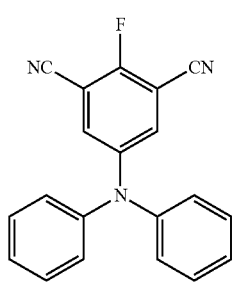 [SMILES: N#Cc1cc(N(c2ccccc2)c2ccccc2)cc(C#N)c1F]

A mixture of 22.5 g (100 mmol) of 5-bromo-2-fluoroisophthalonitrile, S1, 20.3 g (120 mmol) of diphenylamine, 11.5 g (120 mmol) of sodium tert-butoxide, 405 mg (2 mmol) of tri-tert-butylphosphine, 224 mg (1 mmol) of palladium(II) acetate and 300 ml of toluene is heated under reflux until the 5-bromo-2-fluoroisophthalonitrile, S1 has been consumed (about 8 h). After cooling, 100 ml of water are added, the solid which has precipitated out is filtered off with suction, washed three times with 50 ml of ethanol each time and dried in vacuo. The solid obtained in this way is dissolved in 300 ml of dichloromethane, the solution is filtered through a Celite bed in order to remove salts and palladium. The residue obtained after evaporation of the filtrate is recrystallised twice from dioxane/EtOH. Yield: 22.9 g (73 mmol) 73%. Purity: about 99% according to $^1$H-NMR. A further purification can be carried out by repeated recrystallisation or chromatography and by fractional sublimation in vacuo.

The following compounds can be prepared analogously:

| Ex. | Starting material | Amine | Product Variant | Yield |
|---|---|---|---|---|
| S50 | S1 | 169224-65-1 | | 68% |
| S51 | S1 | 169224-65-1 | | 53% |

-continued
| Ex. | Starting material | Amine | Product Variant | Yield |
|---|---|---|---|---|
| S52 | 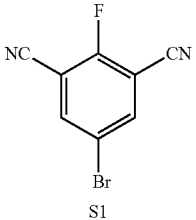 S1 | 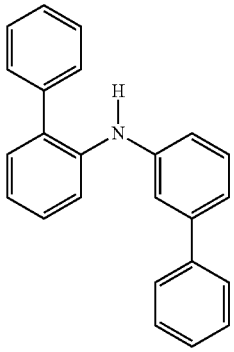 1258515-01-3 | 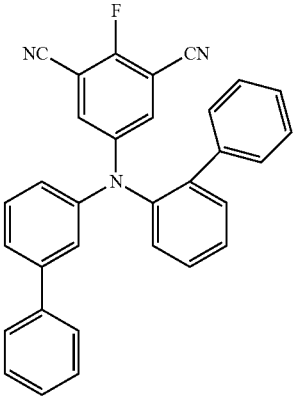 [SMILES: N#Cc1cc(N(c2cccc(-c3ccccc3)c2)c2ccccc2-c2ccccc2)cc(C#N)c1F] | 49% |
| S53 | 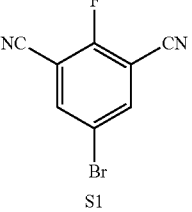 S1 | 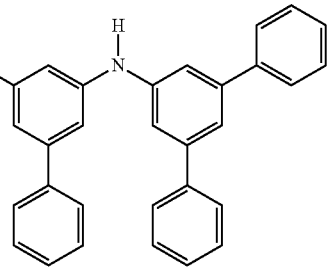 1290039-78-9 | 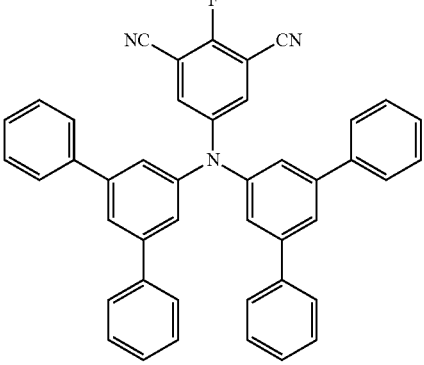 | 70% |
| S54 | 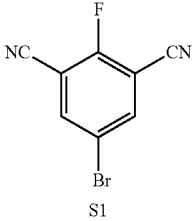 S1 | 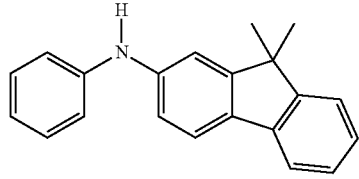 355832-04-1 | 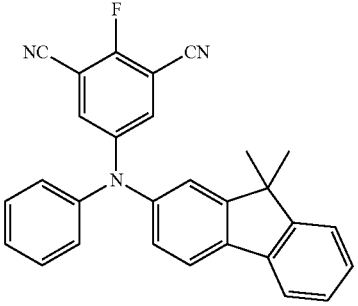 | 65% |
| S55 | 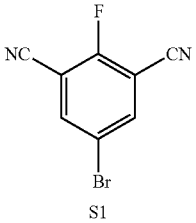 S1 | 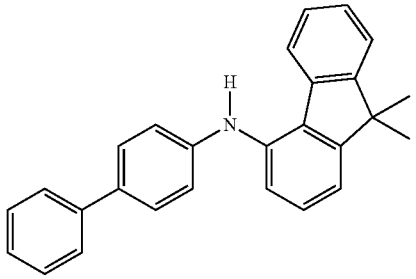 1421789-16-3 | 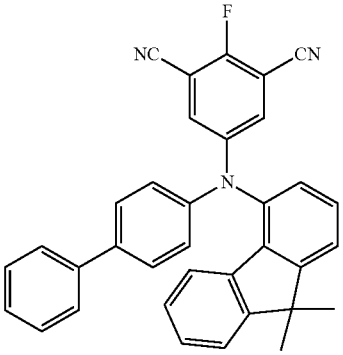 [SMILES: CC1(C)c2ccccc2-c2c(N(c3ccc(-c4ccccc4)cc3)c3cc(C#N)c(F)c(C#N)c3)cccc21] | 49% |

| Ex. | Starting material | Amine | Product Variant | Yield |
|---|---|---|---|---|
| S56 | 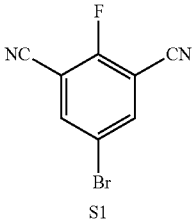 S1 | 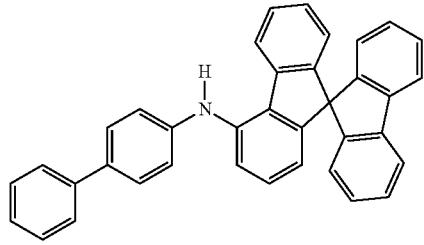 1421789-18-5 | 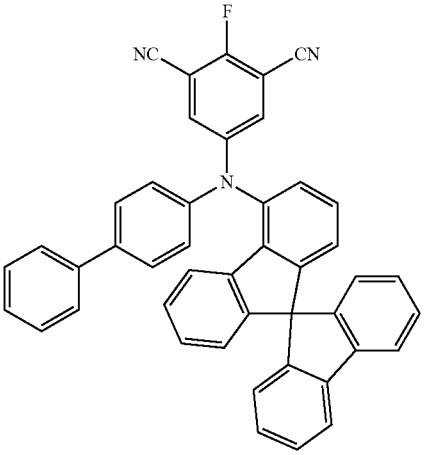 [SMILES: N#Cc1cc(N(c2ccc(-c3ccccc3)cc2)c2cccc3c2-c2ccccc2C32c3ccccc3-c3ccccc32)cc(C#N)c1F] | 43% |
| S57 | 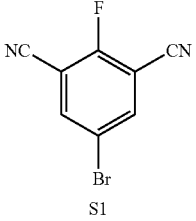 S1 | 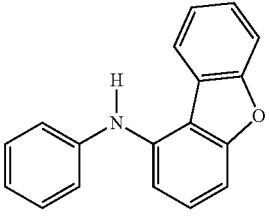 1325195-27-4 | 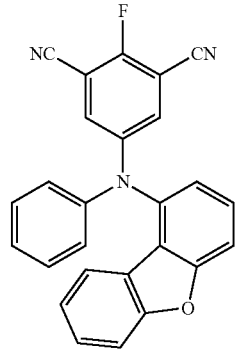 [SMILES: N#Cc1cc(N(c2ccccc2)c2cccc3oc4ccccc4c23)cc(C#N)c1F] | 46% |
| S58 | 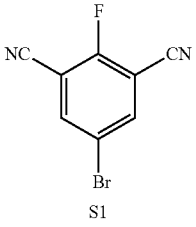 S1 | 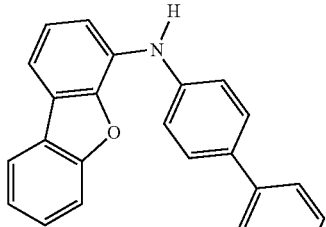 1318338-47-4 | 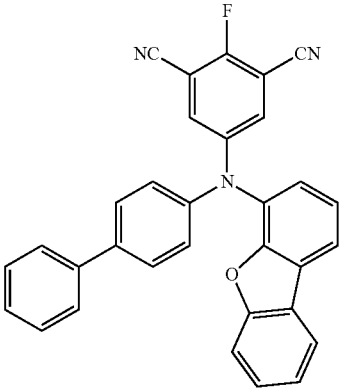 [SMILES: N#Cc1cc(N(c2ccc(-c3ccccc3)cc2)c2cccc3c2oc2ccccc23)cc(C#N)c1F] | 45% |

-continued
| Ex. | Starting material | Amine | Product Variant | Yield |
|---|---|---|---|---|
| S59 | 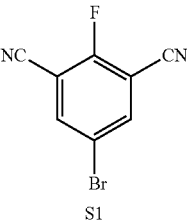 S1 | 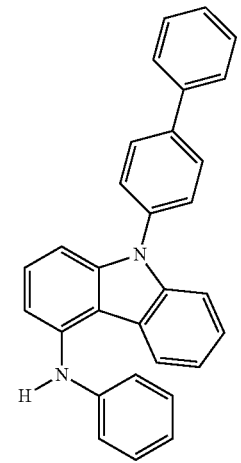 1259388-68-5 | 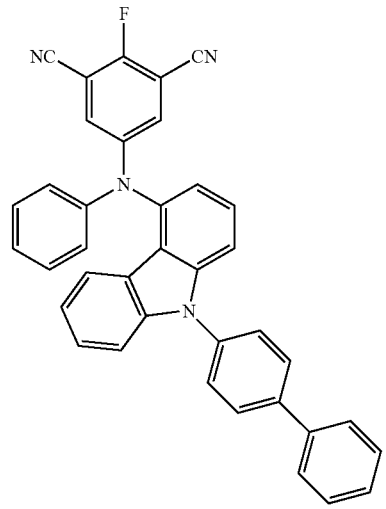 | 50% |
| S60 | 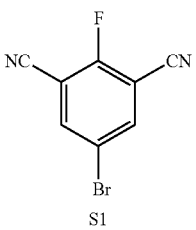 S1 | 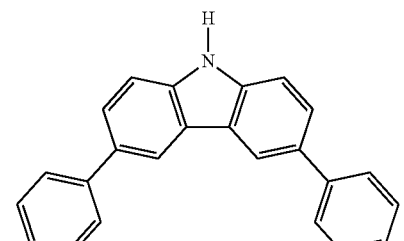 56525-79-2 | 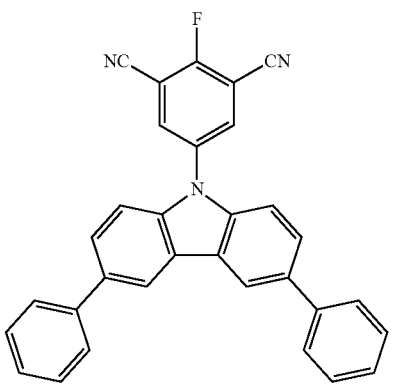 | 32% |
| S61 | 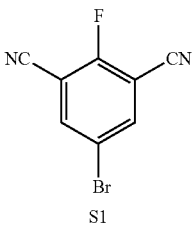 S1 | 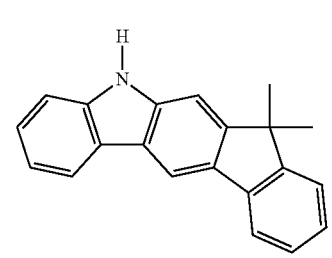 1257220-47-5 | 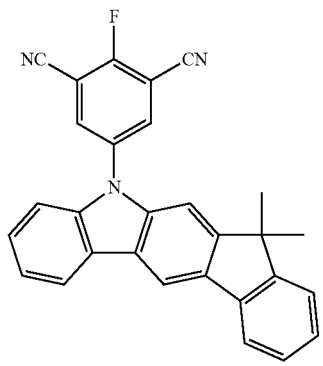 [SMILES: CC1(C)c2ccccc2-c2cc3c4ccccc4n(-c4cc(C#N)c(F)c(C#N)c4)c3cc21] | 28% |
| S62 | 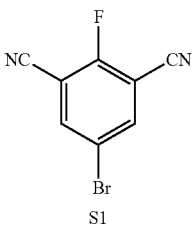 S1 | 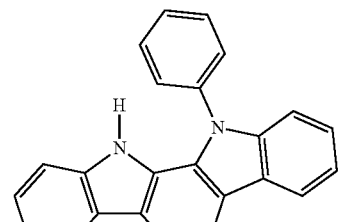 1024598-06-8 | 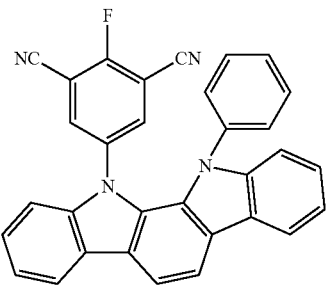 [SMILES: N#Cc1cc(-n2c3ccccc3c3ccc4c5ccccc5n(-c5ccccc5)c4c32)cc(C#N)c1F] | 21% |

-continued
| Ex. | Starting material | Amine | Product Variant | Yield |
|---|---|---|---|---|
| S63 | 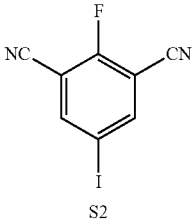 S2 | 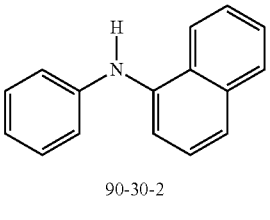 [SMILES: c1ccc(Nc2cccc3ccccc23)cc1] 90-30-2 | 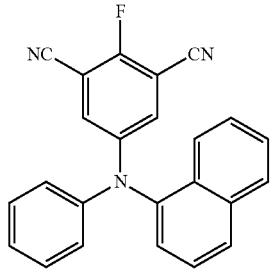 [SMILES: N#Cc1cc(N(c2ccccc2)c2cccc3ccccc23)cc(C#N)c1F] | 67% |
| S64 | 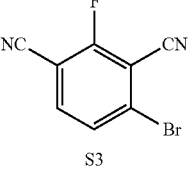 S3 | 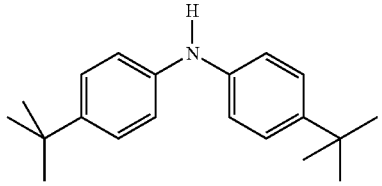 4627-22-9 | 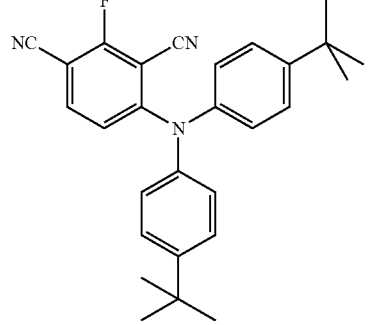 | 69% |
| S65 | 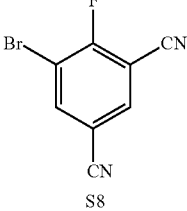 S8 | 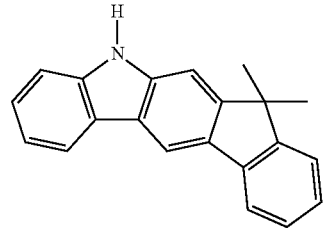 1257220-47-5 | 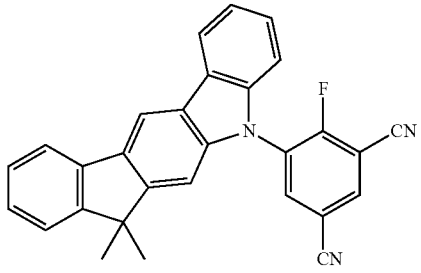 [SMILES: CC1(C)c2ccccc2-c2cc3c4ccccc4n(-c4cc(C#N)cc(C#N)c4F)c3cc21] | |
| S66 | 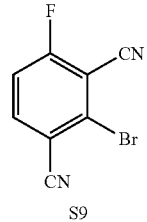 S9 | 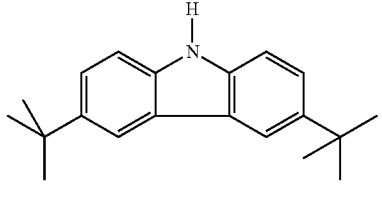 [SMILES: CC(C)(C)c1ccc2[nH]c3ccc(C(C)(C)C)cc3c2c1] | 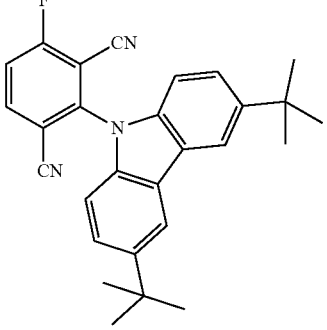 | |

| Ex. | Starting material | Amine | Product Variant | Yield |
|-----|-------------------|-------|-----------------|-------|
| S67 | 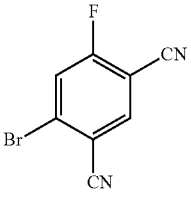 17654-69-2 | 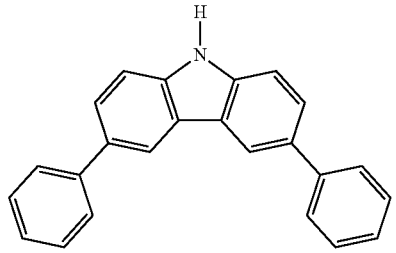 56525-79-2 | 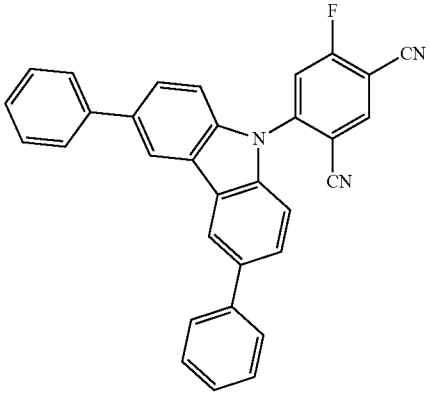 [SMILES: N#Cc1cc(C#N)c(-n2c3ccc(-c4ccccc4)cc3c3cc(-c4ccccc4)ccc32)cc1F] | |

Example S68: Reaction of the Synthetic Building Blocks in a Nucleophilic Aromatic Substitution

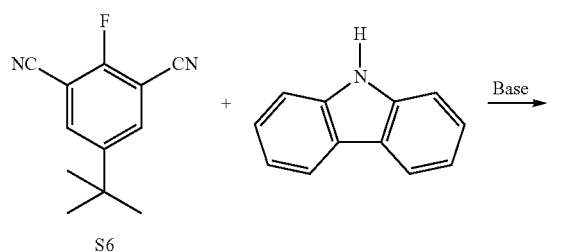

Variant A:

20.1 g (120 mmol) of carbazole [51555-21-6] are added in portions to a vigorously stirred suspension of 4.8 g (120 mmol) of sodium hydride, 60% by weight dispersion in mineral oil, in 200 ml of THF with ice-cooling at about +10° C.—care evolution of hydrogen! Foaming! When the addition is complete, the mixture is stirred for a further 30 min., and 20.2 g (100 mmol) with 2-fluoro-5-tert-butylisophthalonitrile, S6 are then added in portions with ice-cooling at such a rate that the temperature does not exceed +20° C. When the addition is complete, the mixture is stirred at +10° C. for a further 2 h, the cooling bath is then removed, the mixture is allowed to warm to 20-25° C. stirred for a further 2 h and then warmed at 40° C. for a further 12 h. After cooling to room temperature, the mixture is quenched by dropwise addition of 30 ml of MeOH, and the reaction mixture is then evaporated virtually to dryness in vacuo. The residue is washed by stirring at elevated temperature twice with a mixture of 100 ml of methanol and 100 ml of water and then once with 200 ml of methanol. The purification is carried out by recrystallisation five times from DMF and fractional sublimation twice (p about $1 \times 10^{-5}$ mbar, T about 180° C.). Yield: 23.1 g (66 mmol) 66%. Purity: 99.9 according to HPLC.

Variant B:

Procedure analogous to variant A, but the carbazole is initially introduced in THF, and 48 ml (120 mmol) of n-BuLi, 2.5 molar in n-hexane are then added dropwise. Yield: 20.6 g (59 mmol) 59%. Purity: 99.9 according to HPLC.

Variant C:

A vigorously stirred suspension of 20.1 g (120 mmol) of carbazole [51555-21-6], 20.2 g (100 mmol) with 2-fluoro-5-tert-butylisophthalonitrile, S6, 31.8 g (150 mmol) of tripotassium phosphate, anhydrous and 100 g of glass beads is stirred at 160° C. for 16 h in 300 ml of dimethylacetamide. After cooling, 500 ml of water are added, the solid which has precipitated out is filtered off with suction, washed twice with 100 ml of water each time, twice with 100 ml of methanol each time and then dried in vacuo. Further purification analogous to variant A. Yield: 22.0 g (63 mmol) 63%. Purity: 99.9 according to HPLC.

The following compounds can be prepared analogously:

| Ex. | Starting material | Product Variant | Yield |
|---|---|---|---|
| S69 | | A | 71% |
| S70 | S13<br>Use of 50 mmol | | 55% |
| S71 | S22 | | 69% |

| Ex. | Starting material | Product Variant | Yield |
|---|---|---|---|
| S72 | 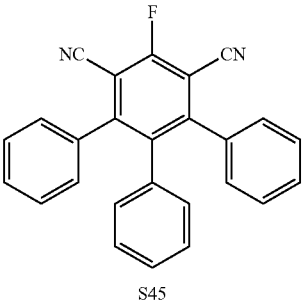 [SMILES: N#Cc1c(F)c(C#N)c(-c2ccccc2)c(-c2ccccc2)c1-c1ccccc1 ; "S45"]<br>S45 | 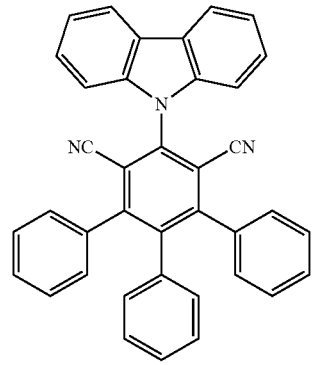 [SMILES: N#Cc1c(-c2ccccc2)c(-c2ccccc2)c(-c2ccccc2)c(C#N)c1-n1c2ccccc2c2ccccc21] | 65% |
| S73 | 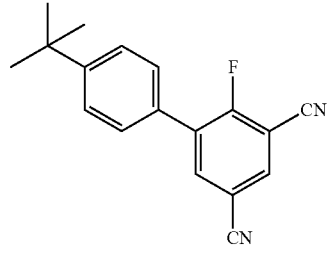<br>S46 | 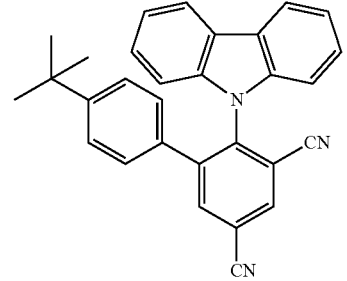 [SMILES: CC(C)(C)c1ccc(-c2cc(C#N)cc(C#N)c2-n2c3ccccc3c3ccccc32)cc1] | 70% |
| S74 | 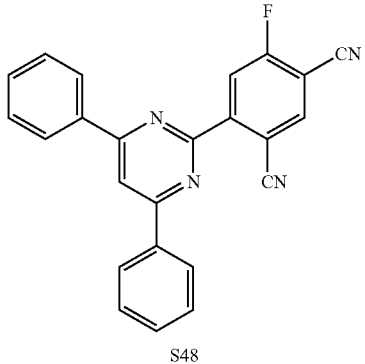 [SMILES: N#Cc1cc(C#N)c(-c2nc(-c3ccccc3)cc(-c3ccccc3)n2)cc1F ; "S48"]<br>S48 | 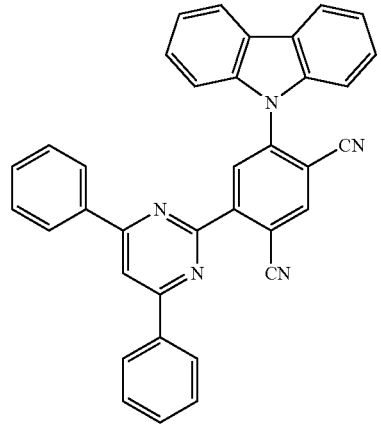 [SMILES: N#Cc1cc(C#N)c(-n2c3ccccc3c3ccccc32)cc1-c1nc(-c2ccccc2)cc(-c2ccccc2)n1] | 66% |
| S75 | 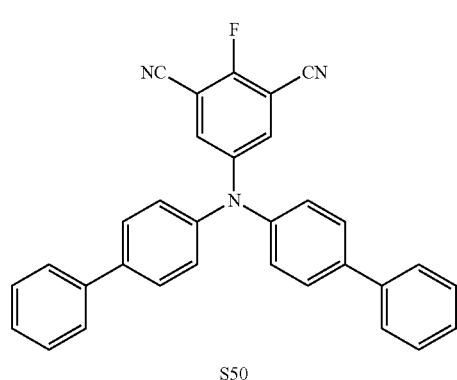 [SMILES: N#Cc1cc(N(c2ccc(-c3ccccc3)cc2)c2ccc(-c3ccccc3)cc2)cc(C#N)c1F ; "S50"]<br>S50 | 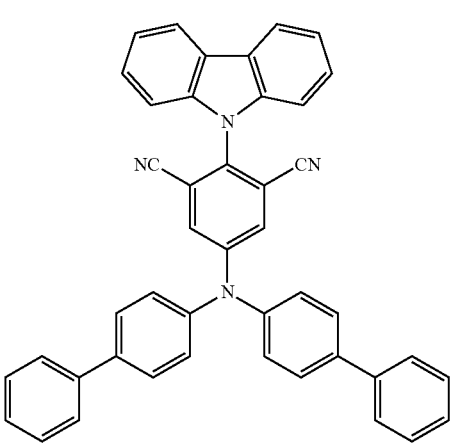 [SMILES: N#Cc1cc(N(c2ccc(-c3ccccc3)cc2)c2ccc(-c3ccccc3)cc2)cc(C#N)c1-n1c2ccccc2c2ccccc21] | 54% |

Example S76: Palladium-Catalysed Cyanation of Chlorofluoroaromatic Compounds

Procedure analogous to M. Shevlin, Tetrahedron Letters, 2010, 51, 4833.

Catalyst Solution:

3 ml of a mixture of 2.81 g of concentrated sulfuric acid in 28 ml of N,N-dimethylacetamide are added to a solution of 2.73 g (5.7 mmol) of X-Phos and 643 mg (2.9 mmol) of palladium(II) acetate in 60 ml of N,N-dimethylacetamide, and the mixture is stirred at 80° C. for 30 min., during which a dark-brown solution forms.

1 ml of the catalyst solution is added to a vigorously stirred mixture of 23.6 g (143 mmol) of 1,3-dichloro-2-fluorobenzene [2268-05-5], 20.2 g (172 mmol) of zinc(II) cyanide, 750 mg (11.5 mmol) of zinc dust and 280 ml of N,N-dimethylacetamide, and the mixture is stirred at 120° C. for 3 h. When the reaction is complete, the solvent is substantially removed in vacuo, the residue is taken up in 500 ml of ethyl acetate, salts remaining are filtered off, the filtrate is washed three times with 300 ml of water and once with 300 ml of sodium chloride solution and dried over magnesium sulfate. The residue remaining after removal of the solvent is recrystallised twice from cyclohexane. Yield: 15.8 g (109 mmol) 76%. Purity: about 97% according to $^1$H-NMR.

The following compound can be prepared analogously:

| Ex. | Starting material | Product | Yield |
|---|---|---|---|
| S77 | ![Br, F, Br structure] 444-13-3 | ![NC, F, CN structure] | 68% |

The invention claimed is:

1. A process for the preparation of a compound of the formula (34) or formula (35) or formula (36),

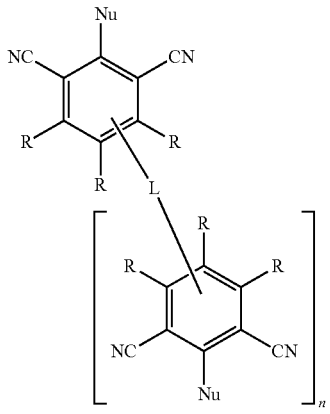

formula (34)

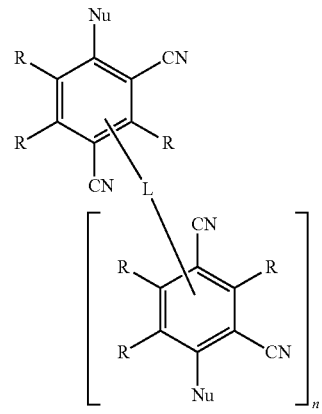

formula (35)

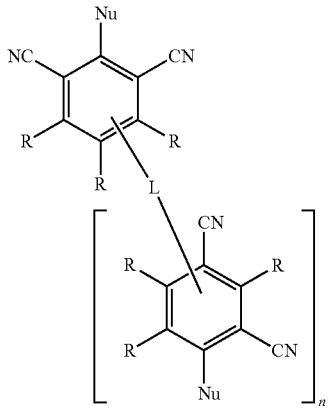

formula (36)

wherein
Nu stands for a nucleophilic group,
L is not present;
R is selected on each occurrence, identically or differently, from the group consisting of H, D, Cl, Br, I, NAr$_2$, N(R$^1$)$_2$, where R$^1$ is not equal to H, C(=O)Ar, C(=O)R$^1$, BR$^1$, P(=O)Ar$_2$, PAr$_2$, OAr, SAr, S(=O)Ar, S(=O)$_2$Ar, Si(R$^1$)$_3$, a straight-chain alkyl or alkoxy group having 1 to 40 C atoms or a branched or cyclic alkyl or alkoxy group having 3 to 40 C atoms or an alkenyl or alkynyl group having 2 to 40 C atoms, each of which may be substituted by one or more radicals R$^1$, where in each case one or more non-adjacent CH$_2$ groups may be replaced by R$^1$C=CR$^1$, C≡C, Si(R$^1$)$_2$, C=NR$^1$, P(=O)(R$^1$), NR$^1$, O, S or CONR$^1$ and where one or more H atoms may be replaced by D, F, Cl, Br or I, or an aromatic or heteroaromatic ring system having 5 to 60 aromatic ring atoms, which may in each case be substituted by one or more radicals $R^1$; two or more adjacent substituents R here may optionally form a monocyclic or polycyclic, aliphatic, aromatic or heteroaromatic ring system, which may be substituted by one or more radicals $R^1$;

Ar is on each occurrence, identically or differently, an aromatic or heteroaromatic ring system having 5-30 aromatic ring atoms, which may be substituted by one or more radicals $R^1$; two radicals Ar here which are bonded to the same N atom or P atom may also be bridged to one another by a single bond or a bridge selected from $N(R^1)$, $C(R^1)_2$, O, S or $BR^1$;

$R^1$ is selected on each occurrence, identically or differently, from the group consisting of H, D, F, Cl, Br, I, CN, $NO_2$, $N(R^2)_2$, $P(=O)(R^2)_2$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals $R^2$, where one or more non-adjacent $CH_2$ groups may be replaced by $R^2C=CR^2$, $C\equiv C$, $Si(R^2)_2$, $C=NR^2$, $P(=O)(R^2)$, SO, $SO_2$, $NR^2$, O, S or $CONR^2$ and where one or more H atoms may be replaced by D, F, Cl, Br, I or CN, an aromatic or heteroaromatic ring system having 5 to 60 aromatic ring atoms, which may in each case be substituted by one or more radicals $R^2$; two or more adjacent substituents $R^1$ here may optionally form a monocyclic or polycyclic, aliphatic ring system, which may be substituted by one or more radicals $R^2$;

$R^2$ is selected on each occurrence, identically or differently, from the group consisting of H, D, F, CN, an aliphatic hydrocarbon radical having 1 to 20 C atoms, an aromatic or heteroaromatic ring system having 5 to 30 aromatic ring atoms, in which one or more H atoms may be replaced by D, F, Cl, Br, I or CN, where two or more adjacent substituents $R^2$ may form a mono- or polycyclic, aliphatic ring system with one another;

n is 0;

which comprises reacting a compound of the formula (1), or formula (2) or formula (3),

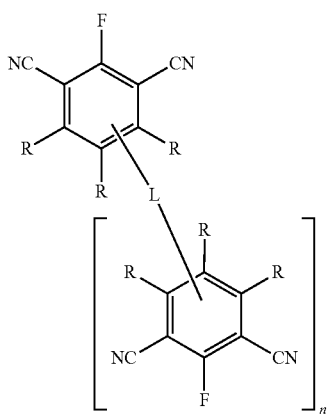

formula (1)

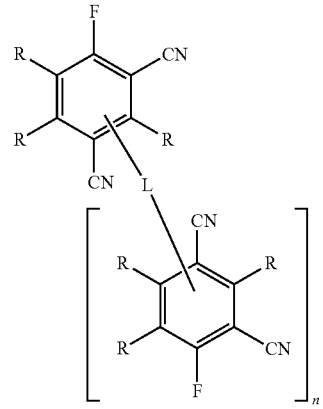

formula (2)

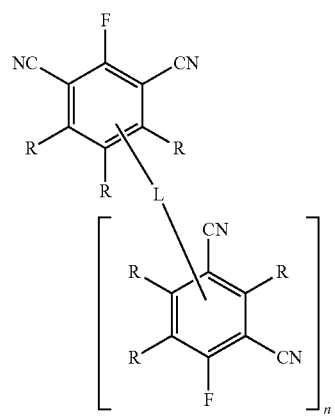

formula (3)

with a nucleophile.

2. The process according to claim 1, wherein the compound of the formula (1), (2) or (3) is selected from the compounds of the formulae (1a) to (1e), (2a) to (2g),

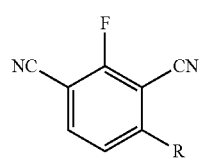

formula (1a)

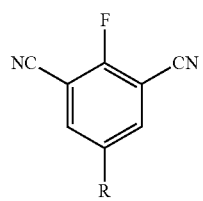

formula (1b)

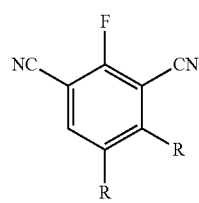

formula (1c)

-continued formula (1d)
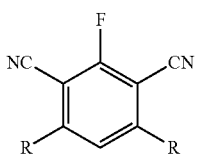

formula (1e)
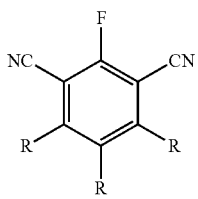

formula (2a)
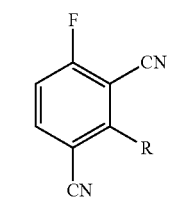

formula (2b)
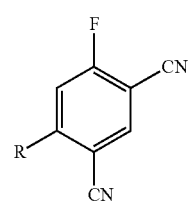

formula (2c)
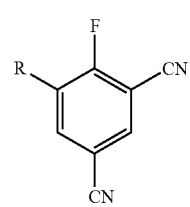

formula (2d)
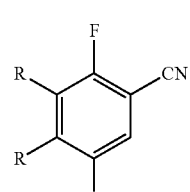

formula (2e)
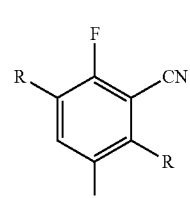

formula (2f)
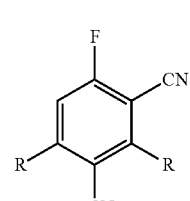

-continued formula (2g)
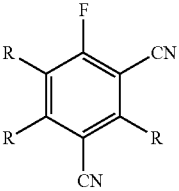

where the symbols used has the meanings given in claim 1.

3. The process according to claim 1, wherein two adjacent radicals R form a ring of the formula (4) with one another, formula (4)
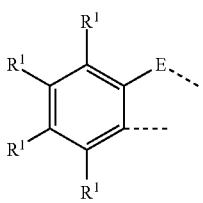

where $R^1$ has the meanings given above, the dashed bonds indicate the linking of the group to the benzene skeleton and furthermore:

E is selected from the group consisting of $C(R^1)_2$, $NR^1$, O, S, $BR^1$ or $Si(R^1)_2$.

4. The process according to claim 1, wherein R is selected on each occurrence, identically or differently, from the group consisting of H, $NAr_2$, $C(=O)Ar$, $C(=O)R^1$, $P(=O)Ar_2$, $PAr_2$, $Si(R^1)_3$, a straight-chain alkyl group having 1 to 10 C atoms or a branched or cyclic alkyl group having 3 to 10 C atoms or an alkenyl group having 2 to 10 C atoms, each of which may be substituted by one or more radicals $R^1$, where in each case one or more non-adjacent $CH_2$ groups may be replaced by $R^1C=CR^1$ or O and where one or more H atoms may be replaced by F, an aromatic or heteroaromatic ring system having 5 to 40 aromatic ring atoms, which may in each case be substituted by one or more radicals $R^1$; two or more adjacent substituents R here may optionally form a monocyclic or polycyclic, aliphatic, aromatic or heteroaromatic ring system, which may be substituted by one or more radicals $R^1$.

5. The process according to claim 1, wherein none of the radicals R, $R^1$ or $R^2$ contains condensed aryl or heteroaryl groups in which six-membered rings are condensed directly onto one another.

6. The process according to claim 1, wherein at least one radical R is selected from the group consisting of an aromatic or heteroaromatic ring system having 5 to 24 aromatic ring atoms, which may be substituted by one or more radicals $R^1$.

7. The process according to claim 1, wherein at least one radical R is selected from the group consisting of an aromatic or heteroaromatic ring system having 5 to 24 aromatic ring atoms, which may be substituted by one or more radicals $R^1$, wherein $R^1$ is benzene, biphenyl, terphenyl, quaterphenyl, 1-, 2-, 3- or 4-spirobifluorene, 1-, 2-, 3- or 4-fluorene, 1- or 2-naphthyl, pyrrole, furan, thiophene, indole, benzofuran, benzothiophene, carbazole, azacarbazole, dibenzofuran, dibenzothiophene, pyridine, pyrimidine, pyrazine, pyridazine, triazine, imidazole, benzimidazole, pyrazole, thiazole, oxazole, oxadiazole, triazole, phenanthrene, triphenylene or combinations of two or three of these groups, each of which may be substituted by one or more radicals $R^1$, or in that at least one substituent R is selected from one of the groups of the formulae (7) to (18)

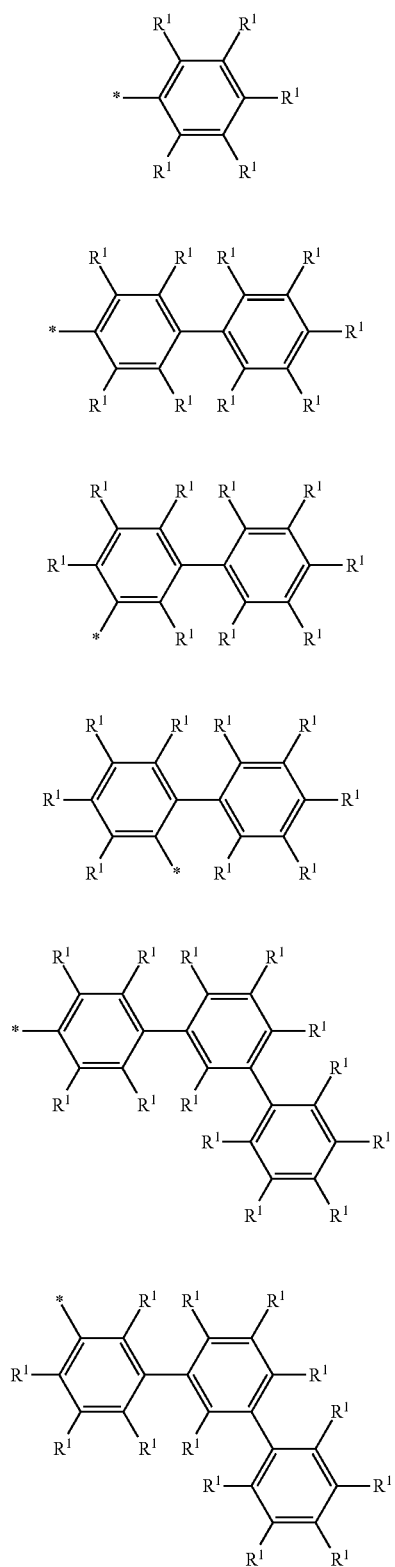

formula (7)
formula (8)
formula (9)
formula (10)
formula (11)
formula (12)

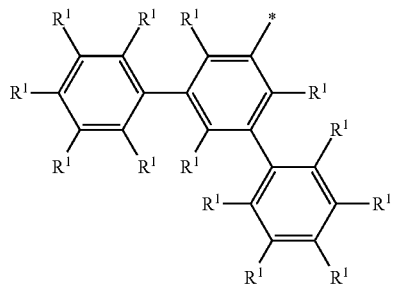

formula (13)

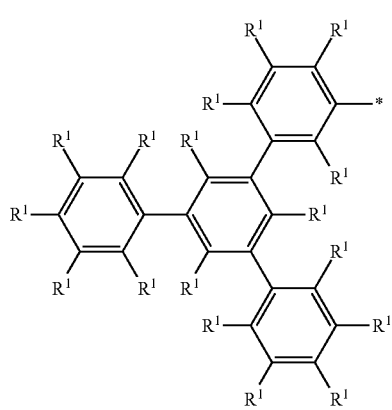

formula (14)

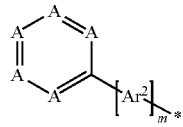

formula (15)

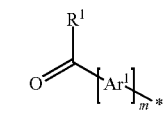

formula (16)

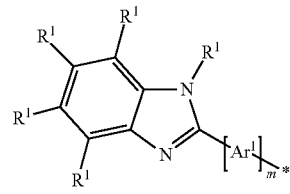

formula (17)

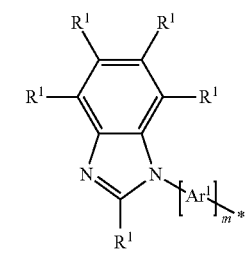

formula (18)

where the symbols used have the meanings given in claim 1, * indicates the position of the bonding of the group and furthermore:

$A$ is on each occurrence, identically or differently, $CR^1$ or N, with the proviso that one, two or three groups A stand for N;

$Ar^1$ is, identically or differently on each occurrence, a divalent aromatic or heteroaromatic ring system having 5 to 16 aromatic ring atoms, which may be substituted by one or more radicals R¹;

m is 0 or 1.

8. The process according to claim 7, wherein at least one radical R is selected from the group consisting of an aromatic or heteroaromatic ring system having 5 to 24 aromatic ring atoms, which may be substituted by one or more radicals R¹, wherein R¹ is benzene, ortho-, meta- or para-biphenyl, ortho-, meta-, para- or branched terphenyl, ortho-, meta- para- or branched quaterphenyl, 1-, 2-, 3- or 4-spiro-bifluorene, 1-, 2-, 3- or 4-fluorene, 1- or 2-naphthyl, pyrrole, furan, thiophene, indole, benzofuran, benzothiophene, carbazole, azacarbazole, dibenzofuran, dibenzothiophene, pyridine, pyrimidine, pyrazine, pyridazine, triazine, imidazole, benzimidazole, pyrazole, thiazole, oxazole, oxadiazole, triazole, phenanthrene, triphenylene or combinations of two or three of these groups, each of which may be substituted by one or more radicals R¹.

9. The process according to claim 1, wherein at least one radical R is selected from the group consisting of triarylamine, carbazole, indenocarbazole, indolocarbazole, azacarbazole, indole, furan, benzofuran, dibenzofuran, thiophene, benzothiophene or dibenzothiophene, each of which may be substituted by one or more radicals R¹, or at least one substituent R stands for NAr₂, where the two groups Ar may also be bridged to one another by a group selected from NR¹, O, S, C(R¹)₂, Si(R¹)₂ or BR¹.

10. The process according to claim 1, wherein at least one radical R is selected from the groups of the formulae (19) to (33), Formel (19)

Formel (20)
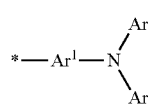

Formel (21)
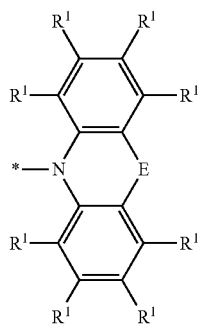

Formel (22)
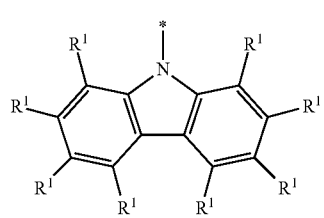

Formel (23)
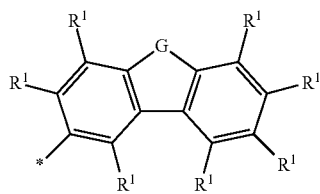

Formel (24)
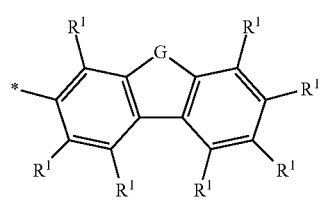

Formel (25)
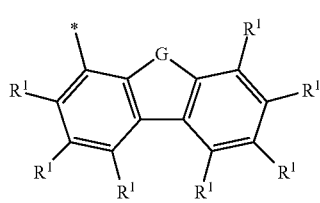

Formel (26)
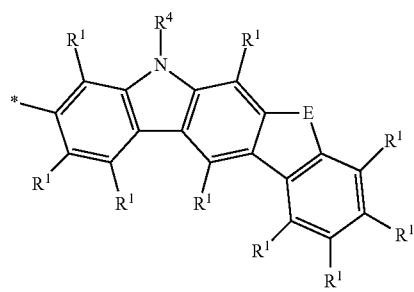

Formel (27)
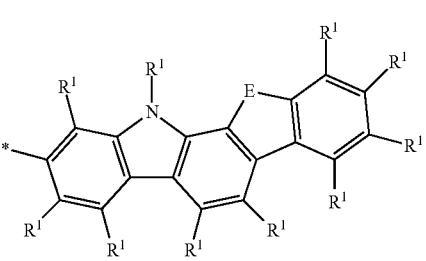

Formel (28)
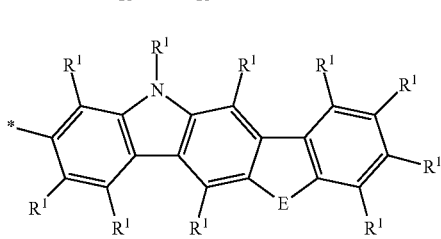

Formel (29)
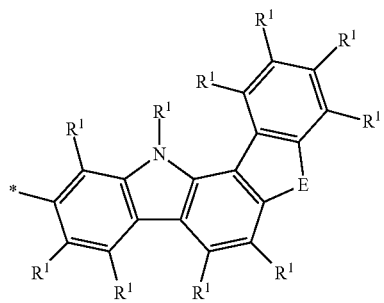
Formel (30)
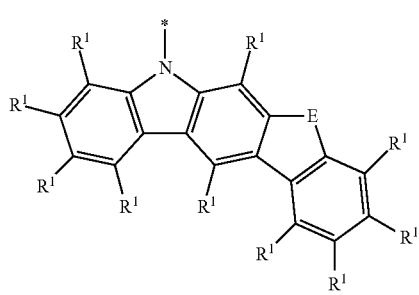
Formel (31)
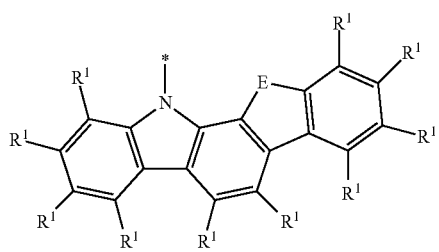
where the symbols used have the meanings given in claim 1 and furthermore:
G is selected from the group consisting of $NR^1$, O or S; where in each case one or two groups $CR^1$ may be replaced by N.
11. The process according to claim 1, wherein the following compounds are excluded from the formulas (1'), (2'):
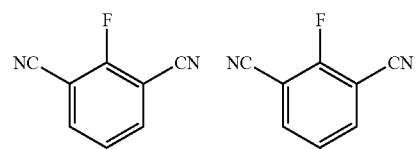
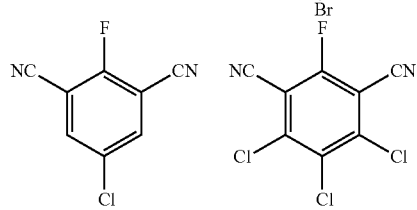
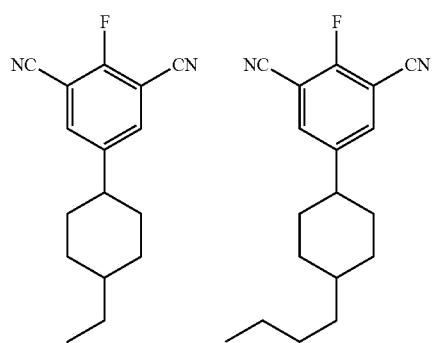
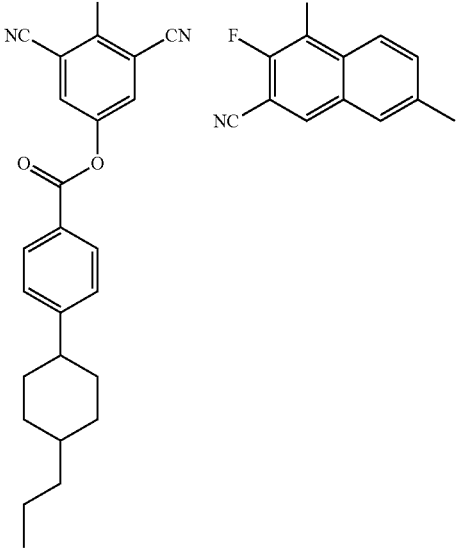
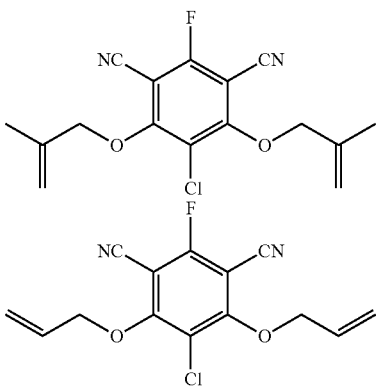

135
-continued
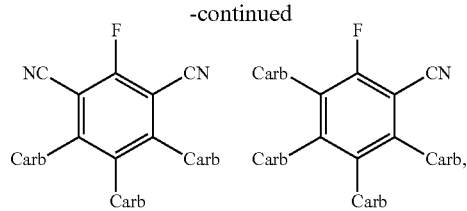
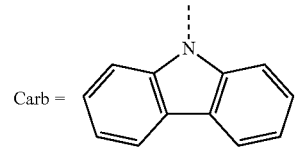
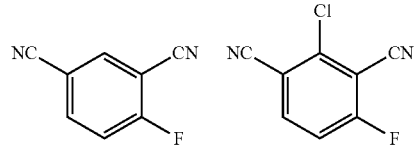
136
-continued
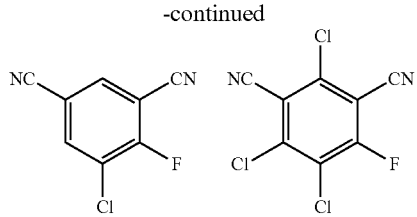
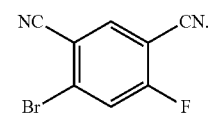
* * * * *